(12) United States Patent
Venkiteswaran et al.

(10) Patent No.: US 8,476,006 B2
(45) Date of Patent: Jul. 2, 2013

(54) STORE-OPERATED CALCIUM CELLULAR ASSAY

(75) Inventors: Gayatri Venkiteswaran, Bangalore (IN); Gaiti Hasan, Bangalore (IN)

(73) Assignee: National Center for Biological Sciences, Bangalore (IN)

( * ) Notice: Subject to any disclaimer, the term of this patent is extended or adjusted under 35 U.S.C. 154(b) by 553 days.

(21) Appl. No.: 12/628,064

(22) Filed: Nov. 30, 2009

(65) Prior Publication Data

US 2011/0130452 A1 Jun. 2, 2011

(51) Int. Cl.
*C12Q 1/00* (2006.01)
*C12N 5/071* (2010.01)
*G01N 33/567* (2006.01)
*G01N 33/20* (2006.01)
*G01N 21/76* (2006.01)
*C12N 5/02* (2006.01)
*C07F 9/02* (2006.01)

(52) U.S. Cl.
USPC ............... 435/4; 424/93.7; 424/600; 424/9.6; 435/7.21; 435/325; 435/366; 436/79; 436/172; 554/79

(58) Field of Classification Search
None
See application file for complete search history.

(56) References Cited

PUBLICATIONS

Venkiteswaran, G and Hasan, G "Intracellular Ca2+ Signaling and Store-Operated Ca2+ Entry are Required in *Drosophila* Neurons for Flight", PNAS, Jun. 2009, 106(25) pp. 10326-10331 and suppl. content (pp. 1-9).*
Alberts et al., "Table 8-2. Some Commonly Used Cell Lines," *Molecular Biology of the Cell, 4th Edition* Mar. 2002, 1 page.
Alberts et al., "8. Manipulating Proteins, DNA, and RNA," *Molecular Biology of The Cell, 4th Edition*, Mar. 2002, 2 pages.
Banerjee et al., "Compensation of Inositol 1,4,5-Trisphosphate Receptor Function by Altering Sarco-Endoplasmic Reticulum calcium ATPase Activity in the *Drosophila* Flight Circuit" *The Journal of Neuroscience*, Aug. 9, 2006, pp. 8278-8288, vol. 26, No. 32, Society of Neuroscience.
Banerjee et al., "Loss of Flight and Associated Neuronal rhythmicity in Inositol 1,4,5-Trisphosphate Receptor Mutants of *Drosophila*," J. Neurosci., Sep. 8, 2004, 24(36), pp. 1-25.
Banerjee et al., "The InsP3 receptor: its role in neuronal physiology and neurodegeneration,". *BioEssays*, (2005), pp. 1038-1047, vol. 27.
Barnett et al., "Gene Targeting in a Centralized Facility," *Gene Knockout Protocols*, (2001), pp. 65-82, Humana Press, Inc. USA.
Bellen et al., "The BDGP Gene Disruption Project: Single transposon Insertions Associated with 40% of *Drosophila* Genes," Genetics, Jun. 2004, pp. 761-781, vol. 167, The Genetics Society of America.
Benzer, S., "Genetic Dissection of Behavior," *Scientific American*, Dec. 1973, pp. 24-37, vol. 229, No. 6, Scientific American, Inc., New York, NY.
Borodinsky et al., "Activity-dependent neurotransmitter-receptor matching at the neuromuscular junction," *PNAS* Jan. 2, 2007, pp. 335-340, vol. 104, No. 1, The National Academy of Sciences of the USA.
Brandman et al., "STIM2 is a Feedback Regulator that Stabilizes Basal Cytosolic and Endoplasmic Reticulum $Ca^{2+}$ Levels," Dec. 28, 2007, pp. pp. 1-25, vol. 131, No. 7, USA.
Budnik et al., "Altered Branching of Serotonin-containing Neurons in *Drosophila* Mutants Unable to Synthesize Serotonin and Dopamine," *The Journal of Neuroscience*, Aug. 1989, pp. 2866-2877, vol. 9, No. 8, Society of Neuroscience.
Buerstedde et al., "The DT40 web site: sampling and connecting the genes of a B cell line," *Nucleic Acids Research*, (2002), pp. 230-231, vol. 30, No. 1, Oxford University Press.
Cordova et al., "Spatiotemporal calcium signaling in a *Drosophila melanogaster* cell line stably expressing a *Drosophila* muscarinic acetylcholine receptor", *Invert Neurosci*, (2003), pp. 19-28, vol. 5, Springer-Verlag.
Echalier, G., "Chapter 3, *Drosophila* Continuous Cell Lines", *Drosophila Cells in Culture*, 1997, pp. 129-186.
Echalier, G., "Chapter 2, Primary Cell Cultures of *Drosophila* Cells", *Drosophila Cells in Culture*, 1997, pp. 69-127.
Feske et al., "A mutation in Orai1 causes immune deficiency of abrogating CRAC channel function", *Nature* May 11, 2006, pp. 179-185, vol. 441, Nature Publishing Group, London.
Feske et al., "Gene regulation mediated by calcium signals in T lymphocytes", *Nature Immunology*, Apr. 2001, pp. 316-324, vol. 2, No. 4.
Foskett, et al., "Inositol Trisphosphate Receptor $Ca^{2+}$ Release Channels", *Physiol. Rev.*, (2007), pp. 593-658, American Physiological Society.
Ganetzky et al., "Indirect Suppression Involving Behavioral Mutants with Altered Nerve Excitability in *Drosophila Melanogaster*", *Genetics*, Apr. 1982, pp. 597-614.
Harper et al., "Loperamide: A positive modulator for store-operated calcium channels?", PNAS, Dec. 1997, pp. 14912-14917, vol. 94.
Hasan, G., "Biological Implications of Inositol 1,4,5-Trisphosphate Signalling from Genetic Studies in Multicellular Organisms", *Proc. Indian natn Sci Acad. B69*, (2003), pp. 741-752, No. 5.
"Inositol 1,4,5,-tris-phosphate receptor", Interactive Fly, *Drosophila*, 4 pages, Jul. 16, 1997 <http://www.sdbonline.org/fly/dbzhnsky/ino3pr1.htm> , accessed Jan. 30, 2009.
Ishikawa et al., "A Pyrazole Derivative, YM-58483, Potentially Inhibits Store-Operated Sustained $CA^{2+}$ Influx and IL-2 Production in T Lymphocytes", *The Journal of Immunology*(2003), pp. 4441-4449, vol. 170, The American Association of Immunologists, Inc.
"Itp-r83A—Inositol 1,4,5,-tris-phosphate receptor", Ihop—Information Hyperlinked over Proteins [Itp-r83A],<http://www.ihop-net.org/UniPub/iHOP/gs/65860.html >, accessed Feb. 2, 2009, 3 pages.
Joshi et al., "Genetic Dissection of *itpr* Gene Function Reveals a Vital Requirement in Aminergic Cells of *Drosophila Larvae*", *Genetics*, Jan. 2004, pp. 225-236, vol. 166, The Genetics Society of America.

(Continued)

*Primary Examiner* — Chris R Tate
*Assistant Examiner* — Aaron J Kosar
(74) *Attorney, Agent, or Firm* — Foley & Lardner LLP

(57) ABSTRACT

The present technology provides a cell based assay for identifying compounds that modulate store-operated ionic calcium levels using itpr mutant cell lines, such as itpr-ku cells, which have abnormal ionic calcium levels.

8 Claims, 29 Drawing Sheets

PUBLICATIONS

Koert et al., "Functional Implications of Neurotransmitter Expression during Axonal Regeneration: Serotin, but Not Peptides, Auto-Regulate Axon Growth of an Identified Central Neuron" *The Journal of Neuroscience*, Aug. 1, 2001, pp. 5597-5606, vol. 21, No. 15, Society for Neroscience.

Kumar et al., "Role of intracellular Calcium in *Drosophila larval* growth and viability: A Microarray analysis", HGM2008 Poster Abstracts 14. Genomics of Model Organisms, Poster 563, 1 page, <http://hgm2008.hugo-international.org/Abstracts/Publish/WorkshopPosters/WorkshopPos . . . >, Oct. 1-2, 2008.

Luik et al. "Oligomerization of STIM1 couples ER calcium depletion to CRAC channel activation", *Nature*, Jul. 24, 2008, pp. 538-542, vol. 454, Nature Publishing Group.

Mahr et al., "The expression pattern of the *Drosophila* vesicular glutamate transporter: A marker protein for motoneurons and glutamatergic centers in the brain", *Gene Expression Patterns*, (2006), pp. 229-309, vol. 6, Elsevier.

Matsumoto et al., "Ataxia and epileptic seizures in mice lacking type 1 inositol 1,4,5-trisphosphate receptor", Nature, Jan. 11, 1996, 379 (6561), pp. 168-171.

Millar et al., "Functional Expression of a Cloned *Drosophila* Muscarinic Acetylcholine Receptor in a Stable *Drosophila* Cell Line", *The Journal of Experimental Biology*, (1995), pp. 1843-1850, vol. 198, The Company of Biologists Limited, Great Britain.

Parekh et al., "Store-Operated Calcium Channels", *Physiol Rev*, (2005), pp. 757-810, vol. 85, The American Physiological Society.

Peel et al., "ORAI and Store-Operated Calcium Influx in Human Airway Smooth Muscle Cells" *Am J. Respir Cell Mol Biol*, (2008), pp. 744-749, vol. 38.

Prakriya et al., "Orai1 is an essential pore subunit of the CRAC channel", *Nature*, Sep. 4, 2006, pp. 230-233, vol. 443, Nature Publishing Group.

Redondo et al., "Intracellular $CA^{2+}$ store depletion induces the formation of macromolecular complexes involving hTRPC1, hTRPC6, the type II $IP_3$ receptor and SEARCA3 in human platelets", *Biochimica et Biophysica Acta*, (2008), pp. 1163-1176, vol. 1783, Elsevier.

Sakuntabhai et al., "Mutations in *ATP2A2*, encoding a $CA^{2+}$ pump, cause Darier disease" *Nature Genetics*, Mar. 1999, pp. 271-277, vol. 21, No. 3, Nature America Inc.

Saribasak et al., "Method 19—Targeted Transfection of DT40 Cells" *Reviews and Protocols in DT40 Research, Subcellular Biochemistry*, (2006), pp. 419-421, vol. 40, Springer.

Srikanth et al., "Functional Properties of the *Drosophila melanogaster* Inositol 1,4,5-Trisphosphate Receptor Mutants", *Biophysical Journal*, Jun. 2004, pp. 3634-3646, vol. 86, The Biophysical Society.

Street et al., "The Type 1 Inositol 1,4,5-Triphosphate Receptor Gene is Altered in the *opisthotonos* Mouse", *The Journal of Neuroscience*, Jan. 15, 1997, pp. 635-645, vol. 17, No. 2, Society for Neuroscience.

Taylor, C. W., "Store-operated $CA^{2+}$ entry: a STIMulating stOrai", *Trends in Biochemical Sciences*, pp. 597-601, vol. 31, No. 11, Elsevier Ltd.

Thompson et al., "The Orai1 Severe Combined Immune Deficiency Mutation and Calcium Release-activated $CA^{2+}$ Channel Function in the Heterozygous Condition*", *The Journal of Biological Chemistry*, Mar. 13, 2009, pp. 6620-6626, vol. 284, No. 11, The American Society for Biochemistry and Molecular Biology, Inc., U.S.A.

Van De Leemput et al., "Deletion at *ITPR1* Underlies Ataxia in Mice and Spinocerebellar Ataxia 15 in Humans", *PLoS Genetics*, Jun. 2007, pp. 1076-1082, vol. 3, issue 6, Open Access Freely available online.

Venkiteswaran et al., "The InsP3R and Neuronal Calcium Homeostasis" Poster, *NCBS, TIFT*, Bangalore Cold Spring Harbor Meeting on Neurobiology of *Drosophila*, Oct. 3-7, 2007, 1 page.

Vig et al., "CRACM1 Multimers Form the Ion-Selective Pore of the CRAC Channel", *Current Biology*, Oct. 24, 2006, pp. 2073-2079, vol. 16, Elsevier Ltd.

Voorhoeve et al., "Knockdown stands up", *TRENDS in Biotechnology*, Jan. 2003, pp. 2-4, vol. 21, No. 1, Elsevier Science Ltd.

Wu et al., "Dissociated Neurons from Normal and Mutant *Drosophila* Larval Central Nervous System in Cell Culture", *The Journal of Neuroscience*, Sep. 1963, pp. 1888-1899, vol. 3, No. 9, Society for Neuroscience, U.S.A.

Xia et al., "Transgenic RNAi: accelerating and expanding reverse genetics in mammals", *Transgenic Research*, (2006), pp. 271-275, vol. 15, Springer.

Yeromin et al., "Molecular identification of the CRAC channel by altered ion selectivity in a mutant of Orai", Nature Sep. 14, 2006, 443(7108), pp. 226 -229.

Zhang et al., "Genome-wide RNAi screen of $CA^{2+}$ influx identifies genes that regulate $CA^{2+}$ release-activated $CA^{2+}$ channel activity", *PNAS*, Jun. 13, 2006, pp. 9357-9362, vol. 103, No. 24.

\* cited by examiner

STORE-OPERATED CALCIUM CELLULAR ASSAY

FIELD OF THE TECHNOLOGY

The field of the present technology relates to, among others, cell based assays for compound identification.

BACKGROUND

The major entry pathway of calcium ions ($Ca^{2+}$) in electrically nonexcitable cells is the store-operated calcium channel (SOC). The store-operated channel is encoded by the Orai gene and is the pore forming subunit of the $Ca^{2+}$-release activated $Ca^{2+}$ (CRAC) channel. See Prakriya, M. et al., Nature 443, 230-233 (2006); Vig, M. et al, Curr Biol 16, 2073-2079 (2006); and Yeromin, A. V., et al., Nature 443, 226-229 (2006). When intracellular stores of $Ca^{2+}$ are low or depleted, then $Ca^{2+}$ influx through the store-operated calcium channel is activated.

In the context of neuronal activity, calcium ions act as intracellular messengers during synaptic transmission and in developmental processes. Specific attributes of a $Ca^{2+}$ "signature" such as, amplitude, duration and frequency of the signal can determine the morphology of a neural circuit by affecting the outcome of cell migration, the direction taken by a growth-cone, dendritic development and synaptogenesis. See Berridge, M. J., Neuron, 21, 13-26 (1998). $Ca^{2+}$ signals also determine the nature and strength of neural connections in a circuit by specifying neurotransmitters and receptors. See Borodinsky, L. N. & Spitzer, N. C., Proc Natl Acad Sci USA, 104, 335-340 (2007). Thus, neuronal $Ca^{2+}$ signals can affect excitability and neural circuit formation.

The inositol 1,4,5-trisphosphate receptor (InsP3R, itpr) gene is a ligand gated $Ca^{2+}$-channel present on the membranes of intracellular $Ca^{2+}$ stores. See Banerjee, S. et al., J Neurosci 24, 7869-7878 (2004); Joshi, R. et al., Genetics 166, 225-236 (2004). It is thought to be involved in various aspects of neuronal function including excitability, neurotransmitter release, synaptic plasticity and gene transcription. See Banerjee, S. & Hasan, G., Bioessays, 27, 1035-1047 (2005); Berridge, M. J., Neuron 21, 13-26 (1998). Mutants in the gene coding for the mouse InsP3R1 are ataxic. See Matsumoto, M. et al., Nature 379, 168-171 (1996); Street, V. A. et al., J. Neurosci., 17, 635-645 (1997).

SUMMARY

An aspect of the present technology is a method of identifying a compound that modulates store-operated calcium entry levels in a cell, comprising providing a test compound to an itpr-ku mutant cell; and determining whether the test compound increases or decreases the abnormal store-operated calcium entry level of the itpr-ku cell, wherein a test compound that increases or decreases the calcium release through InsP3R and/or changes the store operated calcium entry in an itpr-ku mutant cell is a compound that modulates store-operated calcium entry levels. In one embodiment, the store-operated calcium entry level of the itpr-ku cell either increases or decreases to a level that approximates the calcium level of a control cell. In one embodiment control cell is (i) a wild-type, normal cell, (ii) a cell with a dOrai/Kum-170; itpr-ku mutant genotype, or (iii) a cell without the itpr-ku mutant genotype.

In a further embodiment, determining whether the test compound modulates the abnormal store-operated calcium entry level of the itpr-ku cell is achieved by performing calcium imaging of the store-operated calcium entry environment of the itpr-ku cell, and comparing the calcium imaging patterns before and after the addition of the test compound to the itpr-ku cell.

In another embodiment, the method further comprises comparing the calcium imaging patterns of the itpr-ku cell with the calcium imaging of the store-operated calcium entry environment of the control cell, wherein a similarity in calcium imaging patterns between the two cells indicates the test compound can modulate the store-operated calcium entry level of the itpr-ku cell. In one embodiment, the control cell is a (i) a wild-type, normal cell, (ii) a cell with a dOrai/Kum-170; itpr-ku mutant genotype, or (iii) a cell without the itpr-ku mutant genotype.

In another embodiment, the test compound is selected from the group consisting of a small molecule, an inorganic compound, an organic compound, a biomolecule, a chemical, a protein, a peptide, or a nucleic acid.

A method for treating a disease characterized by abnormal store-operated ionic calcium levels comprising administering a compound identified by the method of the present technology to an individual with such a disease. In one embodiment, the disease is severe combined immunodeficiency, acute pancreatitis, or Alzheimer's Disease.

In one embodiment, therefore, is a method of identifying a therapeutic compound useful for treating a disease that is characterized by an abnormal intracellular calcium level, comprising: (A) providing a candidate therapeutic compound to a cell which (i) comprises a mutated inositol 1,4,5-trisphosphate receptor gene and which (ii) is characterized by an abnormal intracellular calcium level compared to the calcium level of an equivalent cell which does not comprise the mutated inositol 1,4,5-trisphosphate receptor gene; (B) determining whether the candidate therapeutic compound increases or decreases the abnormal intracellular calcium level of the cell, and, if it does, then, (C) administering the candidate therapeutic compound to cells isolated from an individual who has a disease characterized by abnormal intracellular calcium levels; and (D) determining (i) whether the candidate therapeutic compound increases or decreases the abnormal intracellular calcium level of the isolated cells, and (ii) comparing any increase or decrease in the abnormal intracellular calcium level against the intracellular calcium level of normal cells isolated from a healthy individual who does not have the disease; wherein a candidate therapeutic compound that effectuates a change in the intracellular calcium level of the diseased cells toward the intracellular calcium level of the normal cells, is identified as a therapeutic compound useful for treating a disease that is characterized by an abnormal intracellular calcium level.

In one embodiment, the cell of (A) expresses no inositol 1,4,5-trisphosphate receptor gene other than the mutated inositol 1,4,5-trisphosphate receptor gene. In another embodiment, the mutated inositol 1,4,5-trisphosphate receptor gene comprises the mutations characteristic of the itpr-ku mutated gene, or mutations that are equivalent to the itpr-ku mutated gene. In another embodiment, the cell of (A) is a DT40 cell. In another embodiment, the cell is a *Drosophila* cell and the mutated inositol 1,4,5-trisphosphate receptor gene has the sequence of the itpr-ku mutated gene. In another embodiment, the cell of (A) is a mammalian cell. In a further embodiment, the cell of (A) is a human cell, and the isolated cells of the diseased individual of (C) are human cells. In one embodiment, the diseased cells are cells isolated from a human who has a disease selected from the group consisting of spino-cerebellar ataxia; severe combined immuno-deficiency, Darier's disease, an immunodeficiency, acute pancreatitis, Alzheimer's Disease.

In another aspect, the method further comprises administering the therapeutic compound to (i) the same individual from whom the diseased cells of (C) were isolated, or (ii) an individual who has the same disease or same type of disease as the individual from whom the diseased cells of (C) were isolated. In one embodiment, the therapeutic compound is formulated into a pharmaceutical formulation prior to administration to the individual. In one embodiment, the individual is a human male or human female.

In another aspect, the method comprises (i) imaging the intracellular calcium levels of cells isolated from the individual before and after administration of the therapeutic compound or the pharmaceutical formulation of the therapeutic compound to the individual, and (ii) determining if the abnormal intracellular calcium levels that are characteristic of the disease has changed toward the level of intracellular calcium levels of a normal, healthy cell. In one embodiment, the method further comprises administering the same or an increased or decreased amount of the pharmaceutical formulation to the individual and re-imaging the intracellular calcium levels of cells isolated from the individual to determine if the intracellular calcium level is near or at or is approximating the intracellular calcium level of a normal, healthy cell.

The foregoing summary is illustrative only and is not intended to be in any way limiting. In addition to the illustrative aspects, embodiments, and features described above, further aspects, embodiments, and features will become apparent by reference to the drawings and the following detailed description.

(a) Pseudocolour image representation of one embodiment of the measurement of store $Ca^{2+}$ and store operated $Ca^{2+}$ entry (SOCE) in primary cultures of neurons loaded with a $Ca^{2+}$ sensitive dye (Fluo-4) from wild type (WT) larvae and those in which either dOrai or dSTIM is knocked down using RNAi. Store $Ca^{2+}$ was measured by depleting stores upon addition of 10 μM thapsigargin (Tpg). SOCE was monitored by inclusion of $Ca^{2+}$ (to a free concentration of 1 mM) at t=225 s, to the extracellular buffer. Scale bar represents 10 μm. Warmer colors represent higher $Ca^{2+}$;

(b) Single cell traces of SOCE by $Ca^{2+}$ add-back after store depletion with thapsigargin. Arrows represent the peak values of response which has been plotted as a box chart in FIG. 1c;

(c) Box plots of the ΔF/F values of SOCE in neurons where the store has been depleted with thapsigargin treatment followed by addition of 1 mM $CaCl_2$ to the bath. The bigger boxes represent the spread of the ΔF/F values, the smaller squares represent the mean value and the diamonds on either side of the boxes represent outlier values. SOCE is severely compromised in neurons where dOrai (*PANOVA=0.04281) or dSTIM (**PANOVA=0.5875E-7) transcripts are down regulated compared to WT. Nearly 70-80% of cells that respond to thapsigargin treatment have detectable SOC and this was comparable between all the genotypes tested;

(d) Box plot comparison of ER store $Ca^{2+}$ levels between neurons of WT, RNAi controls and those with pan-neuronal down-regulation of dOrai or dSTIM. At least 150 cells of each genotype were analyzed to obtain an estimate of $[Ca^{2+}]ER$ which is significantly lower in cells where Orai (*PANOVA=2.61E-6) or STIM (**PANOVA=0.001) is downregulated as compared to WT;

(e) Kolmogorov-Smirnov (K-S) plot analyzing the distribution of intracellular $Ca^{2+}$ or $[Ca^{2+}]i$ in neurons loaded with the $Ca^{2+}$ sensitive ratiometric dye Indo-1. The frequency distribution is significantly shifted to the left for cells where dSTIM is knocked down, indicating a higher frequency of cells with reduced resting $Ca^{2+}$ levels (PK-S=0.01173); and (f) A box plot depiction of $[Ca^{2+}]i$ in 170 or more neurons down-regulated for dOrai or dSTIM with appropriate controls. $[Ca^{2+}]i$ was determined using the Grynkiewicz equation 44. $[Ca^{2+}]i$ in neurons with reduced dSTIM is significantly lower than in WT neurons (*PANOVA=0.02092).

Figure 2:
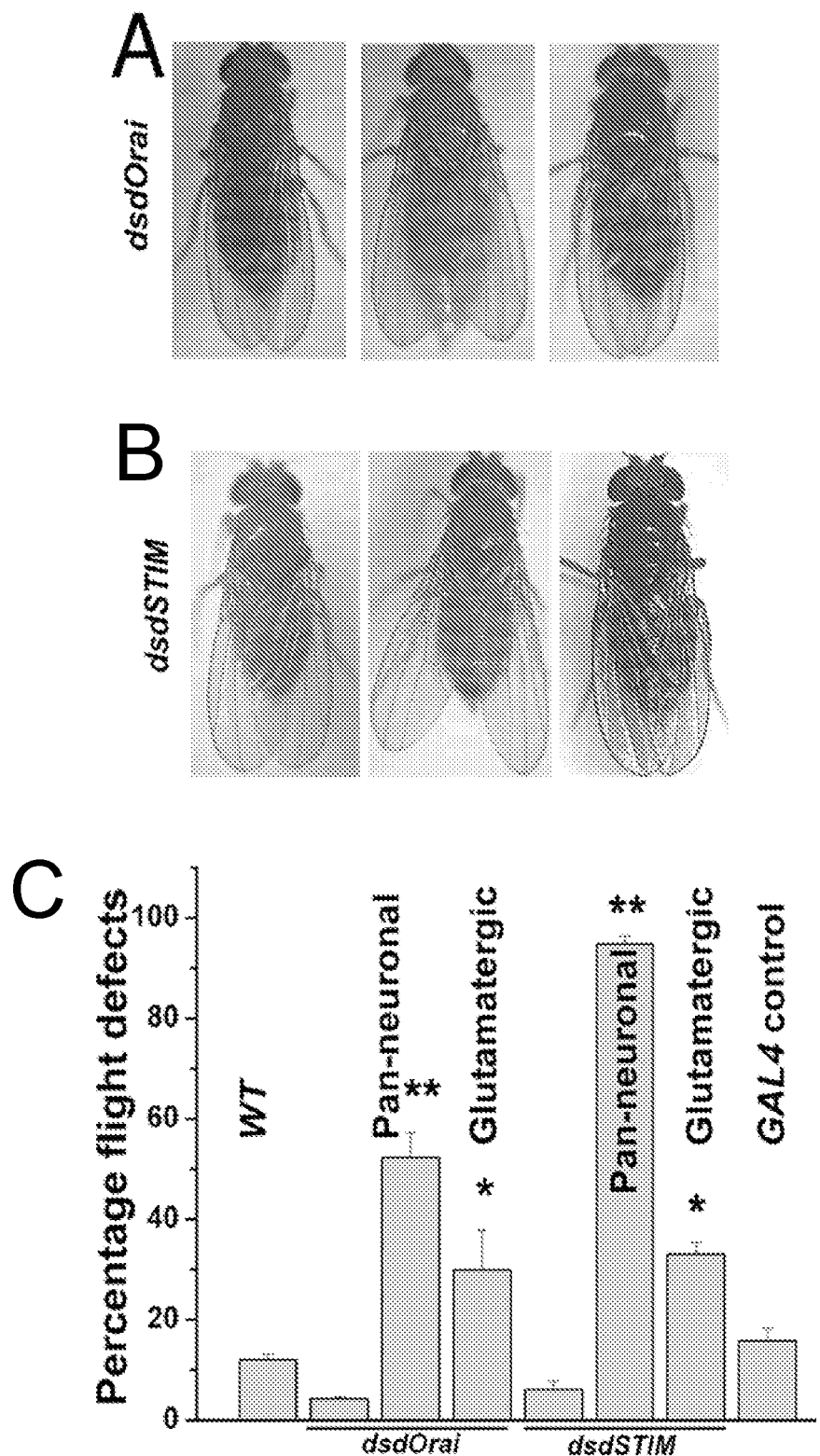
Figure 2:
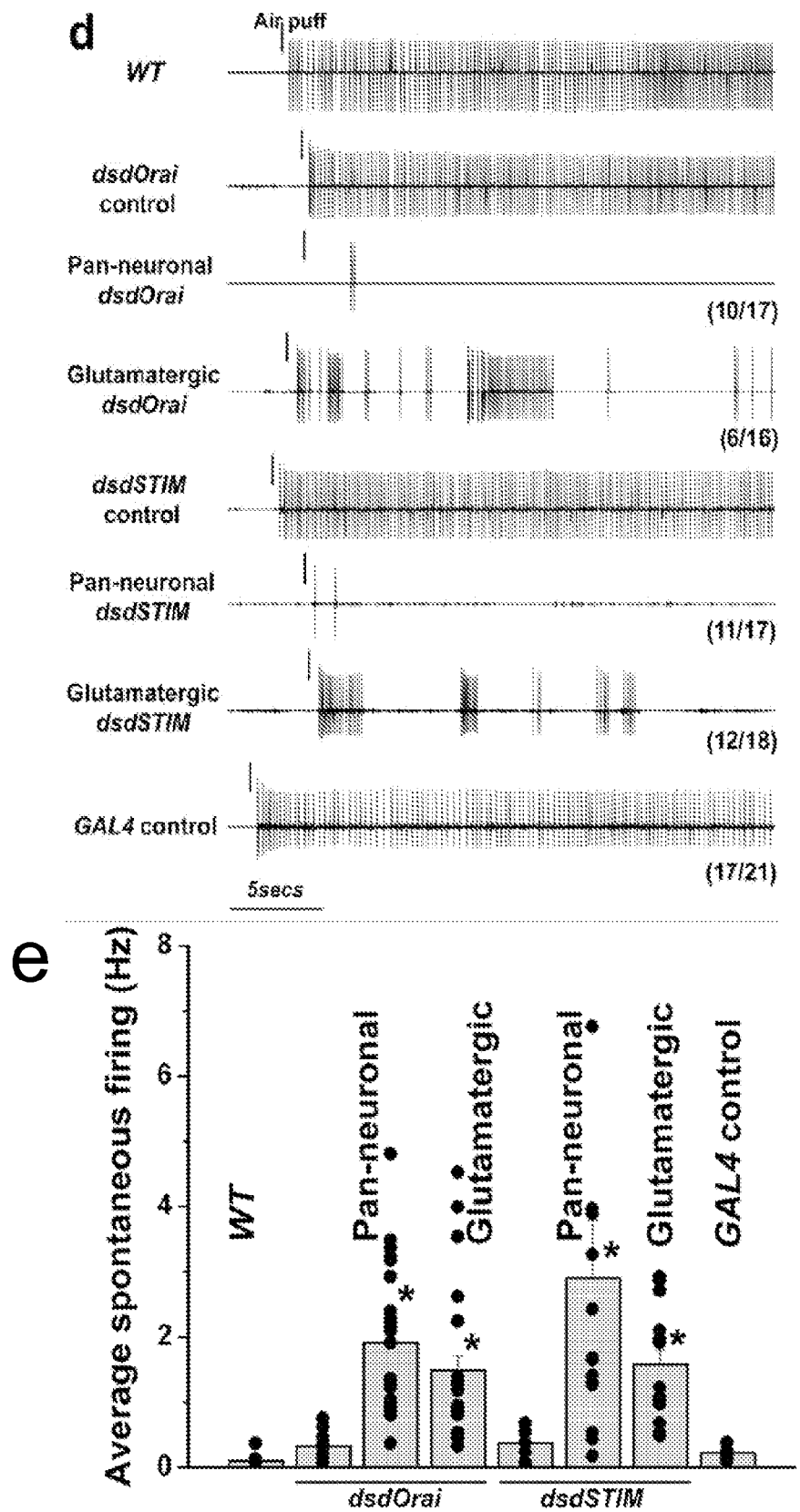
Figure 2:
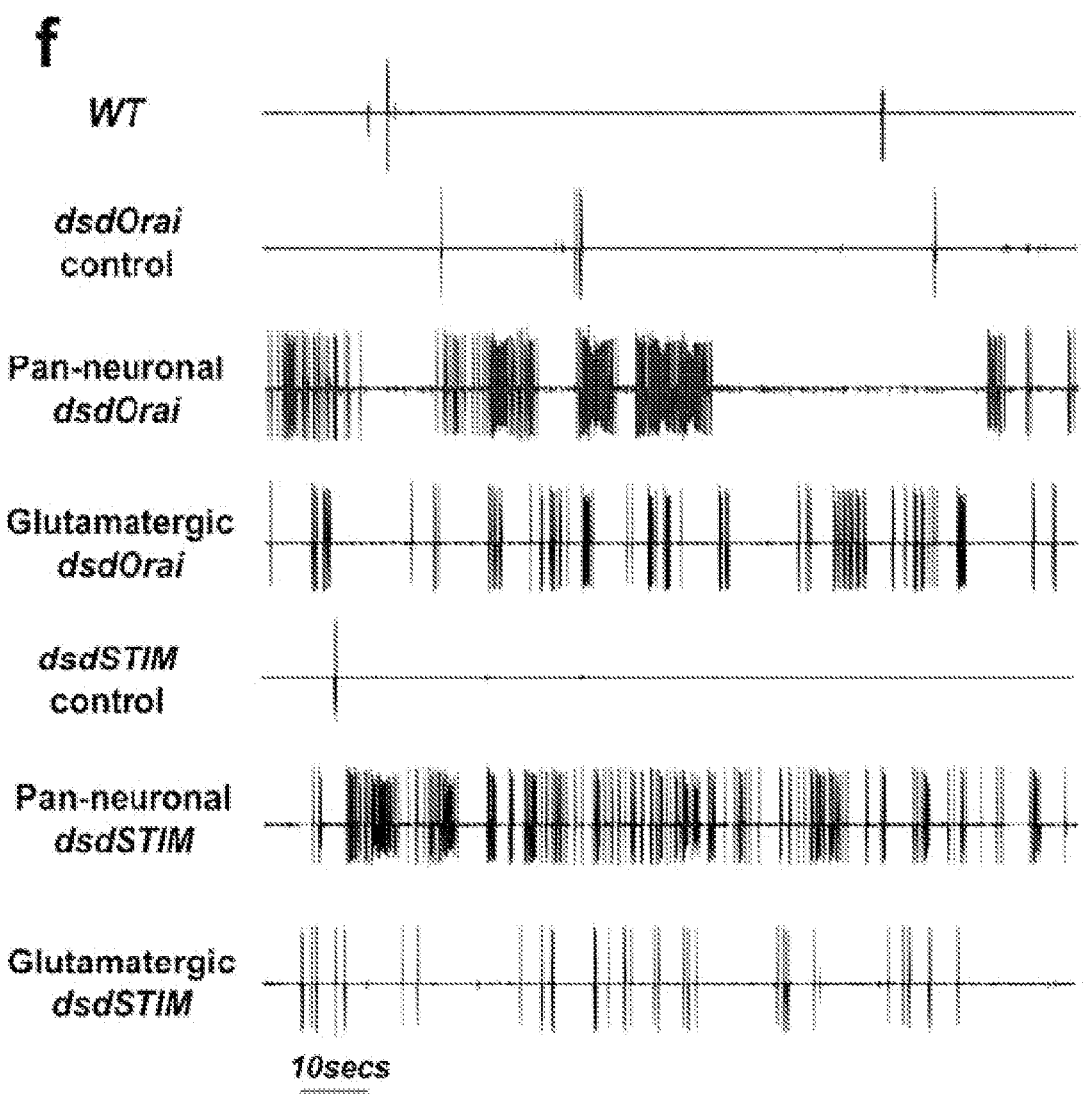

FIG. 2 Illustrative embodiments showing that targeted RNAi knock down of dOrai or dSTIM in subsets of neurons gives rise to flight motor defects:

(a) Pan-neuronal knock-down of dOrai by an inducible RNAi construct induces a mild change in wing posture not seen when it is knocked down in glutamatergic neurons;

(b) Pan-neuronal down-regulation of dSTIM transcripts induces a significant defect in the wing posture not observed when the down-regulation is restricted to glutamatergic neurons;

(c) Targeting dOrai or dSTIM RNAi to all post-mitotic neurons or the glutamatergic subset of neurons introduces significant flight defects (determined using Student's t-test for two populations) as tested by the cylinder drop test. Flight defects observed upon pan neural down regulation of dSTIM are nearly 100% (P=1.01E-8) while down regulation of dOrai results in 60% flies being flight defective (P=1.9E-4). Down regulation of dOrai or dSTIM in glutamatergic neurons results in a flight defect of nearly 40% (*P=0.00246 for dsdOrai). All GAL4 control flies exhibited normal flight. Plotted is the data for glutamatergic GAL4 control. Values are plotted as mean±SE;

(d) dOrai or dSTIM RNAi expression by glutamatergic and pan-neuronal drivers introduces defects in air puff induced flight patterns among the non-fliers selected from the cylinder drop test. Flies with down regulated dOrai and dSTIM were unable to sustain flight beyond 5 s and exhibit arrhythmic flight patterns. The numbers in brackets represent the number of flies exhibiting the characteristic pattern of electrical activity upon air puff stimulation out of the total number of non-fliers tested. Arrow indicates the point of delivery of air puff stimulus;

(e) Significantly higher levels of spontaneous firing, was recorded from the DLMs of flies where dOrai or dSTIM had been knocked down in either all post-mitotic neurons (*P=2.93E-5 for dsdOrai, 0.04354 for dsdSTIM) or only glutamatergic neurons (*P=0.00456 for dsdOrai, 0.543E-4 for dsdSTIM). The GAL4 control refers to glutamatergic GAL4. The pan-neural GAL4 control looked similar. The frequency of spontaneous firing for individual flies in each genotype is also shown (•). Values are plotted as mean±SE and significance is determined using Student's t-test for two populations; and (f) Representative traces of spontaneous firing activity from the DLMs of the indicated genotypes.

Figure 3:
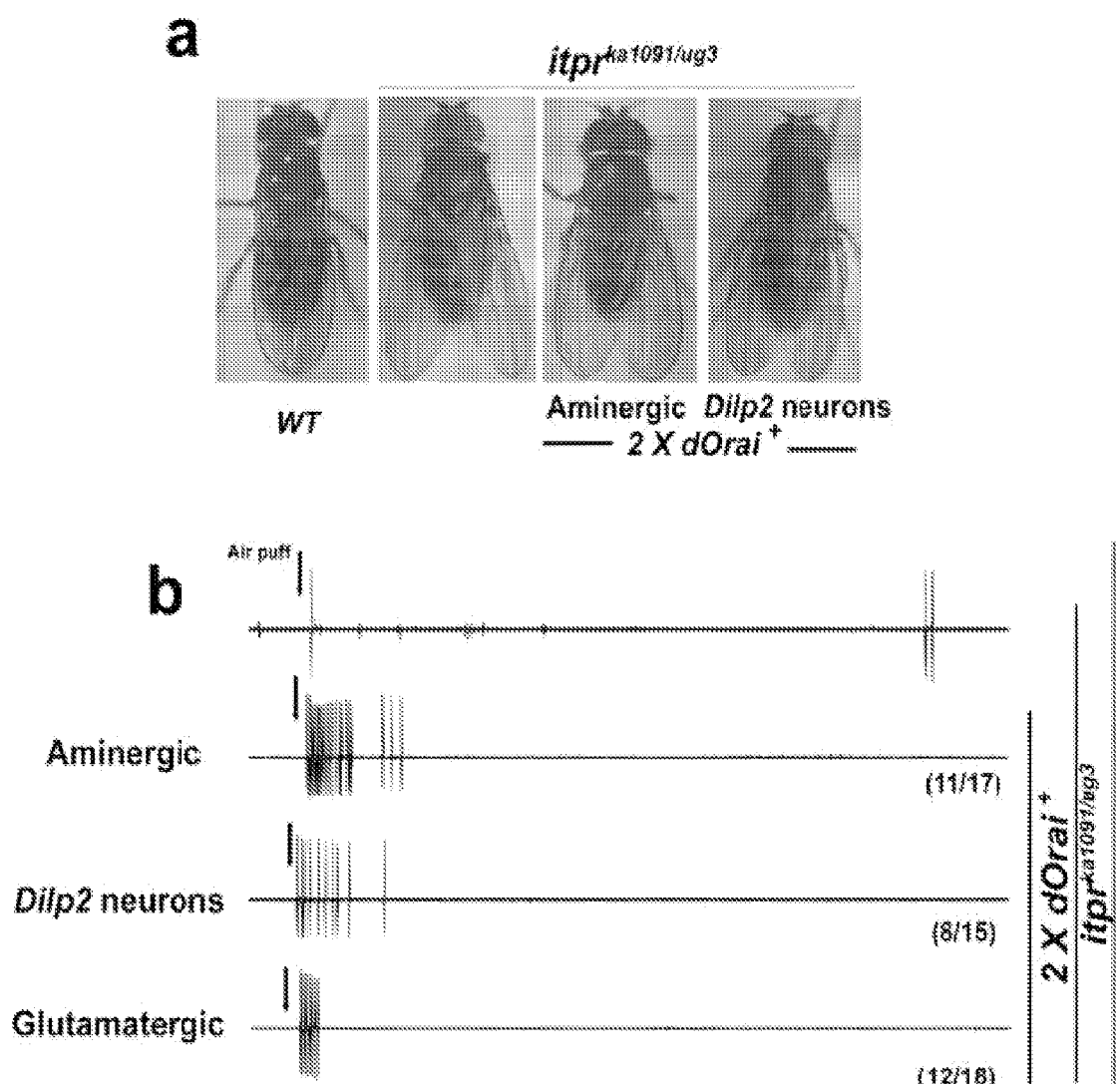
Figure 3:
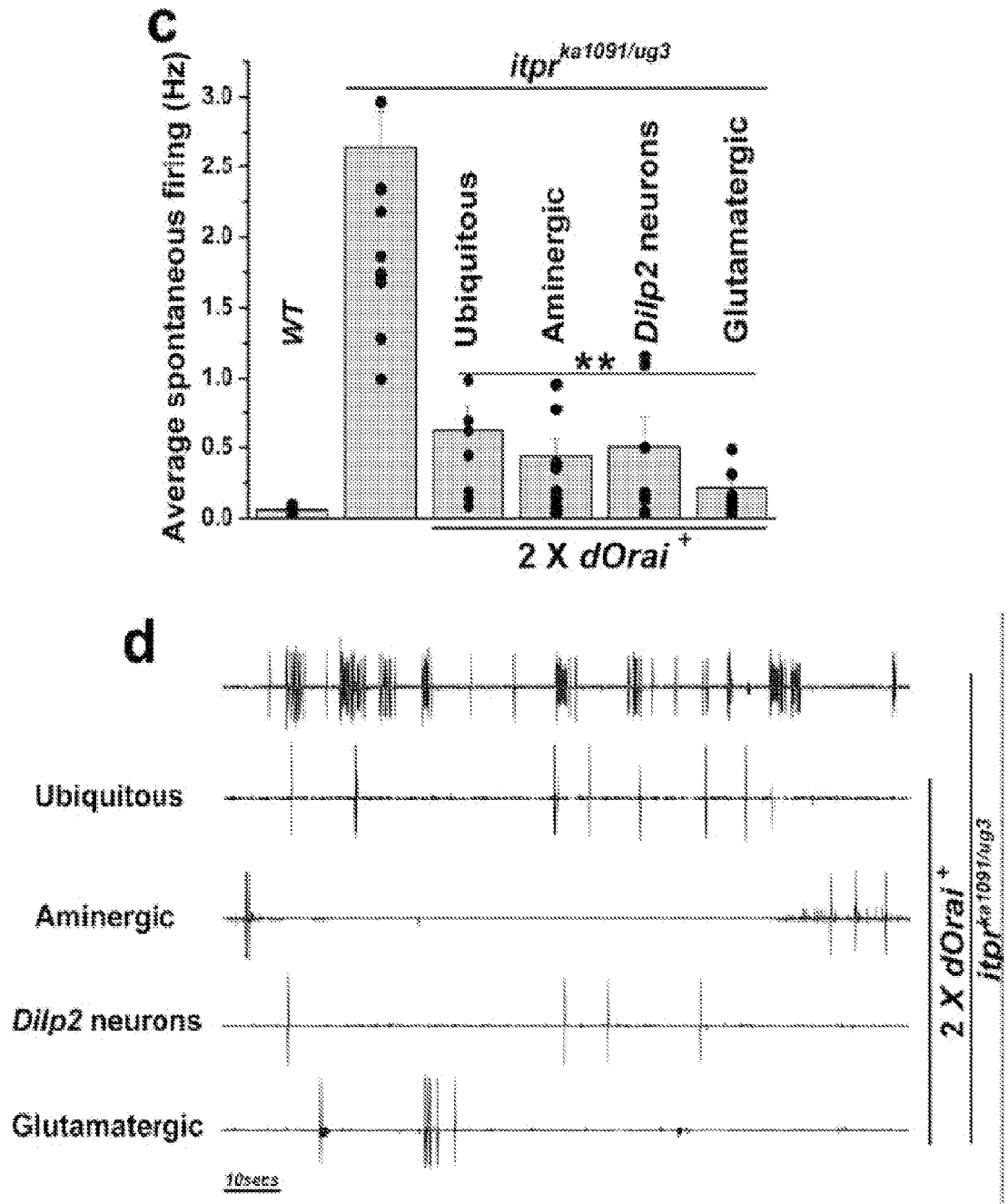
Figure 3:
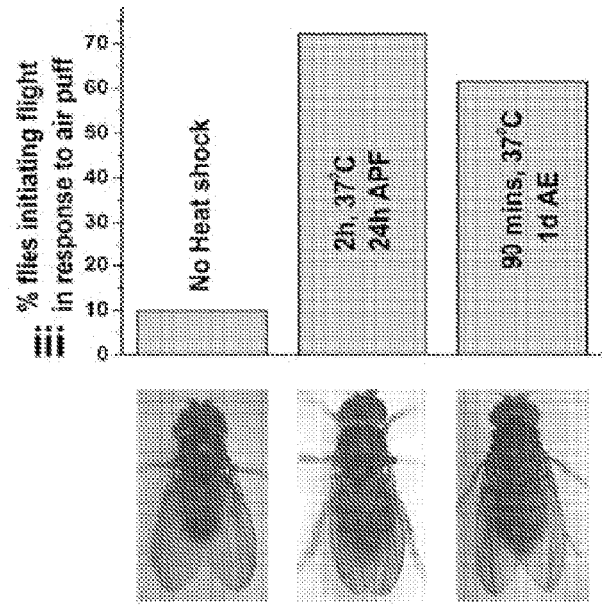
Figure 3:
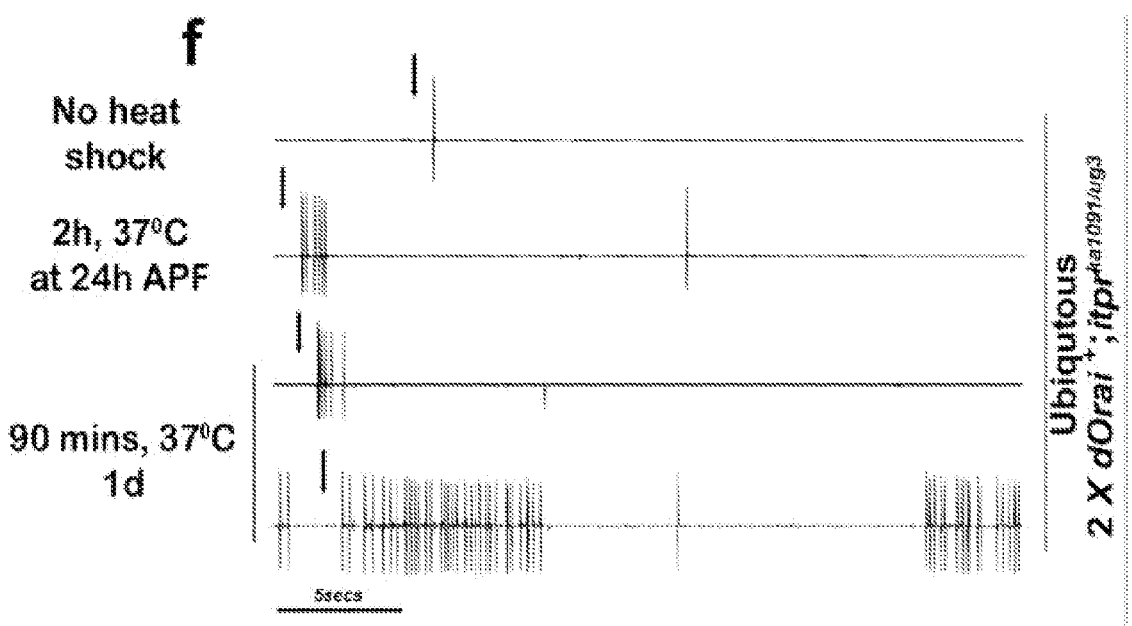

FIG. 3 Illustrative embodiment showing that over-expression of dOrai+ in neuronal subsets causes partial suppression of flight defects in an itpr mutant:

(a) Over-expression of UASdOrai+ in aminergic and Drosophila insulin-like peptide 2 (Dilp2) producing neurons in itprku partially suppresses the characteristic wing posture defect of itprku;

(b) Air-puff stimulus elicits flight patterns in itprku flies over-expressing dOrai+ in aminergic, glutamatergic and dILP-2 producing cells; flight patterns are not sustained beyond 5 s. Arrows indicate the point of delivery of an air puff stimulus;

(c) Ubiquitous over-expression of dOrai+ (two copies) by a leaky heat-shock (hs) GAL4 at 25° C. or in sub-neuronal domains suppresses the spontaneous firing of itprku flies (**P=0.00082 using hs GAL4, 0.00133 in aminergic cells, 5.54E-6 in Dilp2 cells and 2.02E-6 when expressed in the glutamatergic domain; significance is determined by the Student's t-test). Histograms represent mean values of spontaneous firing frequency while the error bars represent SE;

(d) Cell type specific suppression of neural hyperactivity is seen when dOrai+ is over expressed using aminergic, glutamatergic and Dilp2 GAL4s in the genetic background of itprku;

(e) Delivery of a heat-shock to either 24 hr pupae or 1 day old adults expressing 2 copies of dOrai+ under the ubiquitous heat-shock promoter in itprku, enables flies to initiate arrhythmic flight patterns in response to an air puff stimulus. In the absence of a heat-shock flight initiation is not observed. Heat shock induced ubiquitous expression of dOrai+ also results in partial suppression of the wing posture defect in itprku; and (f) Representative traces of flight patterns from DLMs after delivery of an air puff stimulus (arrow).

Figure 4:
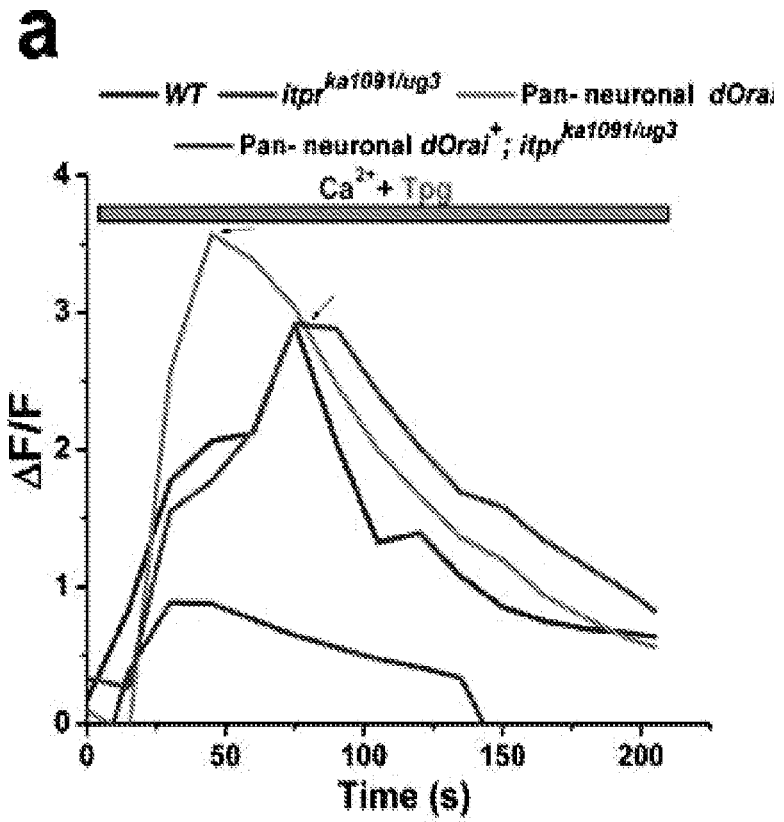
Figure 4:
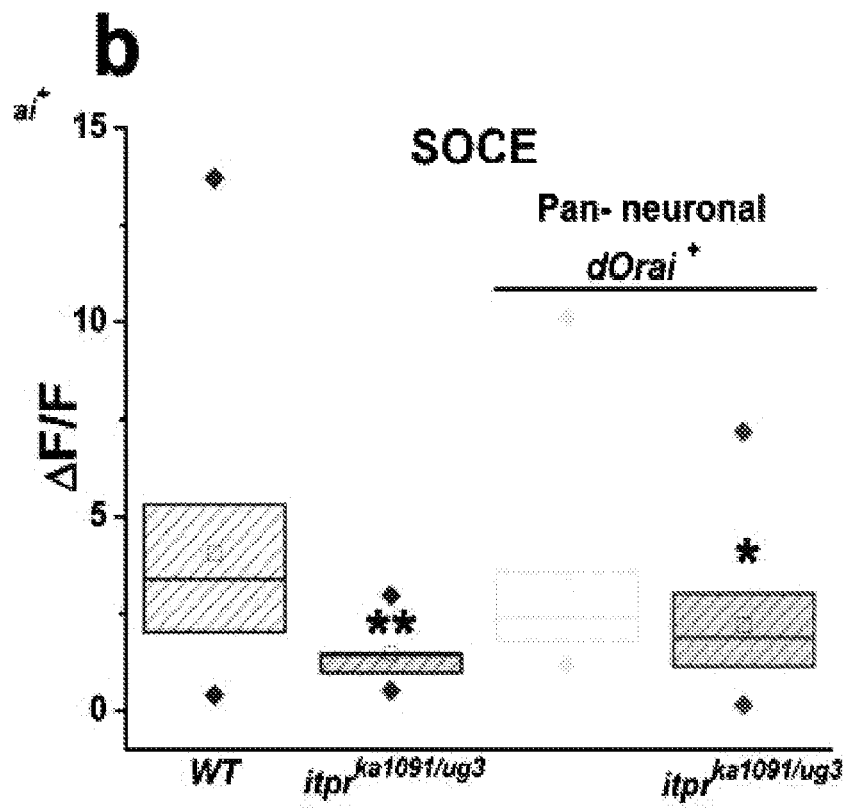
Figure 4:
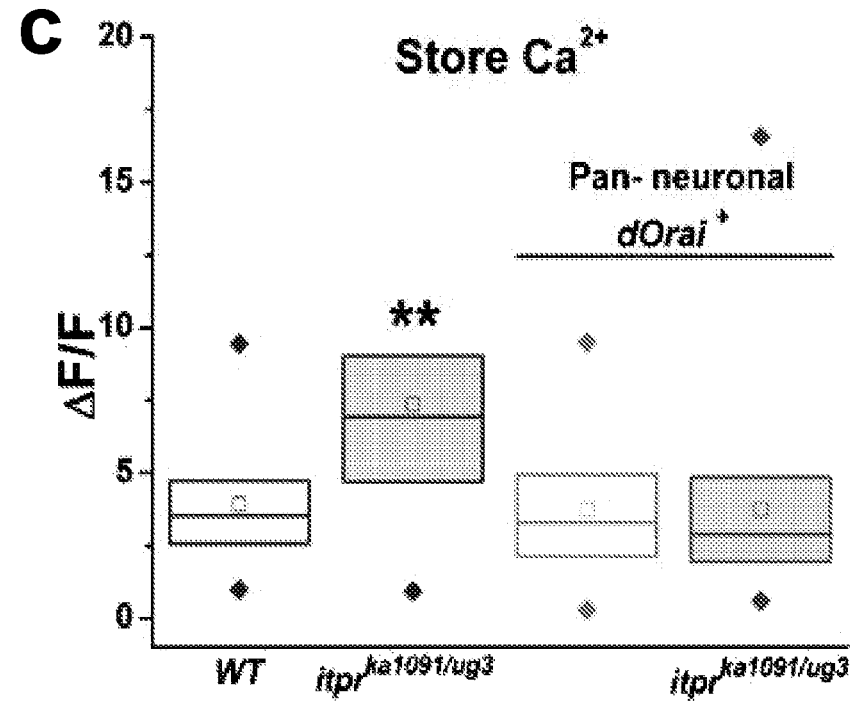
Figure 4:
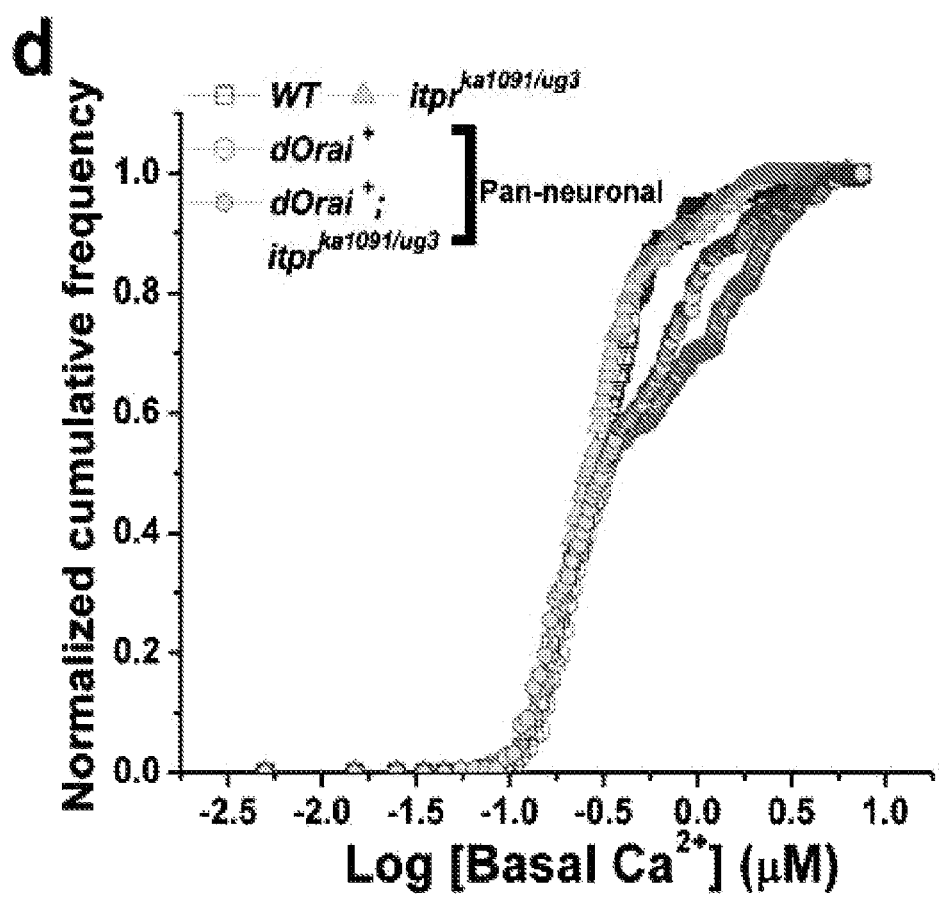
Figure 4:
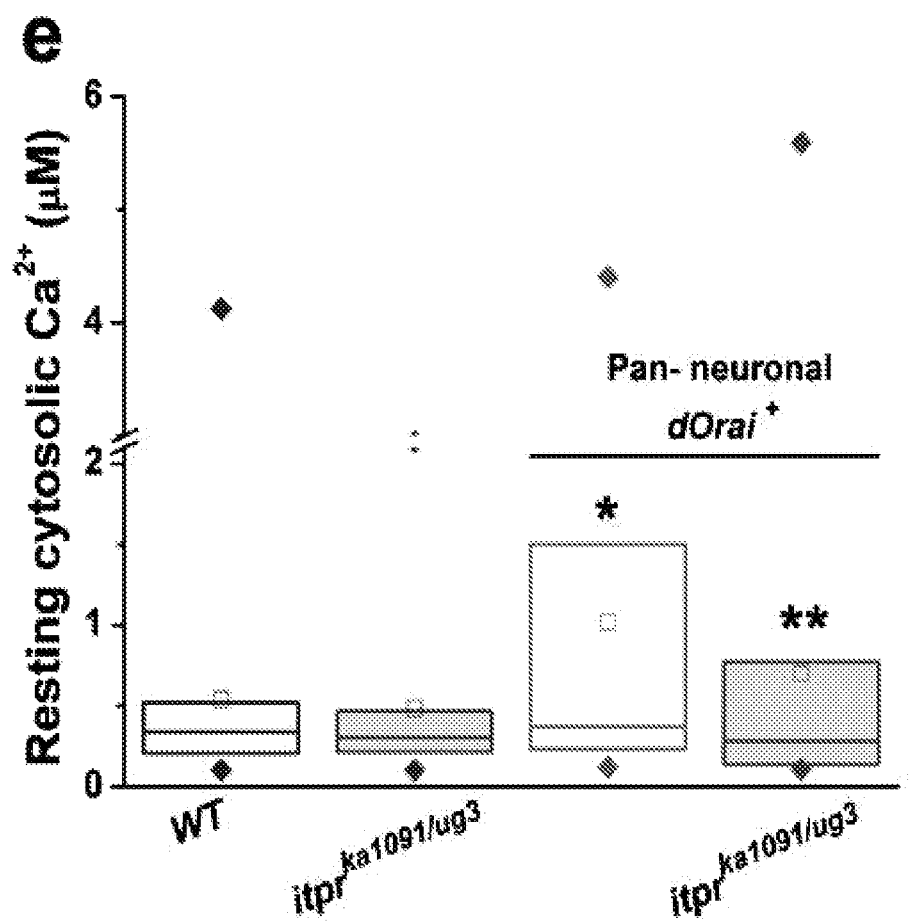

FIG. 4 Illustrative embodiments showing dOrai+ over-expression in itprku neurons restores intracellular $Ca^{2+}$ homeostasis:

(a) Single cell traces of SOCE by $Ca^{2+}$ add-back after store depletion with thapsigargin (Tpg). Arrows represent the peak values of response which has been plotted as a box chart in FIG. 4b;

(b) SOCE was measured by $Ca^{2+}$ add-back experiments. In neurons over-expressing dOrai+ in itprku, SOCE is significantly higher than itprku (*PANOVA=0.00209 compared to itprku); it is not altered when dOrai+ is expressed on its own. Pan-neural expression was achieved using ElavC155GAL4 strain;

(c) Box plot representing ER store $Ca^{2+}$ levels in neurons of the indicated genotypes. $[Ca2+]ER$ in itprku neurons is significantly greater than wild-type (**PANOVA=5.551E-6). Pan-neuronal over-expression of dOrai+ restores normal $[Ca2+]ER$ to itprku. Store $Ca^{2+}$ in cells over-expressing dOrai+ is similar to WT;

(d) K-S plot analyzing the distribution of intracellular $Ca^{2+}$ in neurons of indicated genotypes. A greater frequency of cells with higher $[Ca2+]i$ is seen in genotypes expressing dOrai+ (PK-S=0.0011); and (e) Box plot analysis of resting cytosolic $Ca^{2+}$ in neurons with over-expression of $dOrai^+$. The average basal $Ca^{2+}$ in cells over-expressing dOrai+ with or without itprku in the background is significantly higher (*PANOVA=0.04621 and 0.0095 respectively) than in WT. Mean resting cytosolic $Ca^{2+}$ in neurons of itprku is similar to WT 170 or more cells were analyzed for each genotype in every experiment.

Figure 5:
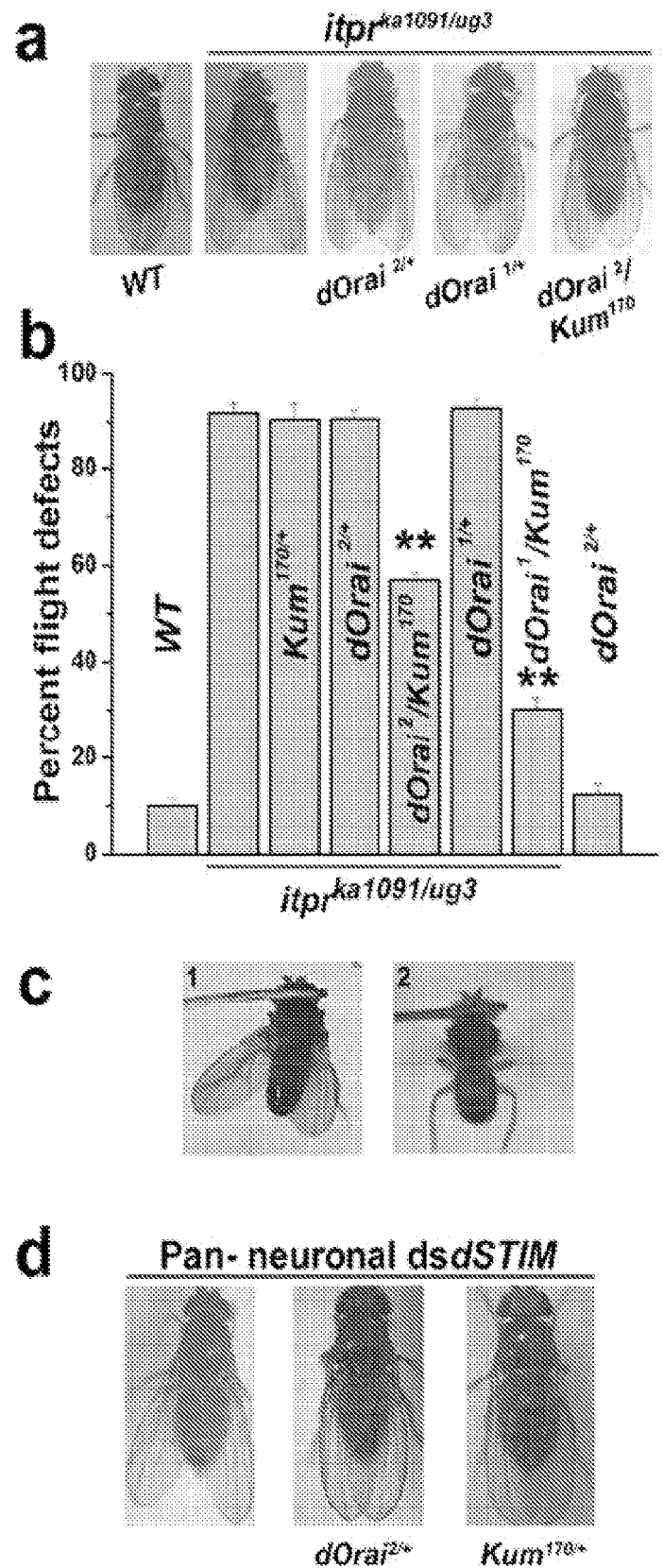
Figure 5:
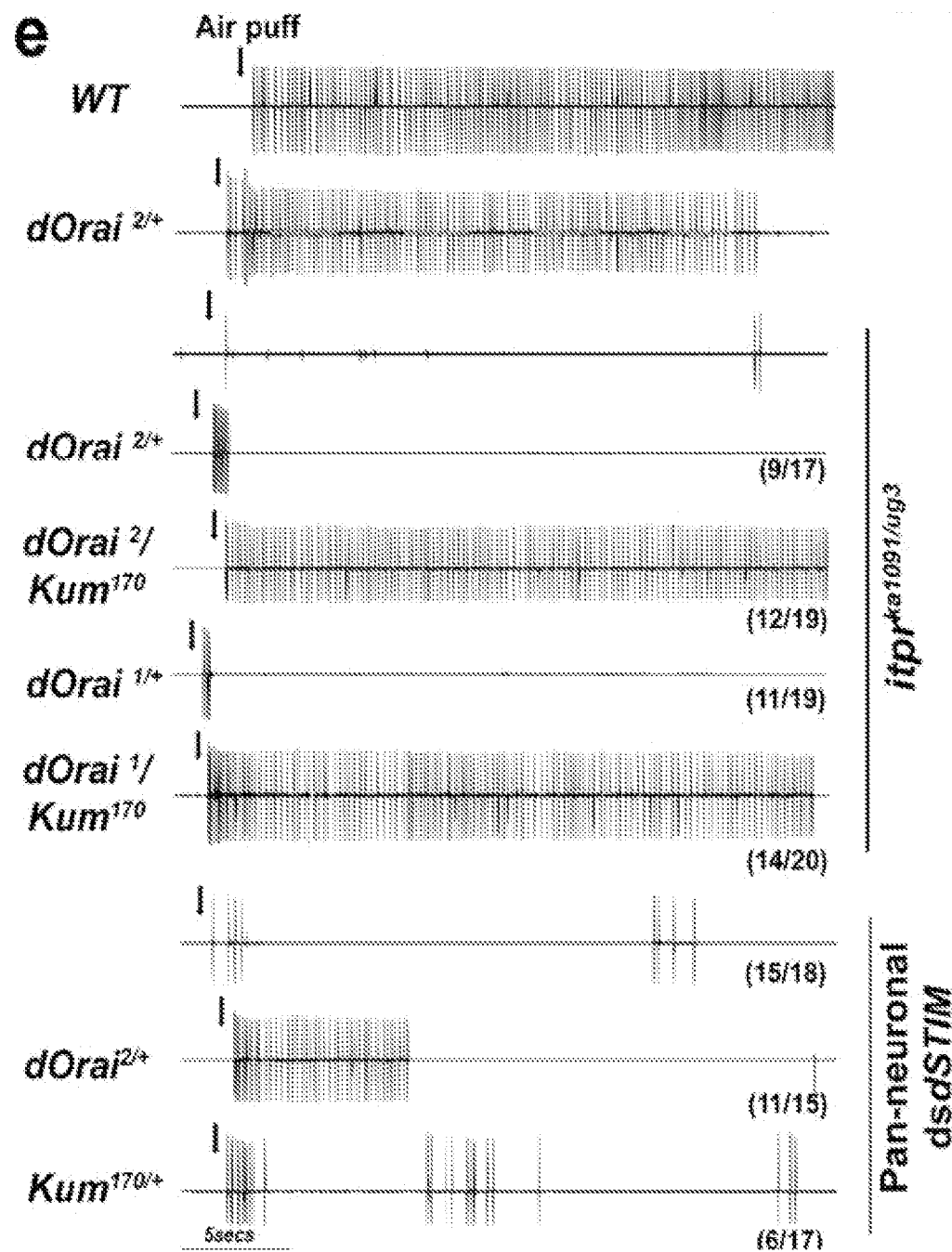
Figure 5:
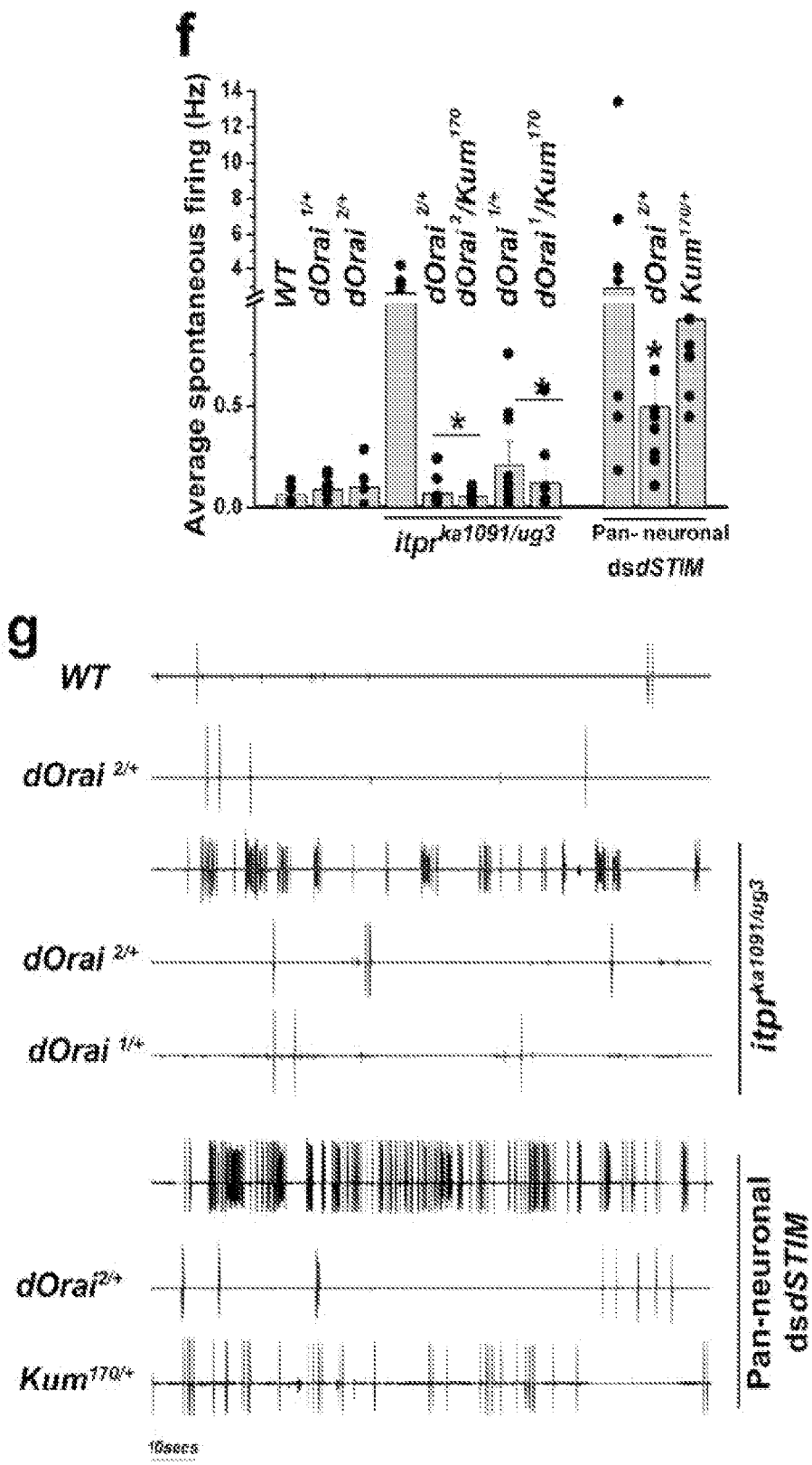

FIG. 5 Illustrative embodiments showing flight and associated physiological defects are suppressed in a combination of dOrai, dSERCA and itpr mutants:

(a) Wing posture defect of itprku is partially suppressed in dOrai2/+; itprku and dOrai1/+; itprku flies grown at 25° C. Triple mutants of Kum170/dOrai2; itprku show better suppression of wing posture defect than the double mutants;

(b) Flight defect of itprku is neither suppressed by dOrai mutants (dOrai1 or dOrai2) nor Kum170/+ (90-95% defect as assayed by the cylinder drop test, *P=0.00529 compared to W7). A double mutant rescue of itprku with Kum170 and dOrai2 or dOrai1 suppresses the flight defect to 60% (**P=4.91E-6 in presence of dOrai1 and 5.61E-4 in presence of dOrai2, compared to itprku). Marginally greater suppression is achieved with dOrai1 than with dOrai2. Histograms represent the mean±SE; significance was tested by the Students t-test for two populations;

(c) Snapshots taken within first 5 s of air puff induced flight initiation in 1, itprku; 2, Kum170/dOrai2; itprku;

(d) Defects in wing-posture induced by pan-neuronal knock down of dSTIM are suppressed differentially by a single copy of dOrai2 or Kum170. While nearly 50% of flies with dOrai2/+ in the background of lowered dSTIM levels exhibit normal wings, suppression by Kum170/+ is observed for only 10% of the flies;

(e) Air puff stimulus elicits brief (<5 s) rhythmic flight patterns from the DLMs of dOrai2/+; itprku and dOrai1/+; itprku similar to Kum170/+; itprku but not from DLMs of itpr mutants alone. The action potentials generated in 9 out of 17 flies tested for dOrai2/+; itprku and 11 out of 19 flies tested for dOrai1/+; itprku tested are rhythmic, accompanied by wing beating which terminated within 5 s of initiation. Triple mutant fliers of Kum170/dOrai2; itprku initiate sustainable rhythmic flight patterns similar to WT which last for a minimum time of 30 seconds. Similar air puff induced flight patterns are seen in recordings from flies of Kum170/dOrai1; itprku. A single copy of dOrai2 also restores rhythmic flight initiation in a majority of flies with pan-neuronal RNAi knock-down of dSTIM. Arrows indicate the point of air puff delivery;

(f) Spontaneous hyperactivity in DLMs of itprku is suppressed by the presence of a single copy of either dOrai1/+ or dOrai2/+ or the combined presence of Kum170/dOrai2 (*P=9.26E-6, 1.03E-3 and 1.94E-4 respectively, compared to itprku). High spontaneous firing rates induced by pan-neuronal dsdSTIM expression are also suppressed by dOrai2/+ (*P=0.03537). Recordings were obtained from at least 15 flies of every genotype and the data plotted as mean±SE. Individual data points have been included to indicate the spread; and (g) Representative traces of spontaneous firing activity from the DLMs of the indicated genotypes. A single copy of a dOrai hypermorphic allele can suppress spontaneous firing DLMs from of itprku and pan-neuronal dsdSTIM (ElavC155GAL4; UASdsdSTIM) adults.

Figure 6:
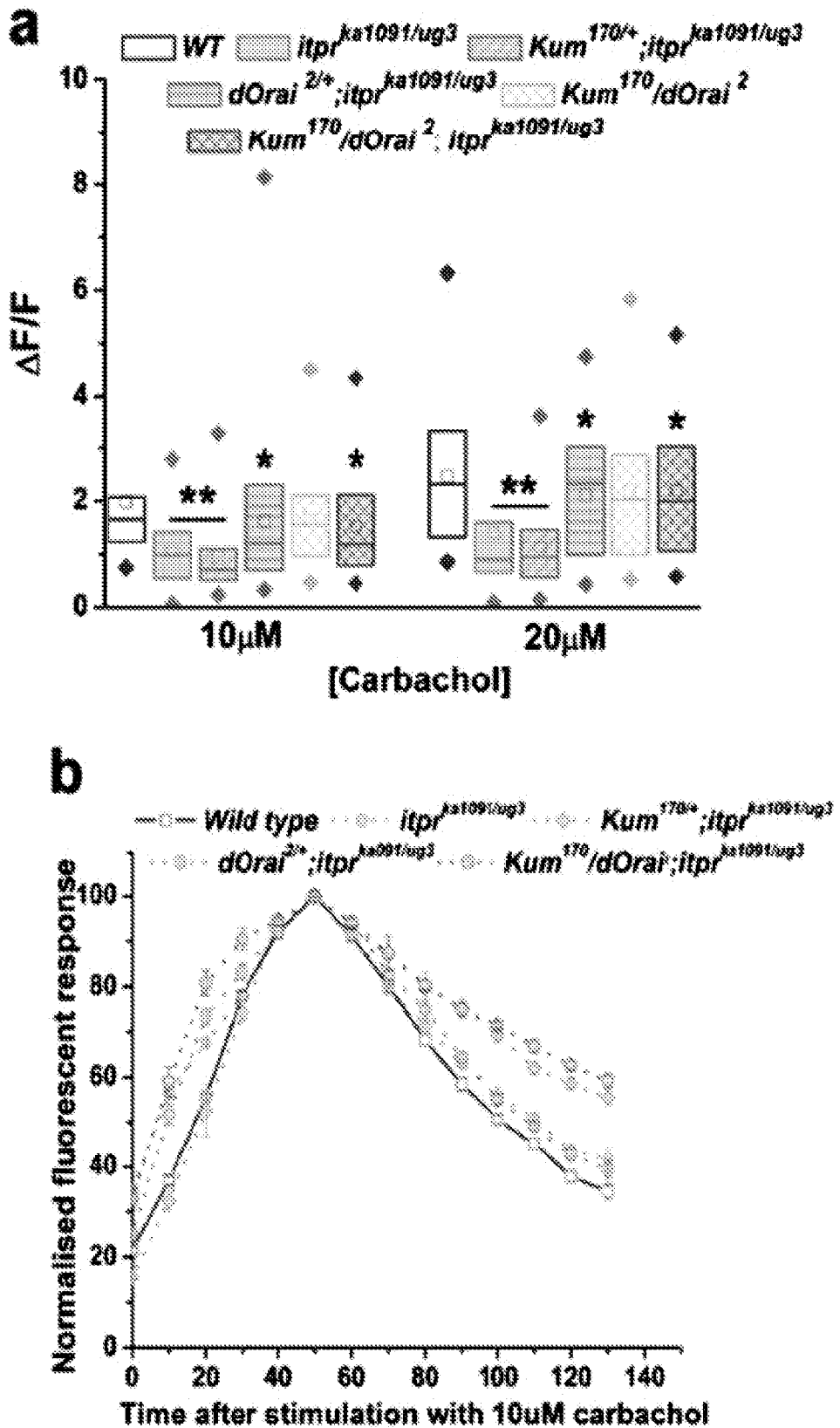
Figure 6:
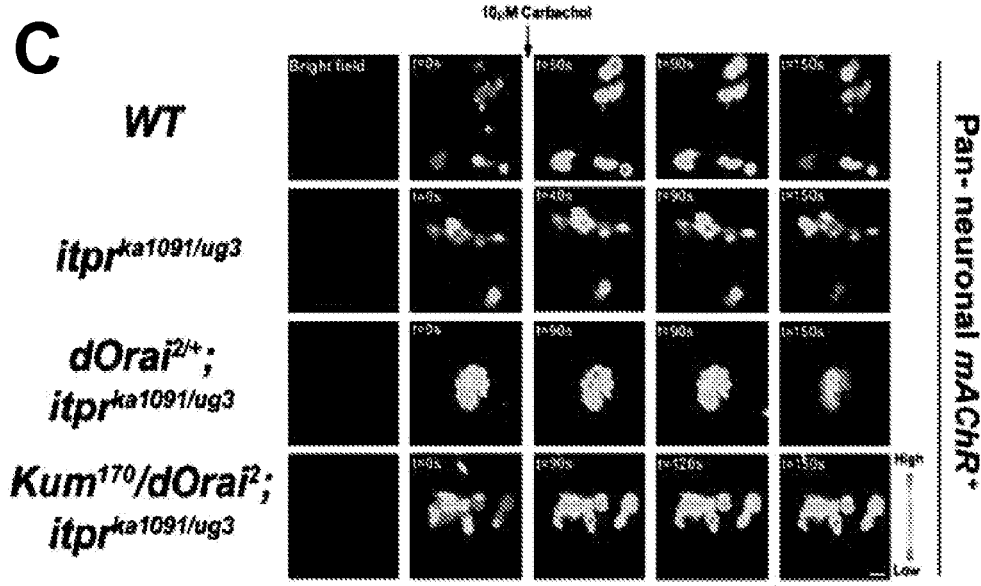
Figure 6:
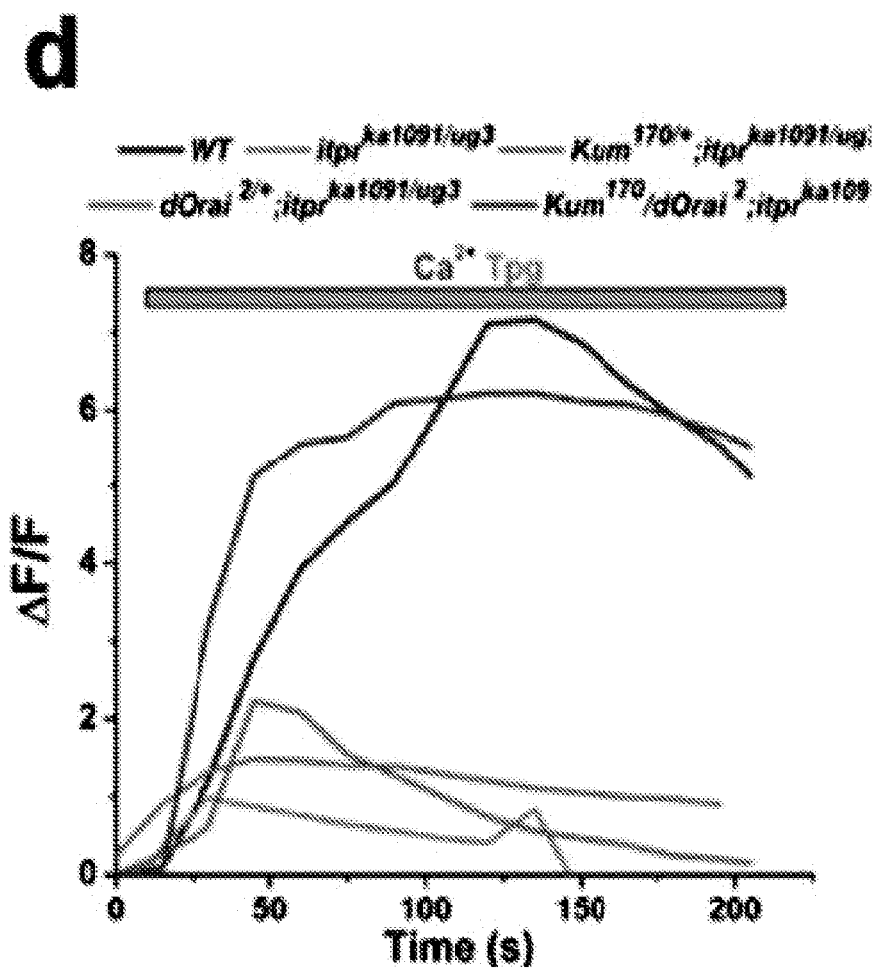
Figure 6:
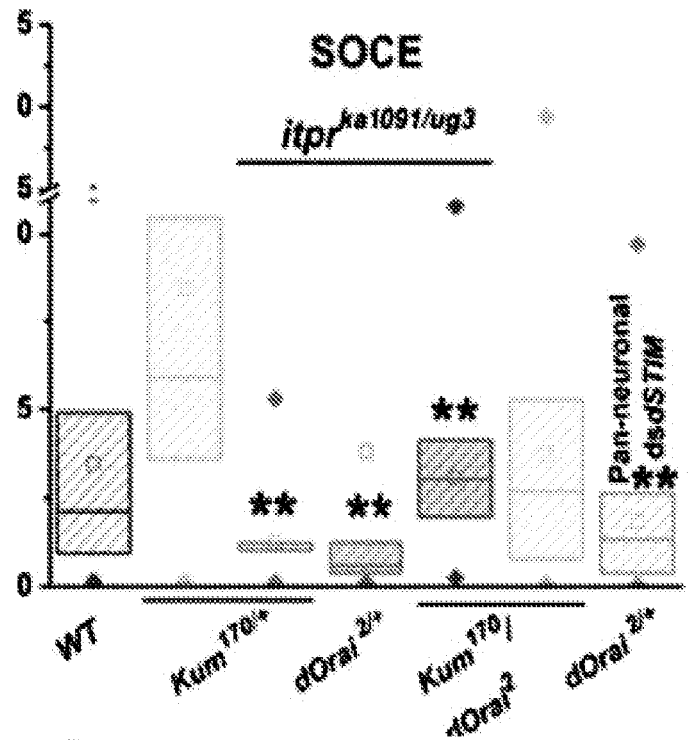
Figure 6:
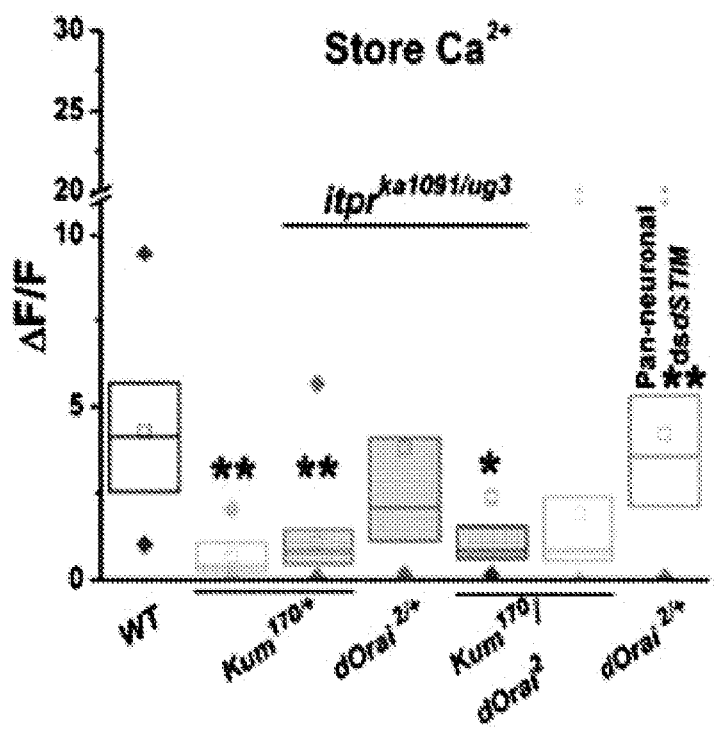

FIG. 6 Illustrative embodiments showing dOrai and dSERCA mutants alter different aspects of intracellular $Ca^{2+}$ release in *Drosophila* neurons:

(a) Changes in stimulated $Ca^{2+}$ release through the InsP3R (measured as ΔF/F) in itprku alone and in double and triple mutants of itprku, Kum170 and dOrai2 is shown in response to 10 μM and 20 μM carbachol. Carbachol responses from all neurons were obtained by pan-neuronal expression of the *Drosophila* muscarinic acetylcholine receptor (ElavC155GAL4; UASdmAchR) and loading with Fluo-4. Release through the InsP3R is significantly compromised in itprku (PANOVA=5.76E-5 compared to WT for 10 μM carbachol stimulation) and is similar in Kum170/+; itprku (PANOVA=3.84E-6 compared to WT) Presence of dOrai2 in itprku background restores InsP3 stimulated $Ca^{2+}$ release to WT levels with or without Kum170 (*PANOVA=6.56E-4 compared to itprku). Results plotted here are observations from 150 or more cells;

(b) Effect of Kum170 and dOrai2 on perdurance of InsP3-mediated $Ca^{2+}$-release signals. Presence of a single copy of Kum170 alone or in double or triple mutant combination with dOrai2 or itprku significantly delays the rate of cytoplasmic Ca²⁺ clearance after carbachol stimulated Ca²⁺-release. Approximately 40-50 cells of each genotype, with similar peak response times were selected for this analysis. Ca²⁺ clearance time in itpr mutants alone or in combination with dOrai mutants is similar to WT.

(c) Ca²⁺ release through InsP3R is significantly compromised in itprku and is restored back in double mutants of itprku and dOrai2. Images were pseudo-colored to represent [Ca²⁺]i. Larval neurons from WT, itprku and dOrai2; itprku expressing mAChR were stimulated with 10 µM carbachol and fluorescent images were taken in the time lapse mode. The arrow represents addition of 10 µM carbachol. The scale bar represents 10 µm. Warmer colors represent higher Ca²⁺;

(d) Single cell traces of SOCE by Ca²⁺ add back after store depletion by thapsigargin;

(e) SOCE was measured by Ca²⁺ add-back experiments in cells derived from larval brains of Kum170 and dOrai2 in the genetic background of itprku. SOCE in neurons derived from Kum170; itprku brains remains low (**PANOVA=2.04E-4 compared to WT) reminiscent of itprku and unlike cells isolated from Kum1704 organisms, where it is significantly higher than WT (*PANOVA=8.11E-6). The proportion of cells with detectable SOCE in neurons from Kum170; itprku brains is 70%. SOCE remains low in dOrai2/+; itprku, though the proportion of cells with detectable SOCE in neurons of this genotype is restored to 65%. SOCE is restored in triple mutants of Kum170/dOrai2; itprku (PANOVA=0.00667 compared to itprku). Heterozygous dOrai2/+ partially restores SOCE in neurons in which dSTIM is down-regulated by RNAi (PANOVA=0.00324 compared to pan-neuronal dsdSTIM); and (f) Box plots representing [Ca²⁺]ER levels of neuronal cells of the indicated genotypes. Double mutants of Kum170 and itprku have significantly reduced levels of store Ca²⁺ (**PANOVA=0.00011 compared to WT); dOrai2/+ restores store Ca²⁺ levels in double mutants (dOrai2/+; itprku, *PANOVA=4.73E-6 compared to itprku) but not in triple mutants (dOrai2/Kum170; itprku; PANOVA=0.03204 compared to WT). Presence of a single copy of dOrai2 restores [Ca²⁺]ER in neurons in which dSTIM is transcriptionally down-regulated by pan-neuronal expression of dsdSTIM (**PANOVA=3.34E-6) compared to pan-neuronal dsdSTIM alone).

Figure 7:
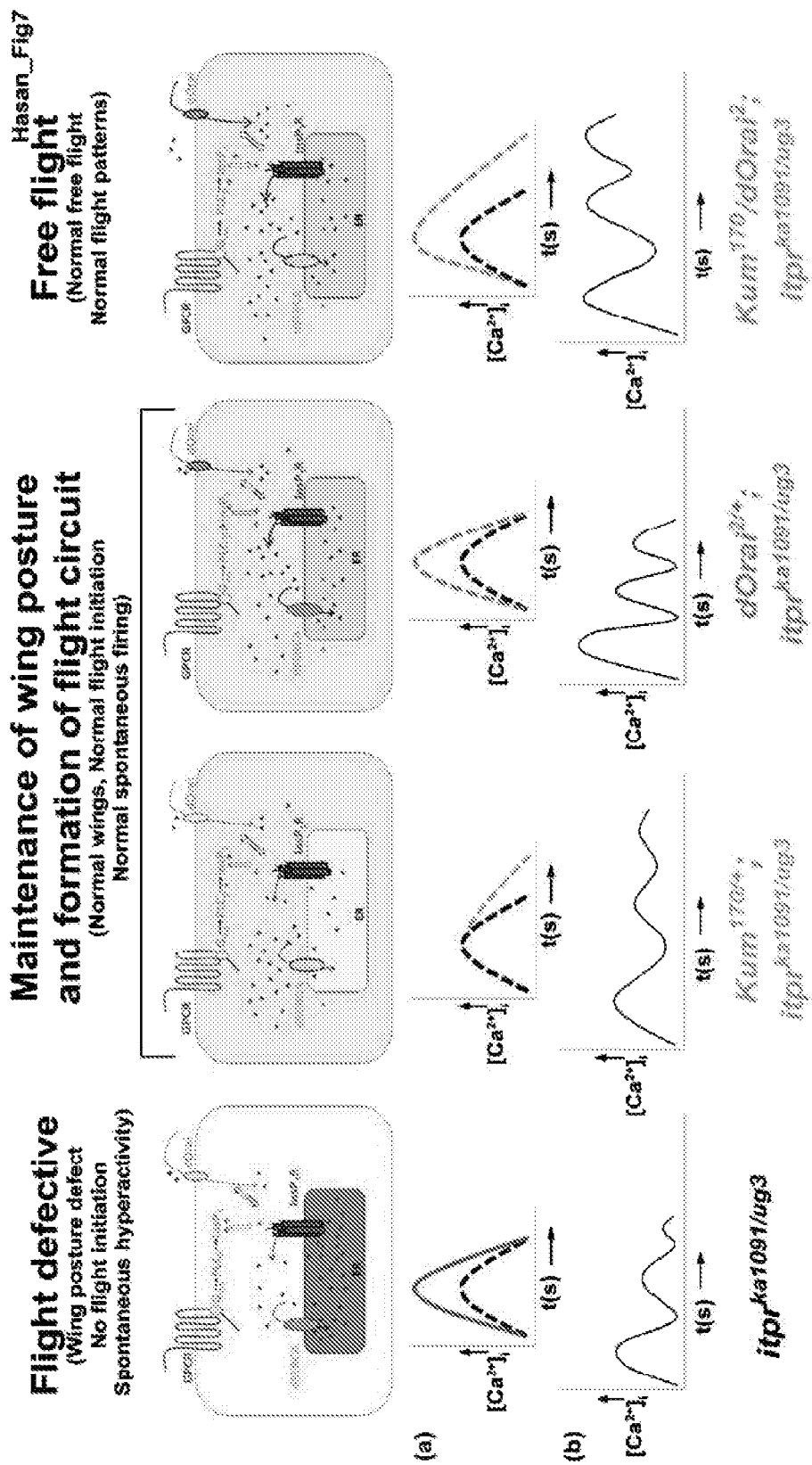

FIG. 7 Model of InsP3-mediated intracellular Ca²⁺ signals in itprku mutant neurons and their modulation by Orai and SERCA in the context of *Drosophila* flight Illustrative embodiments of the model showing changes in cytosolic Ca²⁺ generated by stimulating hypomorphic InsP3Rs in single, double and triple mutant conditions. Warmer colors denote higher concentration of Ca²⁺ in the ER store or cytoplasm. Panel (a) Changes to a single response peak; the black dotted trace represents itprku and other dotted traces represent the indicated double and triple mutant genotypes; response of the wild type InsP3R is represented by a solid brown trace. Panel (b) Changes over longer times showing the amplitude and duration of Ca²⁺ transients upon repeated stimulations of the InsP3R which would be subject to ER store refilling by SOCE. The recurring Ca²⁺ wave shown in (b) has not been demonstrated experimentally in our conditions.

Figure 8:
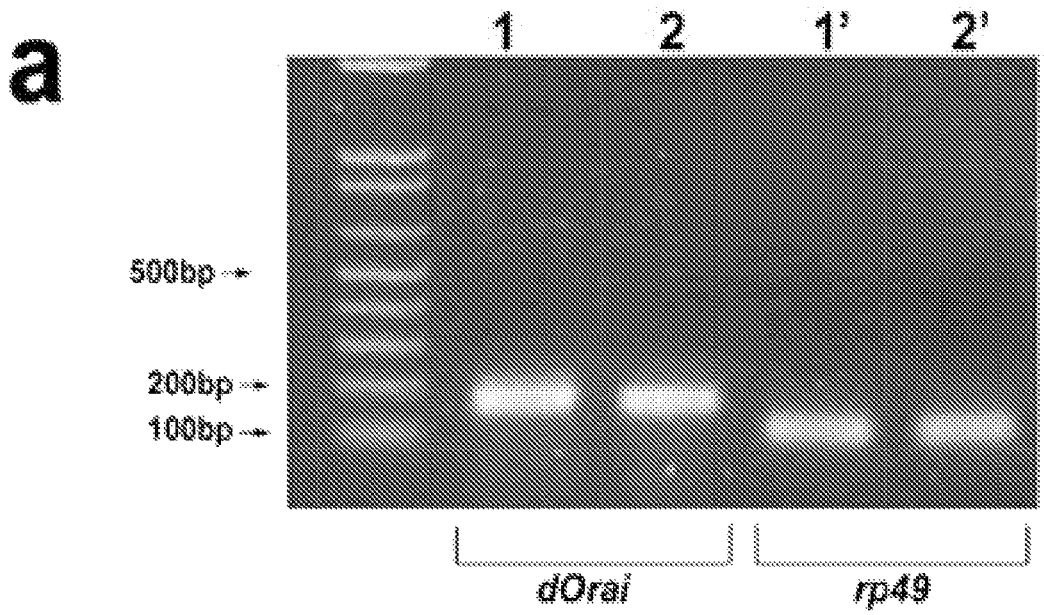
Figure 8:
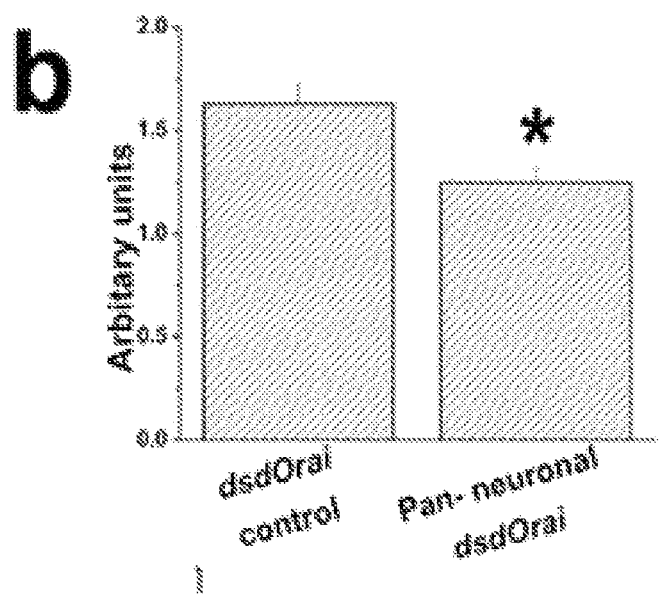
Figure 8:
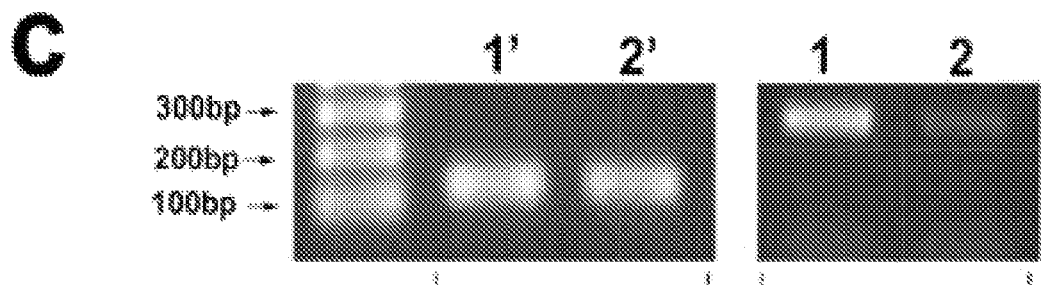
Figure 8:
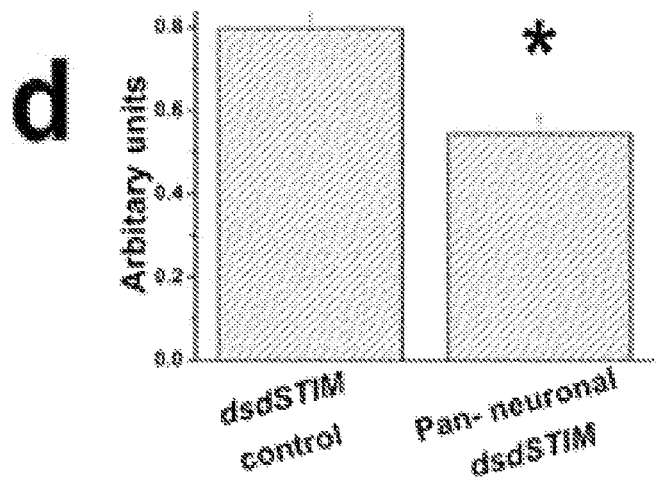
Figure 8:
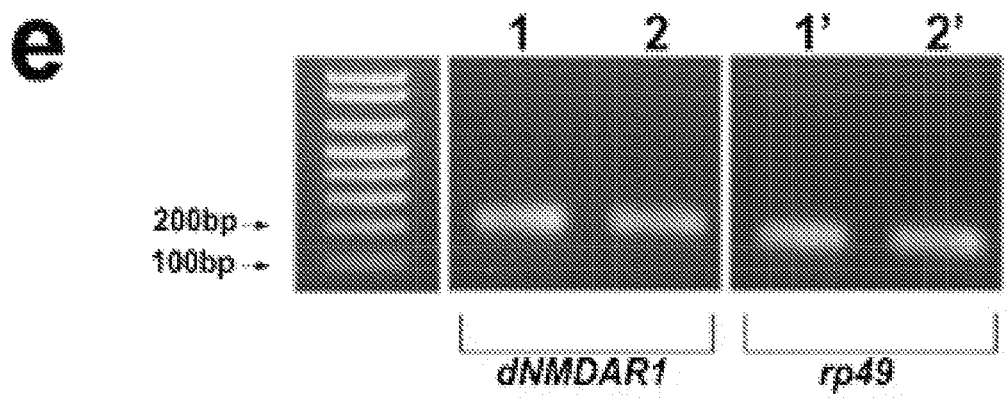
Figure 8:
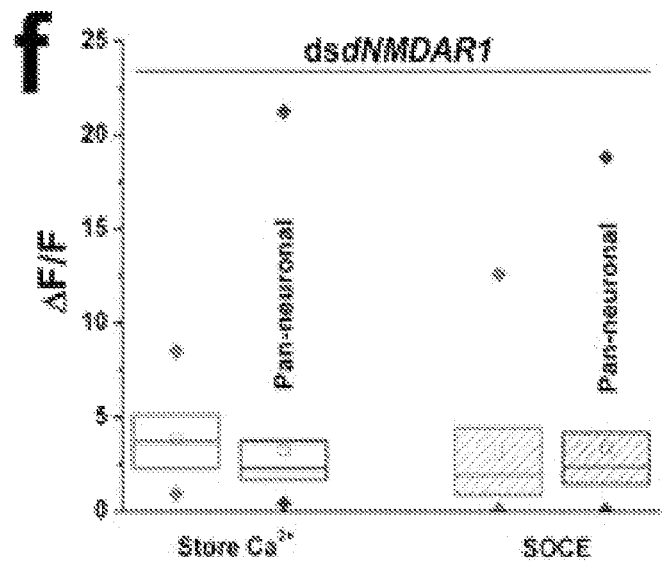

FIG. 8 Illustrative embodiments showing targeted down regulation of dOrai and dSTIM in neurons:

(a) Targeted expression of UASdOraiRNAi$^{221/+}$ to post-mitotic neurons results in a consistently reduction in the level of dOrai transcripts. RT-PCR for dOrai (173 bp) was done on total RNA isolated from 24 hr pupae and normalized to levels of rp49 transcripts (120 bp). Lanes 1 and 2 contain PCR products for dOrai and lanes 1' and 2' contain PCR products for rp49. Lanes 1, 1' are UASdOraiRNAP$^{221/+}$, lanes 2, 2' are Elav$^{C155}$GAL4; UASdOraiRNAi$^{221}$.

(b) Quantification of dOrai transcript levels normalized to rp49 transcript levels calculated from RT-PCR products obtained from three different batches of RNA. The ratio of fluorescence intensity of each PCR product was estimated using Image J software (NIH, USA). The intensity of the dOrai band was normalized to that of the rp49 band. dOrai transcript levels in UASdOraiRNAi$^{221/+}$ (1.63±0.103) were significantly higher as compared to Elav$^{C155}$GAL4; UASdOraiRNAi$^{221/+}$ (1.25±0.073) (*P=0.03978 as determined by the Student's t-test);

(c) Targeted expression of UASdSTIMRNAf$^{073/+}$ to post-mitotic neurons results in a significant reduction in dSTIM transcript levels (312 bp) as assayed by RT-PCR. Total RNA was isolated from 3$^{rd}$ instar larval brains of UASdSTIMRNAI-$^{073/+}$ (1, 1') and Elav$^{C155}$GAL4; UASdSTIMiRNAi$^{073}$ (2, 2') organisms;

(d) Down-regulation of dSTIM transcript levels by RNAi was determined by measuring the ratio of fluorescence intensity of the dSTIM products to the rp49 products. The ratio measures 0.54±0.05 as compared to 0.79±0.04 of controls (*P=0.01725 calculated by the Student's t-test);

(e) Down-regulation of transcripts of dNR1 in RNA extracted from 3$^{rd}$ instar larvae ubiquitously expressing UASdNR1RNAi$^{333/+}$ under a heat-shock promoter. Total RNA was isolated 24 hrs post heat shock, and RT-PCR carried out for dNR1 (154 bp) and rp49 mRNA. Lanes 1, 1' are heterozygous controls with UASdNR1RNAi$^{333/+}$, lanes 2, 2' are hsGAL4; UASdNR1RNAi$^{333}$; and (f) [Ca²⁺]$_{ER}$ in neurons from larvae with pan neural expression of dsdNR1 is similar to that in neurons of heterozygous dsdNR1 controls. Pan-neuronal knockdown of dNR1 does not alter the SOCE in neurons following store depletion.

Figure 9:
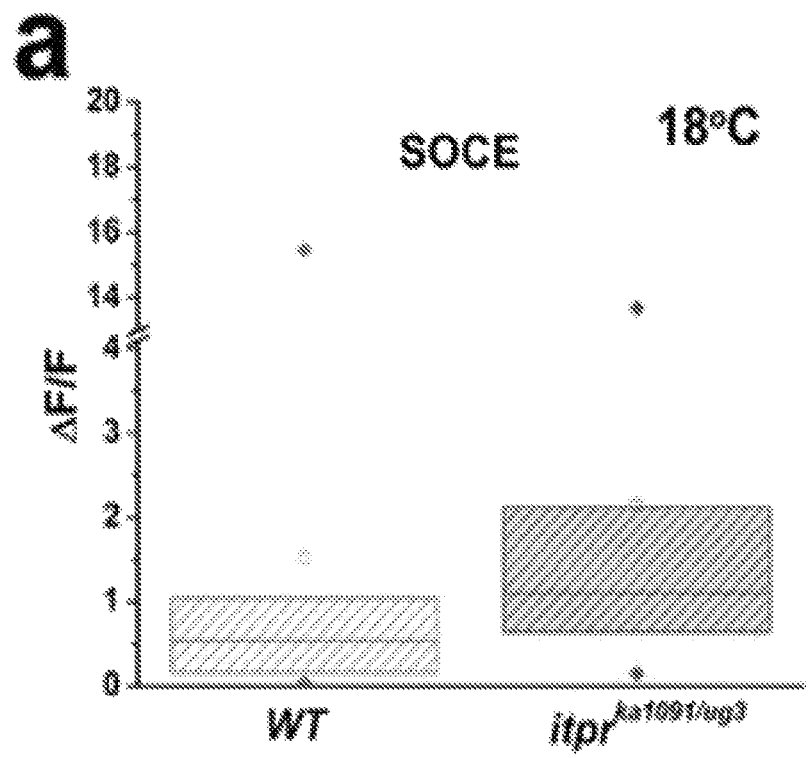
Figure 9:
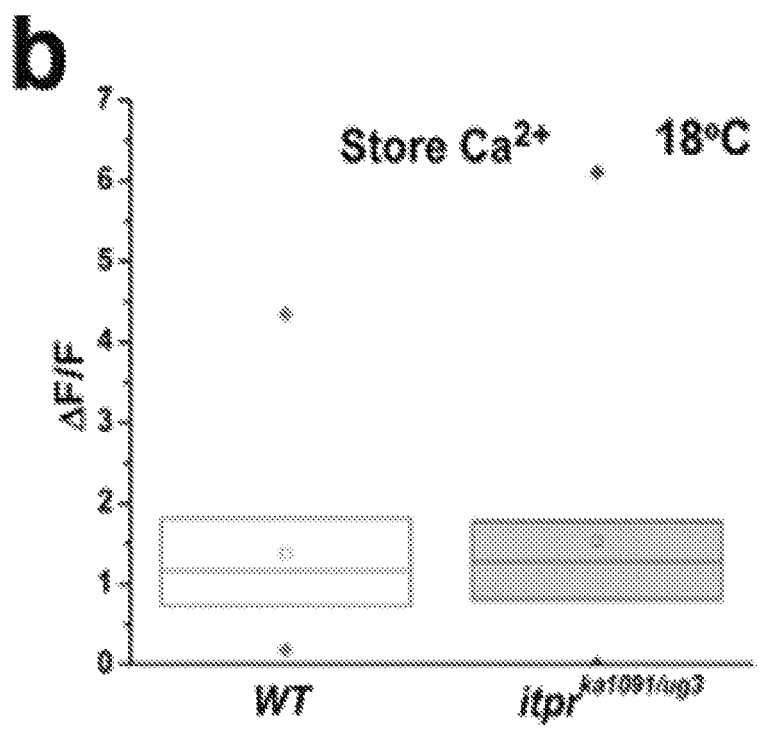
Figure 9:
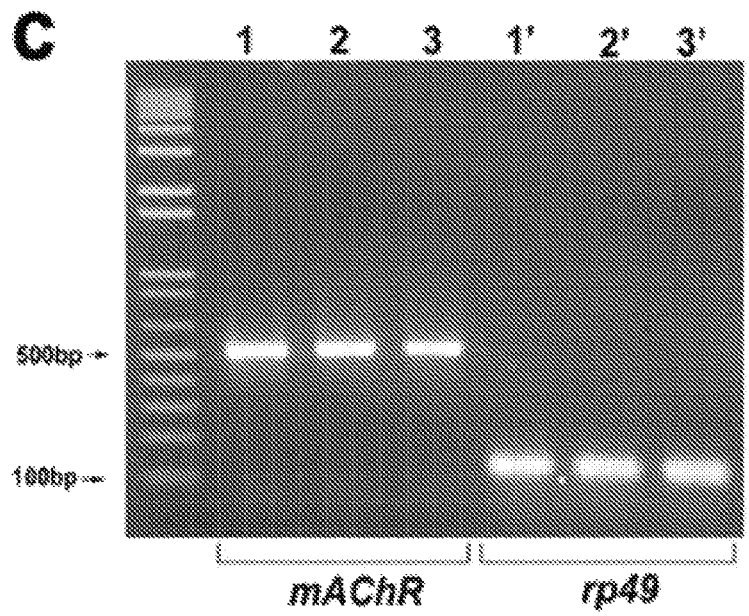
Figure 9:
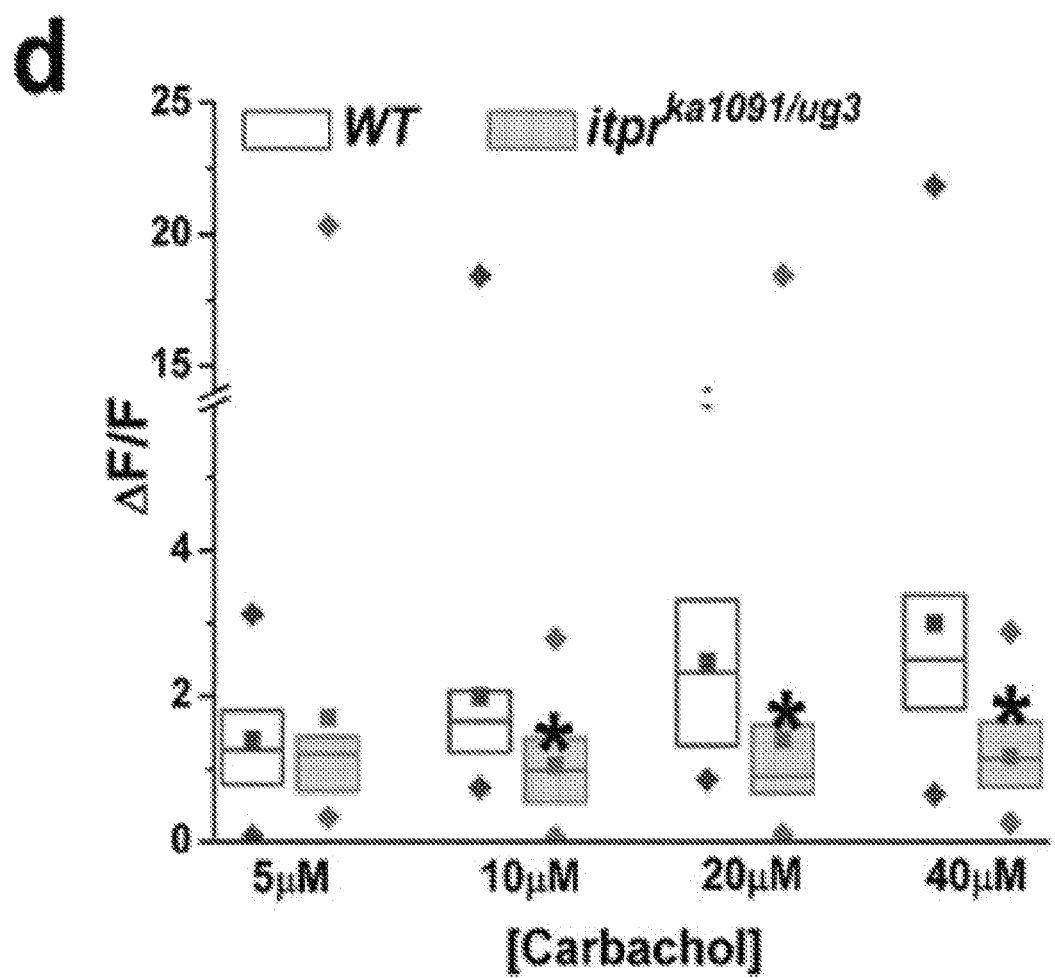
Figure 9:
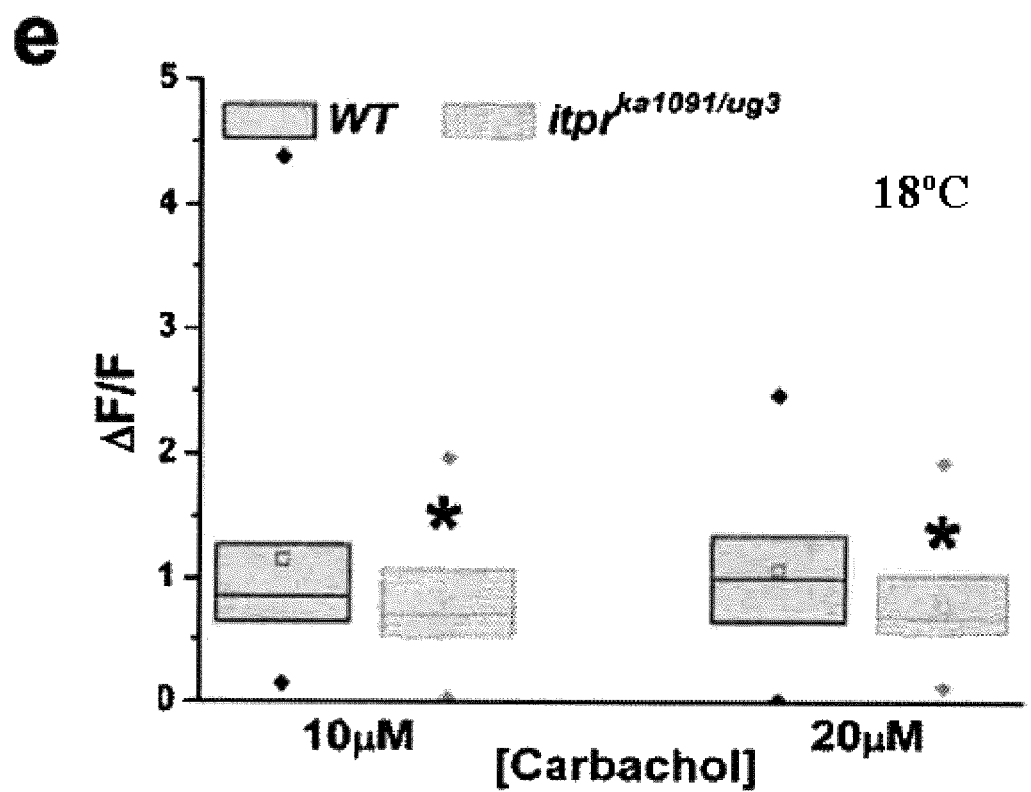

FIG. 9 Illustrative embodiments of characteristics of intracellular Ca²⁺ signals in itpr$^{ku}$ grown at 18° C.:

(a) Ca²⁺ add back experiments were done to measure SOC influx following store depletion in neurons of WT and itpr$^{ku}$ derived from larvae grown at 18° C. Box plots represent the spread of SOCE between the two populations which appear similar. 150 or more cells were analyzed for all the genotypes for each experiment;

(b) Store depletion was done with 10 µM thapsigargin to assay levels of store Ca²⁺ in neurons derived from larvae reared in cold. Box plots representing the range of store Ca²⁺ levels between the two populations show that unlike at 25° C., store Ca²⁺ in cells of itpr$^{ku}$ and WT grown at 18° C. is similar (P$_{ANOVA}$=0.44044); and (c) Transcript levels of mAChR were assayed by RT-PCR in total RNA derived from 3$^{rd}$ instar larval brains (mAChR expression was specifically targeted to larval neurons) and normalized to rp49. Lanes 1-3 contain PCR products for mAChR (463 bp); lanes 1'-3' contain PCR products for rp49. Lanes 1, 1' control 1, lanes 2, 2' itpr$^{ku}$ and lanes 3, 3' itpr$^{k/+}$. The mAChR transcript levels appear identical in all the genotypes tested; and (d) Box plot of the ΔF/F values in neurons from WT and itpr$^{ku}$ in response to stimulation with 5, 10, 20 and 40 µM of carbachol. Ca²⁺ release through InsP₃R in response to carbachol is significantly attenuated in itpr$^{ku}$ upon stimulation with 10 µM, 20 µM and 40 µM carbachol (**P$_{ANOVA}$=5.76E-5, 0.00393 and 1.55E-6 for 10, 20 and 40 µM carbachol stimulation respectively; P-values are all compared to W7). 170 or more cells were analyzed per genotype for each concentration of carbachol.

(e) Box plot of ΔF/F values in larval neurons derived from WT and itprku larvae grown at 17.5° C.

Figure 10:
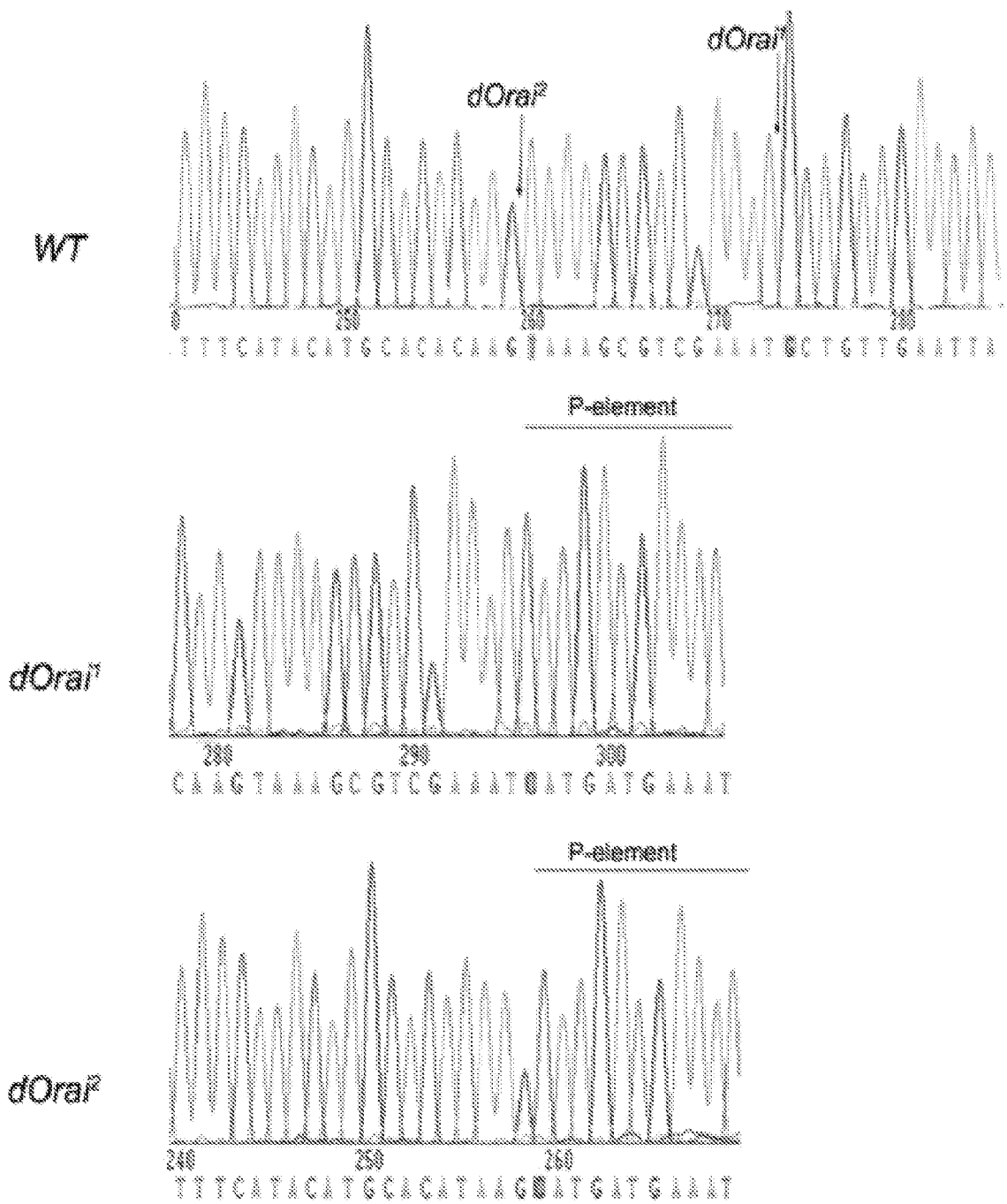

FIG. 10 Identification of a P-element insertion dOrai gene in dOrai$^1$ and dOrai$^2$. Position of the EP{gy2} insert in dOrai$^1$ and dOrai$^2$ was obtained from the www.ncbi.nim.nih.gov/entrez/viewer.fcgi?db=nucleotide&tool.FlyBase&val=CL705 882 database. For confirmation the region was amplified from genomic DNA isolated from the two strains. The forward primer used for amplification maps to the 5' end of the Orai gene and the reverse primer is complementary to the P-element end. The amplicons were sequenced to re-ascertain the positions of the P-elements in the two strains (arrows).

Figure 11:
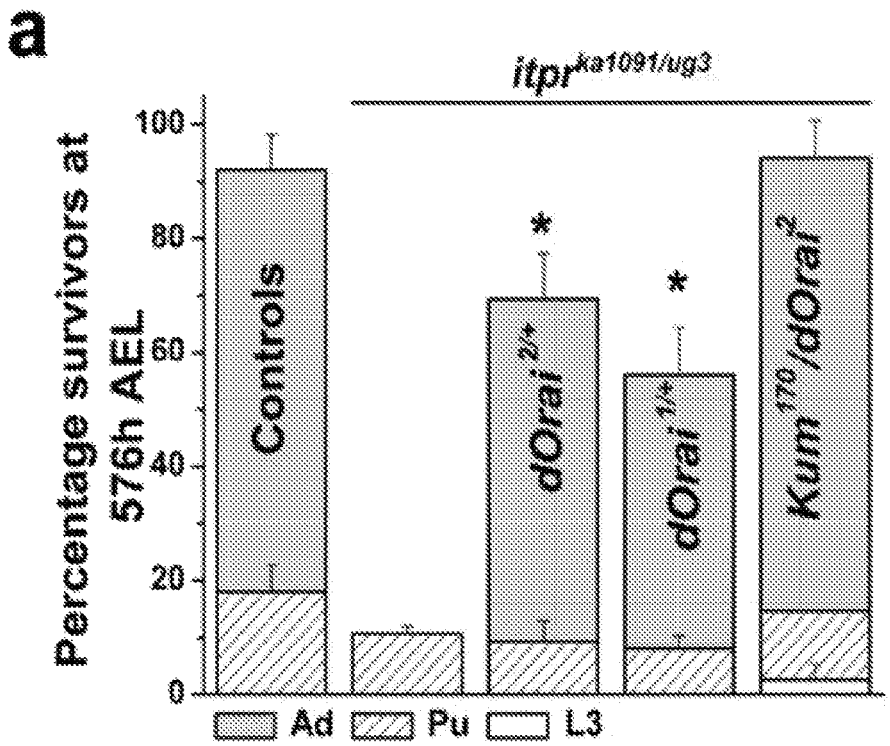
Figure 11:
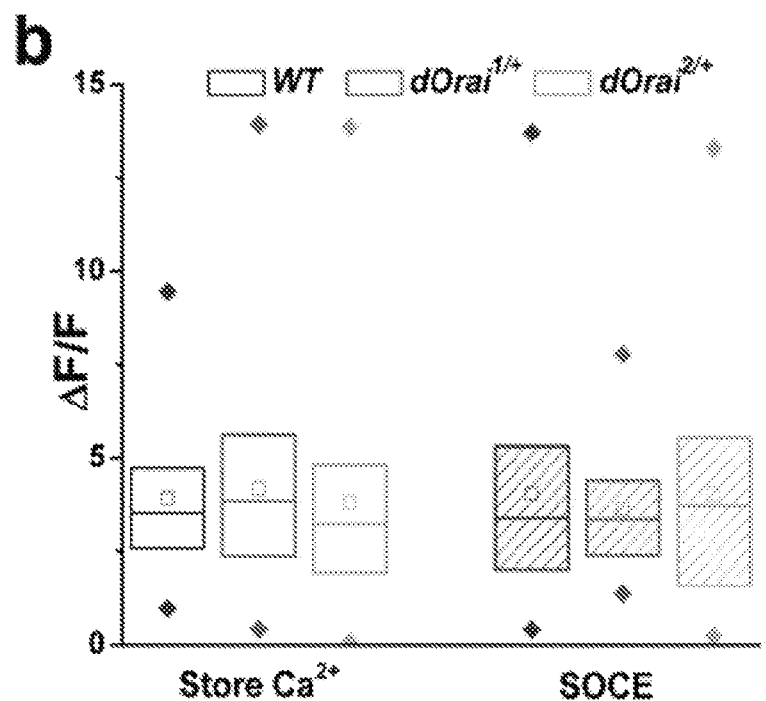
Figure 11:
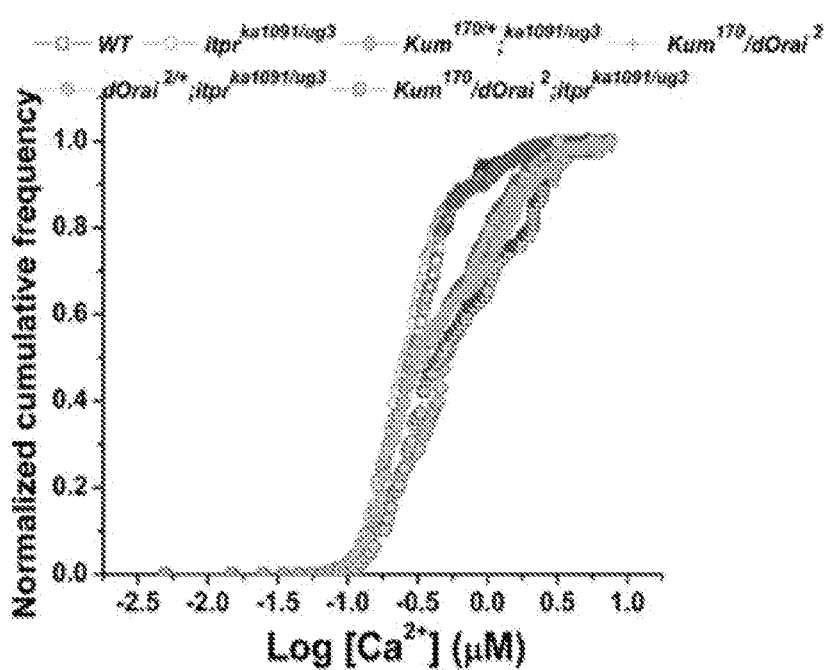
Figure 11:
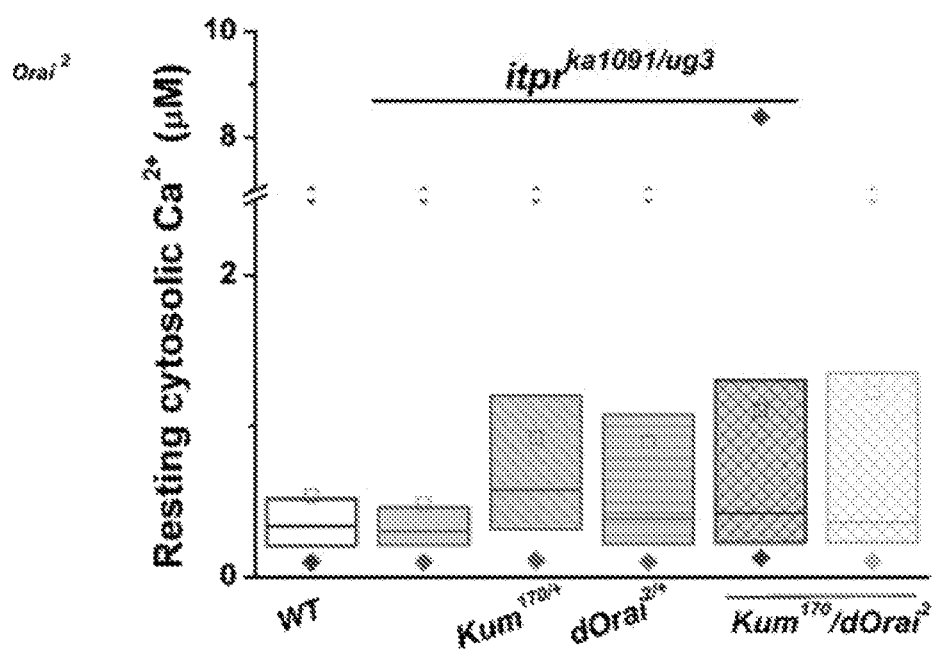

FIG. 11 Illustrative embodiments showing dOrai$^1$ and dOrai$^2$ suppress larval lethality of itpr$^{ku}$ at 18° and elevate resting cytosolic Ca$^{2+}$:

(a) Larval lethality in itpr$^{ku}$ is partially suppressed by dOrai$^{1/+}$ and dOrai$^{2/+}$. Error bars indicate S.E. (**P=0.00212 compared to itpr$^{ku}$);

(b) Box plot representation of $[Ca^{2+}]_{ER}$ and SOCE in the larval neurons of dOrai mutants. Intracellular store Ca$^{2+}$ and SOCE in neurons of dOrai$^{1/+}$ and dOrai$^{2/+}$ are similar to WT;

(c) K-S plot analyzing the distribution of intracellular Ca$^{2+}$ in neurons of indicated genotypes. The distribution is shifted towards the right in heterozygotes of Kum$^{170}$ or dOrai$^2$ with or without itpr$^{ku}$, indicating a higher frequency of cells with elevated $[Ca^{2+}]_i$ ($P_{K-S}$=0.001); and (d) Box plot analysis of resting cytosolic Ca$^{2+}$ in neurons of itpr$^{ku}$ with Kum$^{170/+}$ or dOrai$^{2/+}$ or both. The average basal Ca$^{2+}$ in cells harboring either dOrai$^2$ or Kum$^{170}$ with or without itpr$^{ku}$ in the background is significantly higher than WT (**$P_{ANOVA}$=0.0395 for dOrai$^{2/+}$ and 0.0089 for Kum$^{170/+}$). 170 or more cells were analyzed for each genotype in every experiment.

Figure 12:
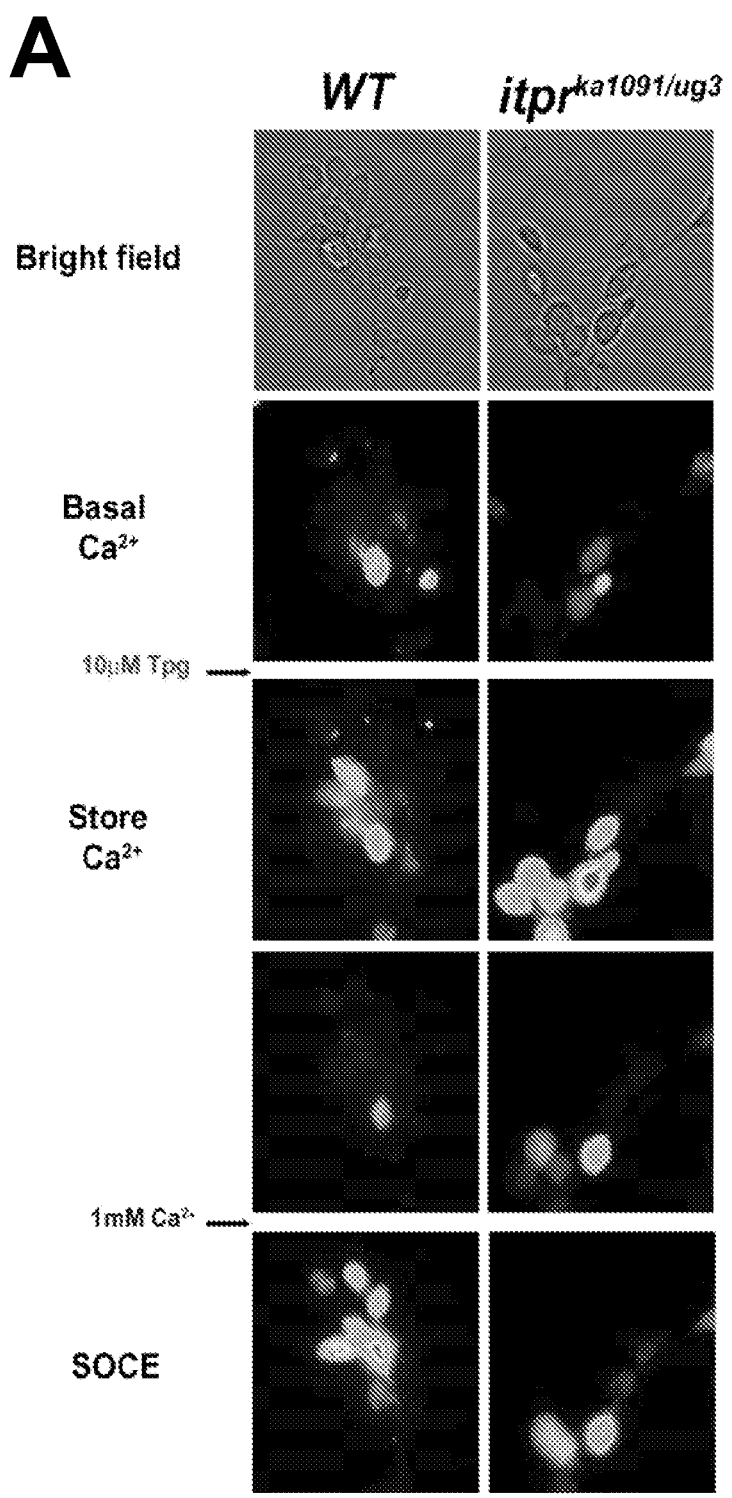
Figure 12:
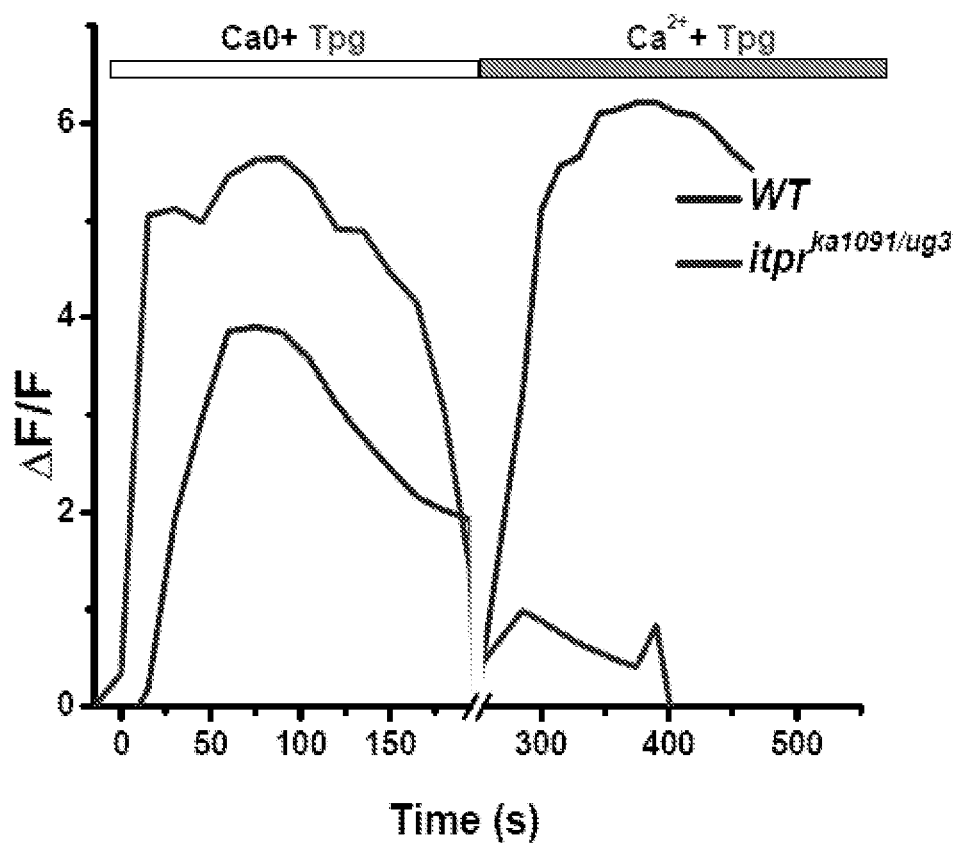

FIG. 12 Calcium imaging assay.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology provides a cell-based assay for identifying a compound that modulates store-operated, intracellular calcium levels in a cell that expresses a mutated inositol 1,4,5-trisphosphate receptor (itpr) gene. An itpr cell mutant cell of the present technology has abnormal levels of store operated, intracellular ionic calcium. In *Drosophila*, this abnormal level of store operated, intracellular calcium can be restored by the expression of certain other genes, such as by dOrai (see text and Examples below). In human cells, the itpr gene has a homolog known as InsP3R, and three ORAI gene isoforms, ORAI1 (FLJ14466), ORAI2 (C7prf19), and ORAI3 (MGC13024). See Peel et al., Am J Respir Cell Mol. Biol. 2008 June; 38(6): 744-749 (published online Jan. 31, 2008), which is incorporated herein by reference.

One of the characteristics of *Drosophila* mutant itpr cells is that intracellular calcium release is compromised when the cells are exposed to a stimulant. See, for instance, FIG. 6(a). Provided below are more details about a specific itpr mutant gene, known as "itpr-ku," which exhibits compromised calcium ion release characteristics, but the present technology is not limited to only this particular itpr mutation.

Another characteristic of the mutant itpr *Drosophila* cell is that normal calcium ion release can be restored upon the expression of a dOrai genes. This is because the genes encoding the SOC channel (Orai1) and the store Ca2+ sensor (Stim1) are known to maintain intracellular Ca2+ store levels ([Ca2+]ER) in stimulated T-cells, especially since the replenishment of [Ca2+]ER in T-cells is required for their prolonged activation. See Feske, S. et al., Nat Immunol 2, 316-324 (2001). Homologs of mammalian Orai and Stim exist in *Drosophila* as single genes and perform similar cellular functions in S2 cells, derived from a primary culture of late stage *Drosophila* embryos, where their depletion by gene specific double-stranded RNA (dsRNA) leads to abrogation of store-operated Ca2+ entry (SOCE). See Feske, S. et al., Nature, 441, 179-185 (2006); Vig, M., et al., Science, 312, 1220-1223 (2006); Zhang, S. L. et al., Proc Natl Acad Sci USA, 103, 9357-9362 (2006), which are all incorporated herein by reference. Hence, the presence of dOrai2 in an itprku background restores stimulated Ca$^{2+}$ release to wild type levels.

There are several characteristics of mutant itpr cells that provide for a useful model system including, but not limited to, the cells have a compromised calcium ion release upon stimulation, and the abnormal or non-wild-type calcium store and compromised calcium release characteristics are restored upon expression of an Orai gene.

The present technology is not limited to the use of *Drosophila* cells. Any cell type that exhibits these characteristics may be used. Such cells include, but are not limited to, any mammalian, insect, reptile, fish, or bird cell that has a mutant itpr gene, or a mutant homolog of a *Drosophila* itpr gene, that has the same or similar compromised calcium ion release characteristics as those of, for example, an itpr-ku *Drosophila* mutant cell. A mammalian cell includes but is not limited to a human cell, a primate cell, a mouse cell, a rat cell, a chicken cell, a cattle cell, a sheep cell, a hamster cell, a rodent cell, a pig cell, a cat cell, or a dog cell. A cell may have any tissue origin. That is a cell may be obtained from neuronal tissue, brain tissue, liver tissue, kidney tissue, cardiac tissue, pancreatic tissue, stomach tissue, lymphatic tissue, retinal tissue, intestinal tissue, or reproductive organ tissues, or any tissue or organ from a body.

Such cells can be isolated in several different ways. See, for instance, the series of volumes entitled "Human Cell Culture" by Koller, and Palsson (Eds). For instance, cells can be purified from blood; mononuclear cells can be enzymatically released from soft tissues (for example by applying collagenase, trypsin, or pronase) to break down the extracellular matrix and thereby release the cells; or via explant culture where tissue can be submerged in growth media and the resultant cells that are grown isolated from that medium. Thus, cells can be isolated from tissue suspension, grown in a culture dish, cultured in serum-free or chemically defined media, fused with other cells to produce hybrid cells, such as a hybridoma. See Bruce Alberts, et al., MOLECULAR BIOLOGY OF THE CELL (2002), which is incorporated herein in its entirety. There are also two other protocols for primary cell culture. One is for temporary cell culture studies (up to a few days) which is described in Banerjee et al., J Neurosci. 26(32): 8278-88 (2006), which is incorporated herein by reference, and also at page 126 of DROSOPHILA CELL IN CULTURE by Guy Echalier, Academic Press (1997), which is also incorporated herein by reference. For obtaining permanent cell lines the procedure is different and is described in Chapter 3 ("*Drosophila* continuous cell lines") of Echalier.

Cells that are obtained directly from an organism or individual are primary cells, which are able to replicate and divide for a period of time before they senesce. By contrast, an immortalized cell line can proliferate indefinitely; most vertebrate cells undergo senescence. Human somatic cells do not permanently express telomerase, which normally maintains the telomeres that otherwise shorten every cell division. Human fibroblasts, however, can be coaxed to proliferate indefinitely by providing them with the gene that encodes the catalytic subunit of telomerase; they can then be propagated as an "immortalized" cell line. See Alberts (supra) at Vol. III, Chapter 8 (Manipulating Proteins, DNA and RNA). Some human cells, however, still stop dividing even in the presence of telomerase because the culture conditions inadvertently arrest the cell cycle. Thus, these cellular arresting mechanisms have to be switched off, which can be accomplished by introducing certain cancer-promoting oncogenes derived from tumor viruses. Unlike human cells, however, most rodent cells do not turn off telomerase and therefore their telomeres do not shorten with each cell division. In addition, rodent cells can undergo genetic changes in culture that inactivate their checkpoint mechanisms, thereby spontaneously producing immortalized cell lines. Having said that, human embryonic stem cell lines, obtained from the inner cell mass of the early embryo, can proliferate indefinitely while retaining the ability to give rise to any part of the body.

Although all the cells in a cell line are very similar, they are often not identical. The genetic uniformity of a cell line can be improved by cell cloning, in which a single cell is isolated and allowed to proliferate to form a large colony. In such a colony, or clone, all the cells are descendants of a single ancestor cell. One of the most important uses of cell cloning has been the isolation of mutant cell lines with defects in specific genes. Studying cells that are defective in a specific protein often reveals valuable information about the function of that protein in normal cells.

Once isolated, cells can be grown and maintained at an appropriate temperature and gas mixture (typically, 37° C., 5% $CO_2$ for mammalian cells) in a cell incubator, although precise growth conditions vary each cell type, and variation of conditions for a particular cell type can result in different phenotypes being expressed. Similarly, recipes for growth media can vary, too, and include, but are not limited to variable ingredients and components, such as pH, glucose concentration, growth factors, and the presence of other nutrients. The growth factors used to supplement media are often derived from animal blood, such as calf serum.

Cells can be grown in suspension or adherent cultures. Some cells naturally live in suspension or can also be modified to survive in suspension cultures so that they can be grown to a higher density than adherent conditions would allow. By contrast, most cells obtained from solid tissues are adherent cells and require a surface to grow and differentiate. One type of adherent culture is organotypic culture which involves growing cells in a three-dimensional environment as opposed to two-dimensional culture dishes. This culture system is biochemically and physiologically more similar to in vivo tissue. In the case of adherent cultures, the media can be removed directly by aspiration and replaced.

Once cells have been isolated and grown in culture, they can be subsequently subcultured by a process called "passaging." This involves regularly transferring a small number of cells into a new vessel. Cells can be cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached; this is commonly done with a mixture of trypsin-EDTA, however other enzyme mixes are now available for this purpose. A small number of detached cells can then be used to seed a new culture.

Common immortalized human cell lines include but are not limited to 3T3 fibroblast (mouse), BHK21 fibroblast (Syrian hamster), MDCK epithelial cell (dog), HeLa epithelial cell (human), PtK1 epithelial cell (rat kangaroo), L6 myoblast (rat), PC12 chromaffin cell (rat), SP2 plasma cell (mouse), COS kidney (monkey), 293 kidney (human); transformed with adenovirus, CHO ovary (chinese hamster), DT40 lymphoma cell for efficient targeted recombination (chick), R1 embryonic stem cells (mouse), E14.1 embryonic stem cells (mouse), H1, H9 embryonic stem cells (human), S2 macrophage-like cells (Drosophila), and BY2 undifferentiated meristematic cells (tobacco). See Table 8.2 (Some Commonly Used Cell Lines) of Molecular Biology of the Cell, III, Chapter 8, by Alberts ($4^{th}$ Ed.) (2002).

Any of these cells, primary cell cultures, or immortalized cell lines, may be further modified to express a Drosophila mutated itpr gene or the homolog of the itpr gene that is equivalent to itpr that is endogenous to the genome of a particular cell from another species. An itpr mutant gene of the present technology is $itpr^{ku}$, which is an abbreviation of the genotypic representation of the underlying heteroallelic mutant combination $itpr^{ka1091/ug3}$. See Joshi et al., Genetics 166, 225-236 (2004), which is incorporated herein by reference in its entirety. The mutated residue in itprka1091 (Gly to Ser at 1891) lies in the modulatory domain while in itprug3 it lies in the ligand binding domain at position 224 (Ser to Phe); both residues are conserved in mammalian InsP3R isoforms. See Srikanth, S. et al., Biophys J, 86, 3634-3646 (2004). Three genes encode for a family of InsP3Rs in mammalian cells, including humans, and other vertebrates. The three full-length amino acid sequences are 60-80% homologous overall, with regions, including the ligand-binding and pore domains (discussed below), having much higher homology. See Foksett et al. (supra), subsection B "InsP3R Diversity." Invertebrates appear to express only a single InsP3R, most closely related to the type 1 isoform. In mammals, the InsP3R is ubiquitously expressed, perhaps in all cell types. The three channel isoforms have distinct and overlapping patterns of expression, with most cells outside the Central nervous system expressing more than one type. The itpr-equivalent mutant residues could directly affect InsP3R interactions with a store $Ca^{2+}$ regulating molecule like STIM. See Luik, R. M. et al., Nature, 454, 538-542 (2008); Taylor, C. W., Trends Biochem Sci, 31, 597-601 (2006). Measurement of InsP3-mediated $Ca^{2+}$-release from microsomal vesicles of $itpr^{ku}$ shows a significant reduction as compared to wild-type, non-$itpr^{ku}$ cells. See Srikanth et al., Biophys J, 86, 3634-3646 (2004). The ability of $itpr^{ku}$ to maintain elevated $[Ca^{2+}]ER$ at 25° C. suggests a possible interaction between this heteroallelic combination and Orai/STIM. See also Redondo, P. C., et al., Biochim Biophys Acta 1783, 1163-1176 (2008).

To produce transgenic fruit flies, the mutated itpr gene fragment is inserted between the two terminal sequences of a Drosophila transposon, the P element. The terminal sequences enable the P element to integrate into Drosophila chromosomes when the P element transposase enzyme is also present. To make transgenic fruit flies, this P element, containing the mutated sequence, is injected into a Drosophila embryo along with a separate plasmid containing the gene encoding the transposase. When this is done, the injected gene often enters the germ line in a single copy as the result of a transposition event. An example of such mutant cells are Drosophila larval primary neurons, which can be obtained from standard mechanical and enzymatic methods of dissociation of $3^{rd}$ instar larval brains. See Producing Primary Cultures of Drosophila Larval Neurons in the Overview of Examples below for specific methodological details. A human cell also may be made into a primary cell culture or immortalized in a human cell line as described herein.

Mammalian versions of such mutated Drosophila genes and transgenic fruit flies can also be made and used in the screening assay described here. For instance, mammalian InsP3R gene isoforms, InsP3R-1, InsP3R-2, and InsP3R-3, can be mutated in the same way as the Drosophila itprka1091 and itprug3 mutant genes, so as to effectively produce a mammalian cell that exhibits compromised calcium ion release upon stimulation, like the itpr-ku mutant Drosophila cell (which contains the −1091 and −ug3 mutations in the Drosophila itpr gene). These inositol 1,4,5-trisphosphate receptors (InsP3Rs) are a family of $Ca^{2+}$ release channels localized predominately in the endoplasmic reticulum of all cell types. They function to release $Ca^{2+}$ into the cytoplasm in response to $InsP_3$ produced by diverse stimuli, generating complex local and global $Ca^{2+}$ signals that regulate numerous cell physiological processes ranging from gene transcription to secretion to learning and memory. See Foskett et al., Physiol. Rev. 87: 593-658, (2007), which is incorporated herein by reference. The InsP3R is a calcium-selective cation channel whose gating is regulated not only by $InsP_3$, but by other ligands as well, such as cytoplasmic $Ca^{2+}$.

Phospholipase C hydrolyzes membrane lipids to produce inositol 1,4,5-trisphosphate ($InsP_3$), which diffuses in the cytoplasm and binds to the InsP3R receptor, which is an intracellular ligand-gated $Ca^{2+}$ release channel localized primarily in the endoplasmic reticulum membrane. See Foskett et al. ("Introduction"). The ER is the major $Ca^{2+}$ storage organelle in most cells. ER membrane $Ca^{2+}$-ATPases accumulate $Ca^{2+}$ in the ER lumen to quite high levels. Because the lumen contains high concentrations of $Ca^{2+}$ binding proteins, the total amount of $Ca^{2+}$ in the lumen may be >1 mM; the concentration of free $Ca^{2+}$ has been estimated to be between 100 and 700 µM. In contrast, the concentration of $Ca^{2+}$ in the cytoplasm of unstimulated cells is between 50 and 100 nM, 3-4 orders of magnitude lower than in the ER lumen. This low concentration is maintained by $Ca^{2+}$ pumps and other $Ca^{2+}$ transporters located in the ER, as well as plasma, membranes. Upon binding $InsP_3$, the InsP3R is gated open, providing a pathway for $Ca^{2+}$ to diffuse down this electrochemical gradient from the ER lumen to cytoplasm. $Ca^{2+}$ in the cytoplasm moves by passive diffusion, at a rate that is reduced by mobile and immobile $Ca^{2+}$ binding proteins acting as buffers. Consequently, microdomains with steep $Ca^{2+}$ concentration gradients can rapidly form and dissipate near the mouth of an InsP3R $Ca^{2+}$ channel. The $Ca^{2+}$ concentration adjacent to the open channel may be 100 µM or more, whereas concentrations as close as 1-2 µm from the channel pore may be below 1 µM.

According to the present methodology, one embodiment is to disrupt, all three mammalian InsP3R isoforms so that there is no functional endogenous inositol 1,4,5-trisphosphate receptor expressed in the cell. A cell culture can then be made from this triple knockout cell and then transformed with a mutant version of any of the InsP3R genes, so that the cell expresses only the mutated version of one InsP3R isoform. Accordingly, one could use a DT-40 cell line where all three InsP3Rs have been knocked out or silenced according to standard techniques described herein, such as by RNAi, site-directed mutagenesis, or homologous recombination. See also Kuhn & Wurst, GENE KNOCKOUT PROTOCOLS in the series entitled METHODS IN MOLECULAR BIOLOGY, Vol. 530 ($2^{nd}$ Ed., 2009, Humana Press) XVI, which is incorporated herein by reference. See also Barnett & Kontgen, Gene Targeting in a Centralized Facility at page 65 of Gene Knockout Protocols, Vol. 158 of METHODS IN MOLECULAR BIOLOGY by Tymms and Kola (2001, Humana Press), which is incorporated herein by reference. For a review on the use of RNA interference to knockdown or silence genes see Voorhoeve & Agami, Knockdown Stands Up, Trends Biotechnol., 21(1):2-4 (2003), which is incorporated herein by reference, and Xia et al., Transgenic RNAi: accelerating and expanding reverse genetics in mammals, Transgenic Research, 15:271-275 (2006), which is incorporated herein by reference. See also Hasan, G., Biological Implications of Inositol 1,4,5-triphosphate signaling from genetic studies in multicellular organisms, Proc. Indian natn Sci Acad. B69, No. 5: 741-752 (2003), which is incorporated herein by reference, and which describes the role of InsP3R receptors and mutated InsP3R genes in Drosophila, C. elegans, and mice.

As mentioned, one particular type of cell that can be engineered so as to have knocked-out InsP3R genes is the DT40 cell line, which is a chicken B cell line that permits efficient gene knockout targeting due to its high homologous recombination activities. See Buerstedde et al., The DT40 web site: sampling and connecting the genes of a B cell line, Nucleic Acids Research, Vol. 30, No. 1:230-231 (2002), which is incorporated herein by reference. A DT-40 cell line can be targeted according to standard methods described herein to knockout or silence the three InsP3R gene isoforms. See also Method 19 Targeted Transfection of DT40 Cells beginning at page 419 of REVIEWS AND PROTOCOLS IN DT40 RESEARCH by Buerstedde & Takeda (2006) published by Springer Netherlands. The triple mutated DT40 cell can then be engineered to express a mutated InsP3R gene, which can be, for example, mutated to contain the equivalent point mutations of the Drosophila itpr-ku mutated receptor gene. Such a DT40 cell then can be used, according to the assay protocols and methods presently described herein, to observe changes in intracellular calcium, and to monitor and record the effect(s) of a compound in modulating that intracellular calcium level. A cell that is therefore useful for the present assay is a human cell engineered to have knocked out versions of all three InsP3R endogenous isoforms but which has been transformed with at least one of a mutated InsP3R isoforms that has been altered in the same, or equivalent, way as the Drosophila itpr-ku gene, and reintroduced and expressed in that triple-knocked out human cell. Alternatively, two endogenous InsP3R genes may be knocked out according to standard techniques and the third endogenous InsP3R isoform mutated by site-directed mutagenesis or homologous recombination with the desired itpr-ku-like mutations, which would avoid the need to retransform the cell with an expression cassette comprising an exogenous mutated InsP3R sequence.

As mentioned, there are different ways to create a mutated gene. One way, a mutated itpr homolog gene can be introduced into cultured ES cells via homologous recombination. Cells containing the introduced mutant allele can then be identified and cultured to produce many descendants, each of which carries an altered gene in place of one of its two normal corresponding genes. These altered ES cells can then be injected into an embryo, such as a mouse embryo, whereafter the cells become incorporated into the growing embryo. The resultant mouse that is born will contain some somatic cells and some germ-line cells that carry the mutated itpr/homolog gene. Accordingly, upon breeding, some progeny will contain the altered gene in all of their cells. These cells then can be obtained and isolated and cultured according to the methods described above. These progeny, if mice, and if the mutation completely deactivates the itpr/homolog gene are known as knockout mice. Accordingly, cells from knockout mice also can be isolated and cultured according to the techniques described herein for use in the present assay.

Alternatively, site-directed mutagenesis can be used to target mutations into the itpr/homolog gene, such as the point mutations described above for itpr-ku mutations. A synthetic DNA oligonucleotide designed to contain those mutations is then hybridized with single-stranded plasmid DNA that contains the version of the itpr gene to be altered. The oligonucleotide serves as a primer for DNA synthesis by DNA polymerase, thereby generating a duplex that incorporates the altered sequence into one of its two strands. After transfection, plasmids that carry the fully modified gene sequence are obtained. The appropriate DNA is then inserted into an expression vector so that the redesigned protein can be produced in the appropriate type of cells, isolated as described above, for use in the presently-described screening assay. For additional information on molecular biology cloning methods and site-directed mutagenesis, see Sambrook et al., MOLECULAR CLONING: A LABORATORY MANUAL, (2d Ed), published by Cold Spring Harbor Laboratory (1989), which is incorporated herein by reference, particularly Chapter 15 on Site-Directed Mutagenesis.

Foreign DNA can also be readily integrated into random positions of many animal genomes. In mammals, for instance, linear DNAs that are introduced into mammalian cells are rapidly ligated end-to-end by intracellular enzymes to form long tandem arrays, which usually become integrated into a chromosome at an apparently random site. If the modified chromosome is present in the germ line cells (eggs or sperm), the mouse will pass these foreign genes on to its progeny, as described in the preceding section.

The screening assay of the present technology identifies those compounds that modulate, i.e., cause the increase or decrease of intracellular calcium levels, of the itpr cell mutant. An aliquot of cells, for instance those that have been obtained and isolated as described above, can be put into a new vessel, or into a well of a standard 96-well plate, and the calcium imaged. Calcium ion imaging of the cells can be accomplished by recording fluorescent intensity values before and after stimulation of cells with candidate compounds. Fluorescence is measured in arbitrary units (AU). For example, for a wild type cell, if the resting fluorescence is 600 AU, stimulation with 10 µM thapsigargin would increase the pixel intensity value to 2500. This difference in fluorescent intensity is then normalized to the resting fluorescent intensity to determine $\Delta F/F$ (1300/600 which would be 3.167) the range of which is plotted as a box plot. This calculation has been done for every calcium imaging experiment where store calcium, SOCE and stimulated release through InsP3R is measured. For measuring resting cytosolic $Ca^{2+}$ in primary *Drosophila* neurons of different genotypes, the ratiometric fluorescent dye Indo-1AM can be used. Accordingly, the resting calcium levels and characteristics of an aliquot of cells can be obtained and recorded. Then, a candidate compound can be added to the same or a different aliquot of the same cells and the calcium levels and patterns imaged again using the same technique and then compared to the non-compound-added cells to determine how, if at all, the compound changed the intracellular calcium stores and release of calcium ions via the itpr-ku mutant.

Such a screening assay can be performed on other cells from other species which have been isolated and cultured, or immortalized, according to the techniques described herein and known to the skilled person. A mammalian cell, for instance, can be used in a screening assay to determine if a candidate compound modulates the calcium store and calcium pattern of the mammalian cell. Thus, before so using a mammalian cell, a resting image of the mammalian cell which contains an equivalently-mutated itpr homolog gene, i.e., equivalent to the *Drosophila* itpr-ku mutant gene, can be taken and recorded. As a preliminary matter, one could compare the mutated mammalian cell's calcium image to that of the *Drosophila* itpr-ku mutant cell calcium pattern to determine any similarities or differences. Then, a candidate compound can be added to the mammalian mutant cell and the mammalian mutant cell then re-imaged to obtain a post-administration calcium image. By comparing the two images, before and after administration of the compound, it can be determined what effect, if any, the compound has on the calcium store and flux of the mammalian mutant cell.

The screening assay does not have to be comprised of only two time points (before and after) of administration of the compound. Multiple "doses" of a compound can be administered to an aliquot of cells over time, which are sequentially imaged for changes in calcium ion storage and flux; or a compound can be added to separate individual aliquots of cells over a period of time and separate images obtained for each aliquot so that any changes in calcium imaging can be followed over that period of time.

In one embodiment, therefore, a compound that fully or partially restores the intracellular calcium levels of the itpr cell mutant to a level that is at, or which approximates, the intracellular calcium level of a non-mutant cell, is a compound that can be used to modulate intracellular calcium levels. Thus, a compound that modulates calcium levels is useful for treating diseases characterized by abnormal store-operated, intracellular calcium levels.

Accordingly, a method of the present technology provides for the identification of a compound that modulates store-operated calcium entry levels in a cell, comprising providing a test compound to an itpr mutant cell; and determining whether the test compound increases or decreases the abnormal store-operated, intracellular calcium level of the itpr mutant cell.

The compound can be added directly to such cultures of itpr mutant cells or to an itpr mutant cell line or to cells obtained from an organism, such as from a mammal, e.g., human cells, *Drosophila* fruit flies, that have been isolated and/or cultured from the organism. The concentration of the test compound to be used is determined empirically so as to obtain a measurable fluorescence difference. In one embodiment, the compound modulates the calcium level of the itpr mutant cell such that that level changes in the direction toward approximating the calcium level of a control cell. That is, the mutant cell calcium level may be elevated compared to a control cell in which case the compound, when it is provided to the cell, lowers the elevated calcium level so that the calcium level moves in the direction toward the calcium level of a control cell.

Conversely, the mutant cell calcium level may be depleted compared to a control cell in which case the compound, when it is provided to the cell, increases the elevated calcium level so that the calcium level moves in the direction toward the calcium level of a control cell. A compound that increases or decreases the calcium release through InsP3R and/or changes the store operated calcium entry in an itpr-ku mutant cell is therefore a compound that modulates store-operated calcium entry levels. The level of calcium may be monitored before, during, or after administration of the compound, such as at discrete endpoints or at constant intervals, such as every 5 minutes over the course of a set period of time. The calcium levels also can be compared to the calcium level of a control cell. A control cell may be, for instance, (i) a wild-type, normal cell, (ii) a cell with a dOrai/Kum$^{-170}$; itpr$^{ku}$ mutant genotype, or (iii) a cell without the itpr$^{ku}$ mutant genotype. An example of a control cell is a cell from the brain of a wild-type Canton-S *Drosophila* strain. Accordingly, a test compound that increases or decreases the calcium level in an itpr mutant cell, such as in the itpr$^{ku}$ mutant cell described herein, or in a cell from a different species which contains an equivalently mutated itpr/InsP3R gene is a desirable compound that modulates store-operated calcium entry levels.

"Modulates" is commonly understood to reflect a variation in a particular parameter. Thus, as used herein, modulation refers to the change in level of intracellular calcium ions before and after a compound has been provided to a mutant cell. That is, the effect of a compound on a cell of the present technology may be to increase or decrease the level of intracellular ionic calcium in that cell. The degree to which the intracellular calcium level changes so as it closer approximate the intracellular ionic calcium level of that of a non-mutant, i.e., control, cell is indicative of the compound's ability to fully or partially "restore" the abnormal intracellular ionic calcium level of the itpr mutant cell to that of a control cell. A control cell may be, for instance, (i) a wild-type, normal cell, (ii) a cell with a dOrai/Kum$^{-170}$; itpr$^{ku}$ mutant genotype, or (iii) a cell without the itpr$^{ku}$ mutant genotype. Quantitative comparative data concerning levels of store-operated calcium between itpr-ku cells and "control" cells are show in FIG. 6(*e*). The modulation of calcium levels therefore encompasses either increases and decreases in calcium levels of the mutant itpr cell, such as the mutant itpr$^{ku}$ cell.

A mutant itpr cell that has been exposed to a modulatory compound may subsequently have an intracellular ionic calcium level that is different from the intracellular ionic calcium level of the same mutant itpr cell which has not been exposed to the modulatory compound. That is, the modulatory compound may increase the intracellular ionic calcium level of the mutant itpr cell or decrease the intracellular ionic calcium level of the mutant itpr cell. Accordingly, after the modulatory compound has been provided to the mutant itpr cell the intracellular ionic calcium level of the mutant itpr cell may be near to that of intracellular ionic calcium levels of a wild type cell or some such control cell. Accordingly, after the modulatory compound has been provided to the mutant itpr cell, the mutant itpr cell store-operated intracellular ionic calcium level may be described in terms of whether that level is that of the wild type calcium level or in terms of a percentage of wild type ionic calcium levels. For instance, after providing a compound to an itpr mutant cell, the store-operated intracellular ionic calcium level may increase to a level or concentration that is half the concentration of the wild type ionic calcium level, i.e., the itpr mutant cell has a post-compound exposure ionic calcium that is about 50% that of the wild type ionic calcium level/concentration. Or the compound may effectuate an increase in store-operated ionic calcium levels such that the resultant concentration of ionic calcium after the compound has been provided to it is almost identical to the wild type ionic calcium level, e.g., 80-99%, or 100% identical, to the ionic calcium level of the wild type cell measured under the same conditions. Accordingly, after providing a compound to an itpr mutant cell, the itpr mutant cell may have a store-operated intracellular ionic calcium level that is about 50% of that of a control cell intracellular calcium level, about 55% of that of a control cell intracellular calcium level, about 60% of that of a control cell intracellular calcium level, about 65% of that of a control cell intracellular calcium level, about 70% of that of a control cell intracellular calcium level, about 75% of that of a control cell intracellular calcium level, about 80% of that of a control cell intracellular calcium level, about 85% of that of a control cell intracellular calcium level, about 90% of that of a control cell intracellular calcium level, about 95% of that of a control cell intracellular calcium level, or about 100% of that of a control cell intracellular calcium level. Accordingly the level of intracellular, store-operated ionic calcium may approximate the corresponding level in a control cell after exposure to the compound. A control cell of the present technology may be (i) a wild-type, normal cell, (ii) a cell with a dOrai/Kum$^{-170}$; itpr mutant genotype, or (iii) a cell without the itpr mutant genotype. Or the compound may effectuate a decrease in store-operated ionic calcium levels such that the resultant concentration of ionic calcium after the compound has been provided to it is lowered and almost identical to the wild type ionic calcium level, e.g., 80-99%, or 100% identical, to the ionic calcium level of the wild type cell measured under the same conditions. Accordingly, after providing a compound to an itpr mutant cell, the itpr mutant cell may have a store-operated intracellular ionic calcium level that becomes reduced until it is near or at the level of intracellular ionic calcium of a control cell. Taking the change as an absolute value, the itpr mutant cell may have a store-operated intracellular ionic calcium level that is about 50%, 55%, 60%, 65%, 70%, 75%, 80%, 85%, 90%, 95%, or about 100% of that of a control cell intracellular calcium level. The itpr mutant cell may have a store-operated intracellular ionic calcium level that is a range of about 50%-100%, 55%-100%, 60%-100%, 65%-100%, 70%-100%, 75%-100%, 80%-100%, 85%-100%, 90%-100%, or about 95%-100% of that of a control cell intracellular calcium level.

Thus the present technology concerns changes toward similarity in store-operated calcium levels that result from the exposure of the itpr mutant cell to a compound that increases that cell's calcium levels or decreases that cell's calcium levels so that the resultant change is toward a level similar to that of a wild-type or control cell.

The determining whether a test compound modulates the abnormal store-operated, intracellular ionic calcium level of the itpr$^{ku}$ cell can be achieved by performing calcium imaging of the store-operated calcium entry environment of the itpr$^{ku}$ cell, and recording the calcium imaging patterns before and after the addition of the test compound to the itpr$^{ku}$ cell, and comparing the calcium imaging patterns of the itpr$^{ku}$ cell with the calcium imaging of the store-operated calcium entry environment of a control cell, wherein the change toward similarity in calcium imaging patterns between the two cells indicates the test compound can modulate the store-operated calcium entry level of the itpr$^{ku}$ cell.

Thus, according to the present technology, a compound modulates calcium levels in the store-operated calcium entry environment if the calcium imaging pattern of the store-operated calcium entry environment changes in the direction of matching the calcium imaging pattern of (i) a wild-type, normal cell, (ii) a cell with a dOrai/Kum$^{-170}$; itpr$^{ku}$ mutant genotype, or (iii) a cell without the itpr$^{ku}$ mutant genotype; or the calcium imaging pattern of the store-operated calcium entry environment matches or is equivalent to the calcium imaging pattern of (i) a wild-type, normal cell, (ii) a cell with a dOrai/Kum$^{-170}$; itpr$^{ku}$ mutant genotype, or (iii) a cell without the itpr$^{ku}$ mutant genotype A compound of the present technology, which modulates store operated calcium levels, includes, but is not limited to, e.g., a small molecule, an inorganic compound, an organic compound, a biomolecule, a chemical, a protein, a peptide, a lipid (or derivative thereof), a carbohydrate (derivative thereof), or a nucleic acid. Such compounds may affect any aspect of the calcium store, such as opening and closing of the store operated calcium channel (SOC), in order to modulate the ionic concentration of calcium within an itpr mutant cell of the present technology. Thus, the present technology is not limited to any particular cellular, chemical, or genetic target with which the compound interacts or regulates in order to directly or indirectly modulate ionic calcium levels.

With respect to a nucleic acid, a compound may be a gene that encodes a protein, a DNA or RNA oligonucleotide, or a type of RNA, such as single-stranded sense or antisense RNA, or an RNA duplex, such as a hairpin loop RNA or a duplex formed from two annealing single stranded RNA strands. Thus, the present technology contemplates the introduction of a nucleic acid compound into an itpr mutant cell that causes a change in expression of one or more genes in the itpr mutant cell (such as, but not limited to, by sense or antisense suppression or RNA interference, RNAi), which in turn results in a change or modulation in calcium levels in the itpr mutant cell. Such nucleic acids may target one or more store-operated channel genes, and related genes, thereby downregulating their expression. For example, transient receptor potential (TRP) gene mutants are associated with defective calcium ion influx. A number of mammalian homologs of TRP have been found, and the TRP superfamily includes more than 20 related cation channels. These TRP channels can be classified into three major subfamilies: TRPC, TRPV, and TRPM. The TRPC subfamily exhibits the greatest sequence homology to *Drosophila* TRP. TRPC1, for instance, is involved in store-operated entry, while overexpression of TRPC3 enhances store-operated calcium. See Parekh and Putney, Physiol. Rev. 85: 757-810, 2005, which is incorporated herein by reference in its entirety.

A variety of mechanisms are known to directly or indirectly affect calcium entry through store-operated calcium channels, such as but not limited to (i) rapid inactivation (such as using fast calcium chelators like BAPTA); (ii) store refilling (and effect of thapsigargin); (iii) slow inactivation (effects of EGTA and calmodulin); and the effects of certain other compounds, e.g., the effect of sphingomyelinase, sphingosine, and ceramides (all of which reduce thapsigargin-evoked $Ca^{2+}$ entry) as targets in the sphingomyelin pathway that may regulate store-operated influx; the effect of nitric oxide (NO), via cGMP and then cGMP-dependent protein kinase, on stimulating $Ca^{2+}$ reuptake into the stores; the effect of protein kinase C on store-operated influx of calcium; and the effect of arachinoic acid as an inhibitor of store-operated calcium entry. Other examples of modulatory compounds include Loperamide, which is a common antidiarrheal agent (see Harper et al., Proc Natl Acad Sci USA., 94(26): 14912-14917 (1997), which is incorporated herein by reference in its entirety); and the pyrazole derivative, YM-58483. See Ishikawa et al., J. Immunol., 170: 4441-4449 (2003), which is incorporated herein by reference in its entirety.

The central role of calcium influx pathway in so many physiological systems makes the itpr mutant cell assay of the present technology a useful tool for identifying compounds that modulate and affect store-operated calcium ion influx and storage levels. The present assay identifies compounds useful for treating diseases where altered intracellular $Ca^{2+}$ signaling or homeostasis is or may be a causative agent. Exemplary diseases in this regard include, but are not limited to spino-cerebellar ataxia (Banerjee, S. & Hasan, G., Bioessays 27, 1035-1047 (2005)), which arises by heterozygosity of the IP3R1 gene (van de Leemput, J. et al., PLoS Genet, 3, e108 (2007)); severe combined immuno-deficiency due to a mutation in Orai1 (Feske, S. et al., Nature, 441, 179-185 (2006); and Thompson, J. L. et al., J Biol. Chem., 284(11): 6620-6 (2009)); and Darier's disease from a mutation in SERCA2 (Sakuntabhai, A. et al., Nat Genet, 21, 271-277 (1999)).

There are also documented cases of immunodeficiencies apparently derived from impaired store-operated entry, as well as evidence for a role of store-operated entry in acute pancreatitis. There also is growing evidence for a role for store-operated entry in the toxic effects of environmental chemicals that affect $Ca^{2+}$ homeostasis. Other categories of diseases which can benefit from modulators of store-operated calcium levels includes, severe combined immunodeficiency, acute pancreatitis, Alzheimer's Disease, Toxicology (prolonged elevation of cytoplasmic $Ca^{2+}$ can be toxic to cells; a typical example of agents in this class is thapsigargin, mentioned above, which is capable of killing cells in vitro by apoptosis, or acting as a tumor promoter in vivo). An example of a calcium ion-mobilizing environmental toxin is tributyltin, an important component of marine paints which has been shown to accumulate in coastal waters and estuaries and in marine organisms, which activates $Ca^{2+}$ entry. See Parekh and Putney, Physiol. Rev., 85: 757-810 (2005), which is incorporated herein by reference in its entirety.

Based on the underlying changes in intracellular $Ca^{2+}$ properties in such diseases, the present technology provides a way to identify compounds which may fully or partially restore or otherwise modulate ionic calcium levels in $itpr^{ku}$ mutant cells. The compounds that are identified as able to modulate calcium levels in $itpr^{ku}$ mutant cells are compounds that could be useful in modulating calcium levels in cells of individuals with such diseases. Thus, a modulatory compound of the present technology can be administered to an individual with a disease characterized by an intracellular calcium abnormality, in such an effective amount, and for a period of time, or under a particular dosage regime so as to help rectify that abnormality by modulating the intracellular ionic calcium level of cells of that individual.

EXAMPLES

The present technology is further illustrated by the following examples, which should not be construed as limiting in any way.

Overview of Examples

The Examples that follow below show that store-operated $Ca^{2+}$ entry through the Orai/STIM pathway and the rate of clearance of cytoplasmic $Ca^{2+}$ by SERCA together shape intracellular $Ca^{2+}$ response curves in *Drosophila* neurons. The development and function of the flight circuit appears most sensitive to these cellular $Ca^{2+}$ dynamics, changes in which have a profound effect on its physiological and behavioral outputs. Other circuits such as those required for walking, climbing and jumping remain unaffected.

The flow of information in a neural circuit goes through multiple steps within and between cells. Suppression experiments, such as the ones described here, present a powerful genetic tool for understanding the mechanisms underlying both the formation of such circuits and their function. See Ganetzky, B. & Wu, C. F., Genetics, 100, 597-614 (1982). Out-spread wings, higher spontaneous firing and initiation of rhythmic firing on air-puff delivery in itprku are suppressed by either increasing the quanta (through introduction of hypermorphic alleles of dOrai and by dOrai+ over-expression) or by increasing the perdurance (through mutant Kum170) of the intracellular $Ca^{2+}$ signal (FIG. 7, central panels).

Flight ability and maintenance of flight patterns requires SOCE in addition to increased quanta and perdurance of the $Ca^{2+}$ signals, suggesting that SOCE in neurons contributes to recurring $Ca^{2+}$ signals essential for flight maintenance (FIG. 7, last panel).

The concerted activity of $Ca^{2+}$ flux pathways is critical for both the morphology and activity of neuronal circuits 1. The results below demonstrate a requirement for $Ca^{2+}$ influx through SOC channels in electrically excitable cells, which very likely constitute the flight CPG. Aminergic, glutamatergic and insulin-producing neurons could assist in development and/or directly constitute the circuit. Biogenic amines, especially serotonin, have been reported to regulate axonal growth and also control rhythmic behavior in other invertebrate systems. See Budnik, V. et al., J Neurosci, 9, 2866-2877 (1989); and Koert, C. E., et al., J Neurosci, 21, 5597-5606 (2001). The glutamatergic domain consists of a wide range of inter-neurons and the motoneurons that directly innervate the indirect flight muscles that power wing beating during flight. See Mahr, A. & Aberle, H., Gene Expr Patterns, 6, 299-309 (2006). Insulin producing neurons on the other hand probably control the growth of functional neurons and synapses that establish connectivity in the CPG circuit.

Producing Primary Cultures of *Drosophila* Larval Neurons

According to the present technology, primary cultures of *Drosophila* larval neurons were plated in 200 µl *Drosophila* M1 medium (30 mM HEPES, 150 mM NaCl, 5 mM KCl, 1 mM MgCl2, 1 mM CaCl2, and 35 mM sucrose, pH 7.2) supplemented with 10% fetal bovine serum (Invitrogen, USA), 50 U/ml penicillin, 50 µg/ml streptomycin, and 10 µg/ml Amphotericin B as described previously. See Wu et al., J Neurosci. 1983 September; 3(9):1888-99. Briefly, brain and the ventral ganglion complex were dissected from *Drosophila* $3^{rd}$ instar larvae of the appropriate genotypes. The brain tissue was mechanically dissociated using syringe needles in Schneider's medium containing collagenase (0.75 µg/µl) and dispase (0.4 µg/µl) and incubated in the proteolytic medium for 20 minutes to allow complete dissociation of the tissue. The lysate containing essentially single cells was then spun down, re-suspended in M1 medium (200 µl of M1 was used for lysates of four brains), and plated onto 35 mm culture dishes with a poly-lysine coated coverslip for the bottom. The cells were incubated at 22° C. for 14-16 h before imaging.

Example 1

Store-Operated Calcium Entry in *Drosophila* Neurons is Dependent Upon Orai and STIM Genes encoding the SOC channel (Orai1) and the store $Ca^{2+}$ sensor (Stim1) are known to maintain intracellular $Ca^{2+}$ store levels ([Ca2+]ER) in stimulated T-cells. The replenishment of [Ca2+]ER in T-cells is required for their prolonged activation. See Feske, S. et al., Nat Immunol 2, 316-324 (2001). Homologs of mammalian Orai and Stim exist in *Drosophila* as single genes and perform similar cellular functions in S2 cells, derived from a primary culture of late stage *Drosophila* embryos, where their depletion by gene specific double-stranded RNA (dsRNA) leads to abrogation of store-operated $Ca^{2+}$ entry (SOCE). See Feske, S. et al., Nature, 441, 179-185 (2006); Vig, M., et al., Science, 312, 1220-1223 (2006); Zhang, S. L. et al., Proc Natl Acad Sci USA, 103, 9357-9362 (2006).

Figure 1:
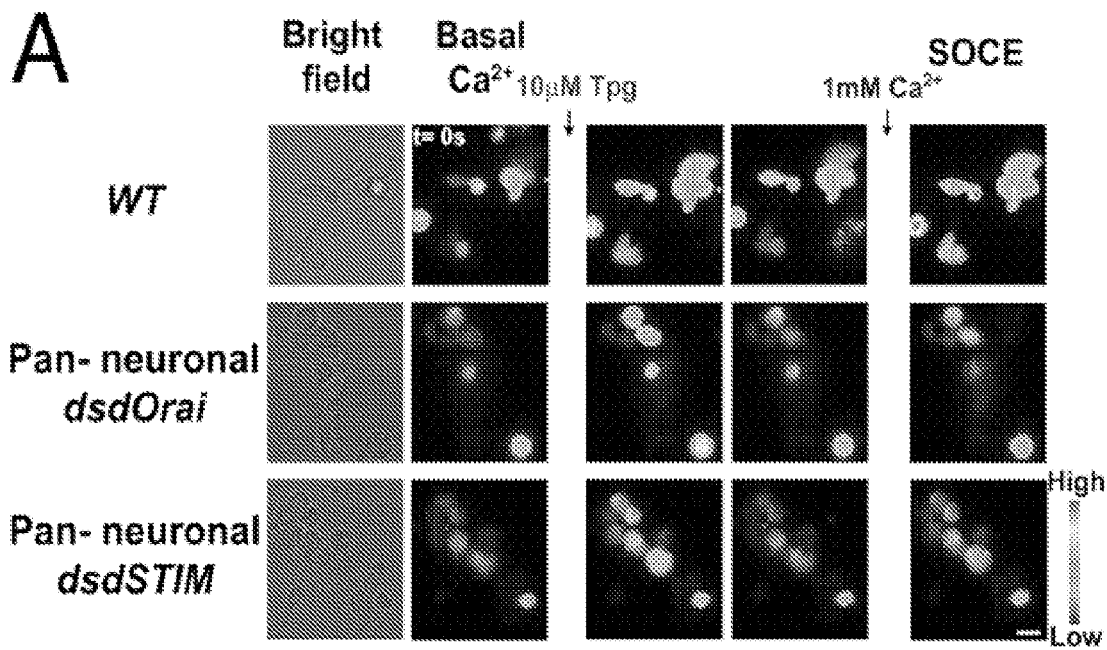
FIG. 1 Illustrative embodiments demonstrating that intracellular $Ca^{2+}$ homeostasis in larval neurons is altered upon RNAi knock down of dOrai and dSTIM.
Figure 1:
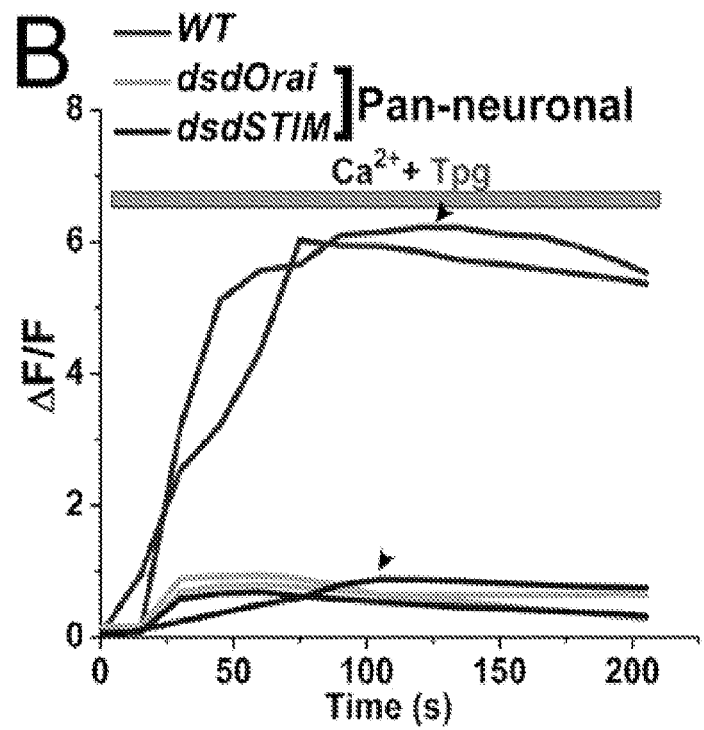
Figure 1:
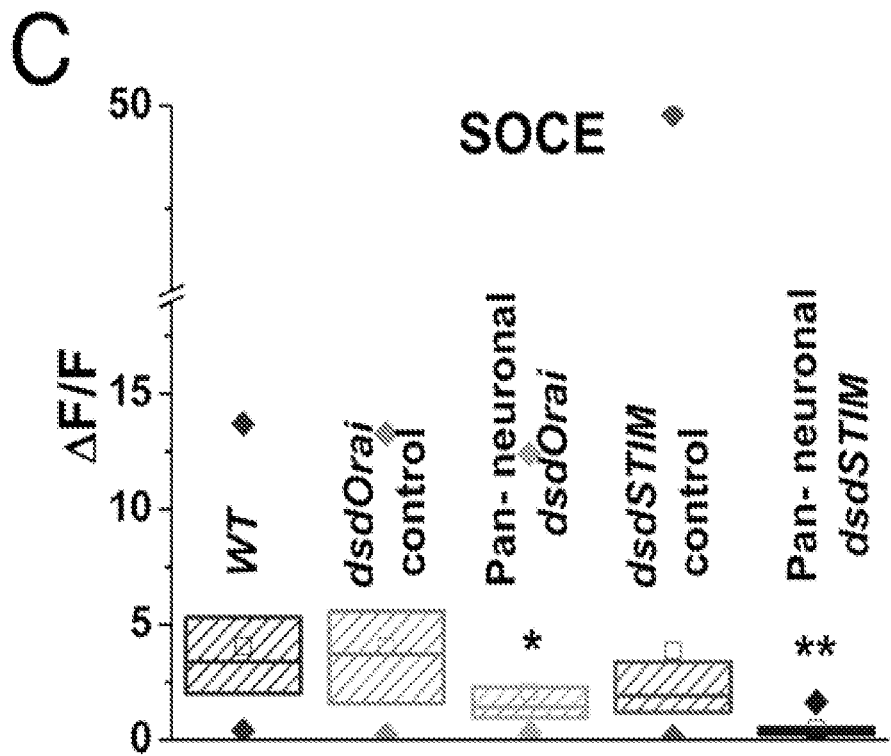
Figure 1:
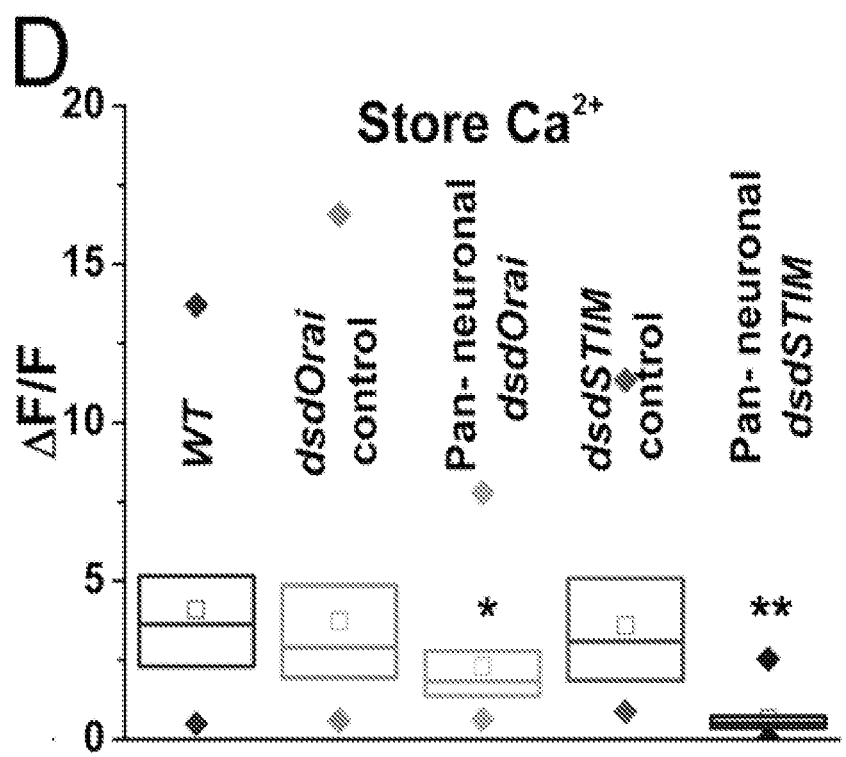
Figure 1:
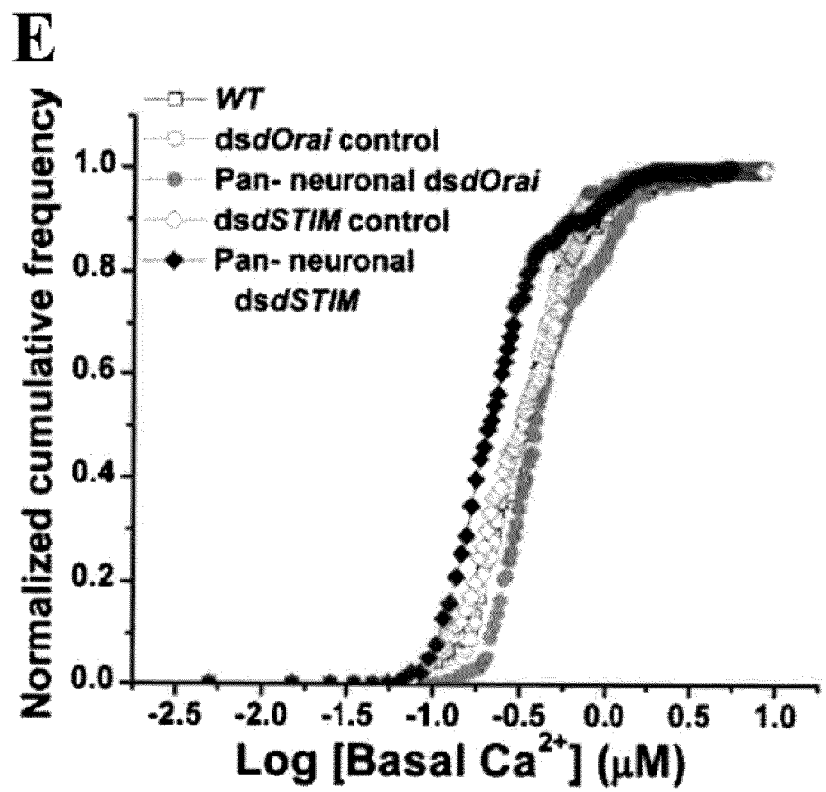
Figure 1:
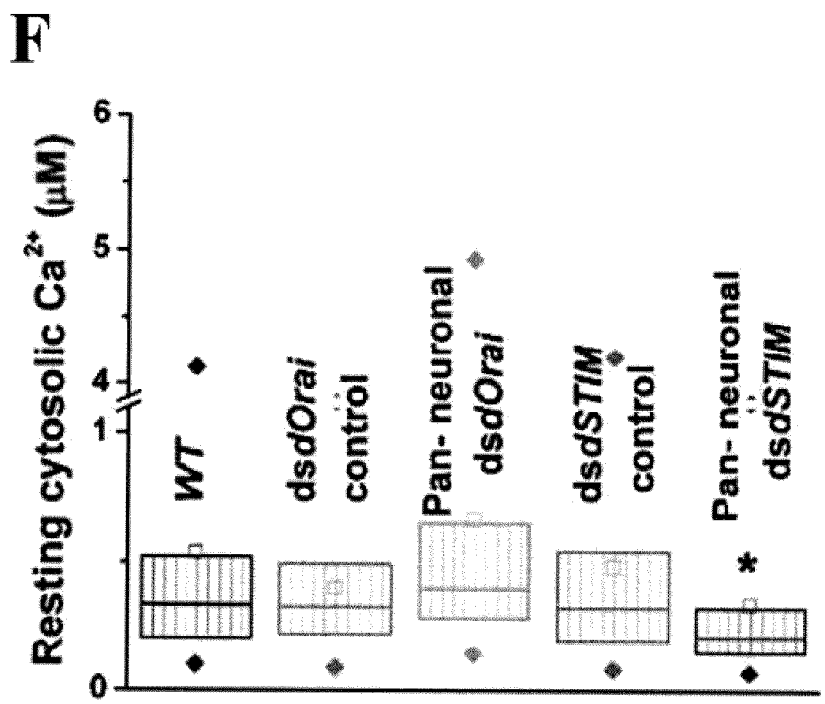

To investigate SOC channel activity in *Drosophila* neurons levels of dOrai transcripts were reduced using double-stranded RNA (dsRNA) in primary neuronal cultures derived from larval brains. SOCE was monitored by $Ca^{2+}$ imaging of cultured neurons in $Ca^{2+}$ add-back experiments, after depletion of endoplasmic reticular (ER) stores with thapsigargin in very low external $Ca^{2+}$ (FIG. 1a). SOCE was significantly reduced in neurons expressing dsRNA for dOrai (UASdOrai-RNAi221 denoted as dsdOrai; FIG. 1b, c). Furthermore, the level of intracellular store $Ca^{2+}$ ([$Ca^{2+}$]ER) was significantly lower in these cells (FIG. 1d) suggesting that $Ca^{2+}$ entry through *Drosophila* Orai channels contributes to the maintenance of store $Ca^{2+}$ in neurons.

To ascertain that the reduced SOCE observed in cells expressing dOrai dsRNA is gene specific, SOCE was measured in two alternate conditions. Double stranded RNA for the ER $Ca^{2+}$-sensor dSTIM, (UASdSTIMRNAi073 denoted as dsdSTIM) and a ligand-gated extracellular $Ca^{2+}$ channel, NMDAR1 (UASdNR1RNA1333 denoted as dsdNR1) were expressed in all neurons. Normal function of STIM is considered essential for Orai channel activity, while SOCE is not predicted to change when levels of a plasma membrane localized ligand-gated $Ca^{2+}$-channel are reduced. Pan-neural expression of dsdStim followed by $Ca^{2+}$ imaging revealed significant reduction of SOCE, [$Ca^{2+}$]ER (FIG. 1b, c) and resting cytosolic $Ca^{2+}$ ([$Ca^{2+}$]i; FIGS. 1e and f). A significantly higher frequency of cells with lower [$Ca^{2+}$]i were present among the neuronal population with dsdSTIM. However, dsdOrai expression had no effect on [$Ca^{2+}$]i suggesting differential efficacy of the two dsRNA strains for dOrai and dSTIM. The efficacy of the dsRNA strains used in these experiments was confirmed by semiquantitative RT-PCR.

Orai transcripts were consistently, reduced by pan-neural expression of dOrai dsRNA (ElavC155GAL4/+; UASdOrai-RNAi221; FIG. 8a, b). There was significant reduction in levels of dSTIM transcripts (FIG. 8c, d). As expected, reduction in the level of dNR1 transcripts did not affect store $Ca^{2+}$ or SOCE (FIGS. 8e and f). These results demonstrate that $Ca^{2+}$ influx, leading to replenishment of ER stores through the STIM-Orai pathway, is conserved in *Drosophila* neurons. Moreover, the single STIM encoding gene in *Drosophila* appears to regulate both [$Ca^{2+}$]ER and [$Ca^{2+}$]i. In mammalian systems these cellular properties are regulated independently by STIM1 and STIM2 respectively. See Brandman, O. et al., Cell, 131, 1327-1339 (2007).

Example 2

Reduced SOCE in *Drosophila* Neurons Causes Flight Defects

In order to determine if reduced SOCE in *Drosophila* neurons affects neuronal function, motor co-ordination defects were measured in the appropriate genotypes. No obvious changes were visible in larvae expressing dsRNA for either dOrai or dSTIM. The larvae were viable and pupated normally. However, adult flies with pan-neural expression of dsdOrai and dsdSTIM had defective wing posture (FIG. 2a, b). The wings of these flies were held apart. They were examined for their free flight ability by the "cylinder droptest" assay. See Benzer, S., Sci Am, 229, 24-37 (1973).

Reducing Orai and STIM by dsRNA in neurons resulted in a significant loss of flight in adults. While greater than 50% flies with dOrai knock-down were flightless, dSTIM knock-down resulted in a complete loss of flight (FIG. 2c). Expression of dsdOrai and dsdSTIM in glutamatergic neurons, which include the flight motor neurons, reduced flight ability in ~35% of adult *Drosophila*. The extent of flightless behavior was significant as compared with controls but less when compared with panneural expression of dsdOrai and dsdSTIM, suggesting that the requirement for SOCE in flight is in flight motor neurons and other neurons as well. Other adult motor activities such as walking and climbing remained unaffected upon down-regulation of dOrai or dSTIM.

To understand how neuronal store $Ca^{2+}$ and SOCE reduce flight ability, postsynaptic responses from the dorsal longitudinal indirect flight muscles (DLMs) that power flight, were measured. Electrophysiological recordings were obtained during tethered flight (initiated in response to an air-puff stimulus) and at rest (FIG. 2d, e, f). Non-fliers with pan-neural expression of dsdOrai and dsdSTIM, selected from the "cylinder drop" test were either unable to initiate rhythmic action potentials in response to an air puff stimulus or exhibited un-sustained (<5 s) and arrhythmic flight patterns (FIG. 2d). Knock-down by dsdOrai and dsdSTIM in glutamatergic neurons lead to a milder change in flight patterns as compared with pan-neural knock-down, consistent with a role for SOCE in non-glutamatergic inter-neurons in addition to the glutamatergic flight motor neurons. Recordings from resting DLMs of these flies revealed a high arrhythmic spontaneous firing rate of action potentials the frequency of which was significantly higher than WT (wild type) or other control flies (FIG. 2e, f).

Example 3

Over-Expression of dOrai+ in Neurons can Partially Suppress Flight Defects in *Drosophila* InsP3 Receptor Mutants SOCE activation through Orai and STIM in vivo requires a signal for depletion of intracellular $Ca^{2+}$ stores. The effect of over-expressing dOrai in the genetic background of itpr mutants was tested. For this purpose UASdOrai+ transgenic strains were generated and expressed in selected neuronal sub-domains. These include the glutamatergic domain tested above, the aminergic domain and the *Drosophila* insulin-like peptide 2 producing neurons (Dilp2 neurons). Expression of two copies of UASdOrai+ in Dilp2 neurons and the aminergic domain could partially suppress the altered wing posture of itprka1091/ug3 (hereafter referred to as itpr$^{ku}$; FIG. 3a). Though flight ability was not restored, there was initiation of flight patterns upon air puff delivery, normally completely lacking in itprku animals (FIG. 3b). Moreover, spontaneous hyperactivity of the DLMs in itprku was suppressed to a significant extent by expressing UASdOrai+ either ubiquitously (hsGAL4-leaky or hsGAL4L at 25° C.; 13) or in the aminergic, Dilp2 and glutamatergic sub-neuronal domains (FIG. 3c, d).

To ascertain whether dOrai+ function is required during flight circuit formation in pupae and/or during acute flight in adults ubiquitous expression of dOrai+ in UASdOrai+/hsGAL4L; itpr$^{ku}$ organisms was up-regulated by a heat-shock either in 24 hour pupae or in 1 day old adults. In both conditions a significant number of flies could initiate flight in response to an air-puff. Thus the level of dOrai+ can modulate flight circuit activity both during its development and in adult function (FIG. 3e). However, the flight patterns obtained were not sustained and appeared arrhythmic (FIG. 3f) indicating that while dOrai+ over-expression can suppress the flight defects and associated physiology of itpr mutant phenotypes to a significant extent, it is insufficient to regain complete flight.

Example 4

Intracellular Calcium Homeostasis in Itprku is Restored by Pan-Neuronal Expression of dOrai+

To understand the cellular basis of dOrai+ suppression of itpr mutant phenotypes, SOCE and $[Ca^{2+}]ER$ were measured in primary neurons from itprku larval brains using $Ca^{2+}$ addback experiments after maximal depletion of stores by application of thapsigargin in very low external $Ca^{2+}$ (FIG. 4a, b). SOC influx was greatly diminished (FIG. 4a, b) while $[Ca^{2+}]ER$ was significantly elevated in neurons derived from itprku larvae grown at 25° C., as compared to the 147. The mean $[Ca^{2+}]ER$ in itpr mutant appeared twice as much as WT (FIG. 4c). The percentage of cells with detectable SOC was approximately 3-5% as compared to 70-80% in WT.

A change in dOrai or dSTIM transcript levels in itprku larvae was not observed suggesting that a posttranscriptional change is responsible for the altered cellular properties. Pan-neural overexpression of dOrai+ in itprku neurons restored SOCE in itprku neurons to a significant extent. The percentage of cells with detectable SOCE increased to 70%. Moreover, $[Ca^{2+}]ER$ went back to WT levels. Over-expression of dOrai+ in WT neurons did not effect SOCE and $[Ca^{2+}]ER$. The distribution of $[Ca^{2+}]i$ in neuronal cells derived from itprku was similar to WT (~400 nM, FIG. 4d, e). However, in neuronal cell populations derived from brains with pan-neuronal over-expression of dOrai+, $[Ca^{2+}]i$ was elevated (~1 µM) both in WT and itprku backgrounds (FIG. 4d, e).

The significance of deranged SOCE and $[Ca^{2+}]ER$ in itprku neurons was determined by measuring these parameters in cells of itprku derived from second instar larvae maintained at 17.5° C. itprku is a cold-sensitive allelic combination and is lethal during the third instar larval stage at 17.5° C. See Joshi (2004) (supra).

SOCE and $[Ca^{2+}]ER$ in these conditions were similar to WT neurons grown under identical conditions at 17.5° C. (FIG. 9a, b). These data suggest that itprku organisms up-regulate store $Ca^{2+}$ at 25° C. as a compensatory mechanism to allow for survival at that temperature and that reduced SOCE may be a result of elevated store Ca2+. The observation that return of $[Ca^{2+}]ER$ and SOCE to normal by dOrai+ over-expression, is insufficient for restoration of complete flight in itprku suggests that other aspects of intracellular $Ca^{2+}$ signaling are essential for flight in these organisms.

Example 5

Restoration of Flight in Itprku by Dominant Alleles of dOrai and dSERCA

To investigate the additional properties of intracellular $Ca^{2+}$ signaling required for flight, genetic interactions between itpr and dOrai were further probed. For this purpose mutant alleles with P-inserts in the dOrai gene were obtained. The two alleles obtained, and referred to as dOrai1 and dOrai2, both contain an EP{gy2} construct at a distance of 13 bps from each other in the 5' un-translated region (UTR) of the dOrai gene (FIG. 10). See Bellen, H. J. et al., Genetics, 167, 761-781 (2004). The two dOrai alleles were initially tested for their interaction with itprku by measuring viability at 17.5° C.

Introduction of a single copy of either dOrai mutant allele could suppress cold-sensitive lethality of itprku (FIG. 11a). A single copy of either dOrai allele also suppressed the wing posture defect of itprku grown at 25° C. to a significant extent (FIG. 5a) suggesting that both dOrai1 and dOrai2 are gain of-function alleles (hypermorphs). Subsequent observations support this conclusion further. The presence of a single copy of either dOrai allele in the background of itprku restored flight initiation in response to an air-puff (FIG. 5e) and suppressed hyperactivity of flight NMJs (FIG. 5g, h). The extent of suppression remained unaffected by introducing a second mutant allele of dOrai in itpr mutant backgrounds, such as in the genotypes dOrai2/2; itprku and dOrai1/2; itprku.

The dOrai2/+ mutant allele can also partially suppress flight-related defects and reduced SOCE and $[Ca^{2+}]ER$ arising from pan-neuronal expression of dsdSTIM (FIG. 5d, f: FIG. 6e, f). However, store $Ca^{2+}$ and SOCE in neurons heterozygous for dOrai2/+ is not significantly different from WT (FIG. 11b).

Flies of the genotype dOrai2/Kum[170]; itpr[ku] exhibited normal wings (FIG. 5a) and normal levels of spontaneous electrical activity in DLM recordings consistent with the previously demonstrated dominant effect of Kum170. See Luik, R. M et al., Nature, 454, 538-542 (2008). Strikingly, flight ability was restored in a significant number of these triple mutant flies (FIG. 5b, c). This is in contrast to the complete loss of flight ability in itpr mutants and itpr, dOrai or itpr, dSERCA double mutant combinations. More than 60% of dOrai2/Kum[170]; itpr[ku] adults and nearly 50% of dOrai2/Kum170, itprku adults passed as "fliers" in the cylinder drop test assay (FIG. 5b). Air puff delivery elicited sustainable rhythmic flight patterns similar to wild-type in a high proportion of these flies (FIG. 5c). Down-regulating SERCA function thus restores or compensates for the additional intracellular $Ca^{2+}$ signaling deficits required for free flight, which are lacking in dOrai1 or 2/+; itprku organisms.

Example 6

$Ca^{2+}$ Release Through the InsP3 Receptor and SOCE Together Contribute to Maintenance of Flight $Ca^{2+}$ release through the InsP3R was measured by stimulating neurons ectopically expressing the *Drosophila* muscarinic acetylcholine receptor (mAChR) with increasing concentrations of the agonist carbachol. See Cordova, D. et al., Invert Neurosci, 5, 19-28 (2003); and Millar, N. S. et al., J Exp Biol, 198, 1843-1850 (1995). Pan-neuronal expression of the *Drosophila* mAChR had no measurable effect on viability or flight. For the WT InsP3R $Ca^{2+}$ release increased as a function of carbachol concentration (FIG. 9d); it was greatly attenuated in itprku (FIG. 6a, c, and FIG. 9d). Expression of mAChR transcripts, as determined by semiquantitative RT-PCR was similar in mutant and WT (FIG. 9c). $Ca^{2+}$ release in larval neurons derived from itprku larvae grown at 17.5° C. was also significantly lower as compared with controls under similar conditions (FIG. 9e).

Next, carbachol stimulated $Ca^{2+}$ release in itpr[ku] was measured in the presence of dOrai2 and Kum170 double and triple mutant combinations. Kum[170] had no direct effect on $Ca^{2+}$-release through the InsP3R upon carbachol stimulation. The presence of dOrai2 in either dOrai2/+; or in dOrai2/Kum170; itprku organisms restored carbachol stimulated $Ca^{2+}$ release to wild-type levels (FIG. 6a, b). However this restoration is clearly not the only factor in flight maintenance since dOrai2/+; itprku organisms are flightless. Additional parameters were measured that are likely to contribute to the flight rescue in triple mutants. These include perdurance of the carbachol stimulated $Ca^{2+}$ peak, SOCE, $[Ca^{2+}]ER$ and $[Ca^{2+}]i$.

The presence of a single copy of Kum170 delayed $Ca^{2+}$ sequestration following carbachol stimulated release and led to greater perdurance of the $Ca^{2+}$ peak; this effect of Kum170 was also present in cells derived from dOrai2/Kum170; itprku organisms (FIG. 6b, c). SOCE in neurons derived from dOrai2/Kum170; itprku larvae, was significantly elevated as compared to itprku and dOrai2/+; and Kum170/+; itprku (FIG. 6d, e). Thus, the combined effect of Orai2 and Kum170 on itprku is to restore near wild-type levels of InsP3 stimulated $Ca^{2+}$-release, followed by a broader curve of $Ca^{2+}$ persistence and normal SOCE. Consistent with the known function of SERCA, Kum170 had a dominant effect and reduced levels of store $Ca^{2+}$ in all genotypes tested including Kum170/+; itprku (FIG. 6f). Concurrent with the lower store, SOCE was greatly elevated in Kum170 heterozygotes (FIG. 6e). However, Kum170 was unable to restore SOCE in itprku neurons (FIG. 6d, e). Interestingly, $[Ca^{2+}]ER$ in dOrai2/+; itprku was also restored to normal, while cells with detectable SOCE went up from 3-5% (in itprku) to 72%. Over all SOCE remained low suggesting that the significant effect of a single copy of dOrai2 was restricted to a few critical neurons (FIG. 6e). Importantly, in the triple mutants $[Ca^{2+}]ER$ remained low (FIG. 6f), indicating that steady store $Ca^{2+}$ levels do not effect flight directly but perhaps contribute to the higher SOCE observed. Larval neurons heterozygous for dOrai2 or Kum170/+ had elevated levels of basal cytosolic $Ca^{2+}$ with or without itprku in the background (FIG. 11c, d). Higher $[Ca^{2+}]i$ is unlikely to contribute directly to flight rescue since itpr mutants with high $[Ca^{2+}]i$ also exhibit flight defects.

Example 7

*Drosophila* Strains

The viable itpr heteroallelic combination used in this study itprka1091/ug3 (referred to as itprku in the text) has single point mutations in the itpr gene that were generated in an EMS (ethyl methanesulfonate) screen. Detailed molecular information on these alleles has been published earlier. See Srikanth, S. et al., Biophys J, 86, 3634-3646 (2004); and Joshi, R. et al., Genetics, 166, 225-236 (2004). The UAS-mAChR transgenic strain on chromosome II was generated by injecting embryos using a standard protocol with a pUASTmAChR construct generated from the Dm mAChR cDNA clone.

Ca-P60AKum170ts (referred to as Kum[170] throughout the text) was obtained from Dr. K. S. Krishnan 23, dOrai11042 and dOrai20119 (referred as dOrai1 and dOrai2 respectively throughout the text) were procured from the Bloomington Stock Center (Bloomington, Ind.). UASRNAi strain for dOrai (12221), dSTIM (47073) and dNMDAR1 (dNR1; 37333), (referred throughout the text as dsdOrai, dsdSTIM and dsdNR1 respectively) were obtained from the Vienna *Drosophila* research centre (VDRC, Vienna). UAS dOrai strains with and without CFP tags were generated by Suzanne Ziegenhorn in the lab and mapped to chromosome 3.

The pan-neuronal GAL4 (used throughout the text) is ElavC155GAL4 mapped to X chromosome (Bloomington Stock Center, Bloomington, Ind.), glutamatergic GAL4 refers to OK371GAL4 36, aminergic refers to DdcGAL4 45, the GAL4 expressing in ILP2 producing neurons is DiIp2GAL4 46 and Ubiquitous GAL4 refers to hsp70GAL4 (Heat shockLeaky) which has basal expression at 25° C. Other fly strains were generated by standard genetic methods using individual mutant and transgenic fly lines described above.

Example 8

Larval Lethality and Staging

Staging experiments were done to obtain molting profiles of heteroallelic mutant larvae as described previously (Joshi, supra). Timed and synchronized egg collections were done for 8 h at 25° C. The cultures were then transferred to 17.5° C.

at which temperature development takes approximately double the time as compared to development at 25° C. Heteroallelic and heterozygous larvae were identified using dominant markers (TM6Tb and CyoGFP), and separated at 60 h AEL. They were transferred in 3 or more batches of 25 each to agarless cornmeal medium. Larvae were grown at 17.5° C. and screened at indicated time points for number of survivors and stage of development, determined by the morphology of the anterior spiracles. See Ashburner, M. *Drosophila*, a laboratory handbook. Cold Spring Harbor, N.Y.:Cold Spring Harbor Laboratory (1989).

Example 9

Heat Shock Experiments

Animals of the appropriate genotype were raised at 25° C. throughout development. In the designated cases, a heat shock of 37° C. was given for 2 hrs to pupae 24 h after puparium formation (APF) or a 90 min heat shock at 37° C. was given to 1 day old adult flies.

Example 10

Flight Assay and Electrophysiology

Flight tests were performed as described by following minor modifications of the "cylinder drop assay" described previously. See Benzer, S., Sci Am 229, 24-37 (1973); Banerjee, S., Lee, J. et al., J Neurosci, 24, 7869-7878 (2004). Flies were tested in batches of 20 by dropping them into a 1 m long glass cylinder. Flies that fell through directly into a chilled conical flask kept below were scored as non-fliers and those that flew and stuck to the walls of the cylinder were as scored fliers. The percentage of fliers was then determined. Computation of mean and standard error (SE) was performed using Origin 7.5 software (MicroCal, Northampton, Mass.). Statistically significant differences between two groups were determined by two-way Student's t-tests for independent populations. Significant differences were taken at $P<0.05$. Physiological responses to an air-puff stimulus were recorded from the dorsal longitudinal muscles (DLMs) of the giant fiber pathway. Flies were anaesthetized briefly using diethyl ether and tethered using nail polish to a thin metal wire inserted between the head and the thorax. Following recovery from anesthesia (~4 h), an un-insulated tungsten electrode sharpened by electrolysis was inserted into the DLM (fiber a), just beneath the cuticle.

A similar tungsten electrode was inserted into the abdomen served as the reference electrode. Flies were rested for 10 mins after insertion of the electrode before recording. Spontaneous firing was recorded by leaving the flies undisturbed in the dark for 2 minutes. Response to an air puff was then recorded from fiber a for 30 s by blowing a gentle puff of air. All recordings were done using an ISO-DAM8A (World Precision Instruments, Sarasota, Fla.) amplifier with filter set up of 30 Hz (low pass) to 10 kHz (high pass). Gap free mode of pClamp8 (Molecular Devices, Union City, Calif.) was used to digitize the data (10 kHz) on a Pentium 5 computer equipped with Digidata 1322A (Molecular Devices). Data were analyzed using Clampfit (Molecular Devices), and plotted using Origin 7.5 software.

Example 11

Primary Neuronal Cultures from *Drosophila* Larvae

Primary cultures of *Drosophila* larval neurons were plated in 200 µl *Drosophila* M1 medium (30 mM HEPES, 150 mM NaCl, 5 mM KCl, 1 mM $MgCl_2$, 1 mM $CaCl_2$, and 35 mM sucrose, pH 7.2) supplemented with 10% (v/v) fetal bovine serum (Invitrogen, USA), 50 U/ml penicillin, 50 µg/ml streptomycin, and 10 µg/ml Amphotericin B as described previously. See Wu et al., J. Neurosci., 3, 1888-1899 (1983). Briefly, brain and the ventral ganglion complex were dissected from *Drosophila* 3rd instar larvae of the appropriate genotypes. The brain tissue was mechanically dissociated using syringe needles in Schneider's medium containing collagenase (0.75 µg/µl) and dispase (0.4 µg/µl) and incubated in the proteolytic medium for 20 minutes to allow complete dissociation of the tissue. The lysate containing essentially single cells was then spun down, re-suspended in M1 medium (200 µl of M1 was used for lysates of four brains), and plated onto 35 mm culture dishes with a polylysine coated coverslip for the bottom. The cells were incubated at 22° C. for 14-16 h before imaging.

Example 12

Calcium Imaging in Larval Neurons

Larval neuron cultures were washed twice after growth for 14-16 h with *Drosophila* M1 medium and loaded in the dark with 2.5 µM Fluo-4 AM in M1 medium containing 0.002% Pluronic F-127, for 30 minutes at room temperature. The fluorescent dyes were obtained from Invitrogen Technologies, USA. After washing three times with M1, the cells were finally covered with 100 µl of $Ca^{2+}$ free M1 ($CaCl_2$ was substituted with equal concentration of $MgCl_2$) containing 0.5 mM EGTA and imaged within 40 minutes of loading. For quantitative analysis, a field with several cells was selected and imaged using the epifluorescence optics of a Nikon TE2000 inverted wide field microscope with an oil objective (60× and 1.4 numerical aperture) lens. Fluo-4 was excited for 20 ms using 488 nm wavelength illuminations from a mercury arc lamp. Emitted light was detected through a 505 nm bandpass filter (FITC filter set, 41001-exciter HQ480/40, dichroic Q505LP, emitter HQ535/50; Chroma, Brattleboro, Vt.). For basal cytosolic $Ca^{2+}$ measurements, cells were loaded with 5 µM Indo-1 AM for 45 minutes at room temperature at the end of which the dye was removed, the cells washed and finally covered with 100 µl of M1 containing 1 mM $CaCl_2$. Indo-1 in the cells was excited for 300 ms using the Indo-1 filter set from Chroma (71002-exciter 365/10, dichroic 380LP for emitter D405/30 and dichroic 440LP with emitter D485/25).

Fluorescent images were acquired using the Evolution QExi CCD camera and In vivo imaging software (Media Cybernetics, Silver Spring, Md.). The time lapse acquisition mode of the software was used to follow fluorescence changes in the cells every 10 s or 15 s for 15 frames. Different concentrations of carbachol (Fluka, Mo., USA), thapsigargin (Invitrogen, USA) 10 µM or ionomycin (Calbiochem, SD) 10 µM were added manually approximately 15 s after the start of data acquisition. For measurement of store-operated $Ca^{2+}$ entry, 1 mM $CaCl_2$ was added to the cells 225 s after thapsigargin addition. Images were acquired every 15 s. As controls, a series of images were acquired with the same imaging protocol without any additions. A total of 150-200 cells were analyzed from 5-7 dishes imaged for each genotype for each experiment.

Example 13

Data Analysis

For measuring fluorescence changes with time, images were processed using ImagePro plus software, V1.33. Fluorescence intensity before (Fbasal') and at various time points after addition of carbachol, thapsigargin, or CaCl$_2$ (Ft') were determined. Background fluorescence (an area without any cells) was subtracted from the values of Ft' and Fbasal' for each cell to obtain Ft and Fbasal The data were plotted using Origin 6.0 software as follows: ΔF/F=(Ft−Fbasal)/Fbasal for every time point. The maximum value of ΔF/F was obtained for every cell (Arrows in FIG. 1b) and a box chart representing the data spread was plotted. The rectangular boxes represent the spread of data points between 25-75% of cells, the horizontal line is the median and the small square within represents the mean. Significant differences between multiple groups of data were analyzed by one-way ANOVA or Kolmogorov-Smirnov (K-S) test of significance as indicated in the figure legends. For K-S test, cumulative frequency of cytosolic Ca$^{2+}$ levels was normalized to the total number of cells analyzed for every genotype and plotted against the log of [Ca$^{2+}$]i. The significance was calculated based on the maximum difference between the distributions referred to as the K-S statistic. Significant differences were taken at P<0.05.

Measurement of resting cytosolic Ca$^{2+}$ was done by obtaining values of Fbasal, Fmax (fluorescence at maximum saturation of the dye determined by adding ionomycin to allow the cells to equilibrate to external Ca$^{2+}$) and Fmin (fluorescence upon quenching all the free Ca$^{2+}$) was determined by adding 0.01% Triton-X and 1 mM EGTA). The values obtained were substituted in the Grynkiewicz equation:

$$[Ca^{2+}]i(\mu M)=(F\text{basal}-F\text{min})/(F\text{max}-F\text{basal}) \times Kd.$$

The published Kd value of 1.16 μM for Indo-1 in *Drosophila* S2 cells was used. See Hardie et al., J. Neurosci., 16, 2924-2933 (1996).

Example 14

Reverse Transcription Polymerase Chain Reaction (RT-PCR)

RNA was extracted from fifteen individuals of the indicated developmental stages using TRIZOL reagent (Invitrogen technologies, USA). Reverse transcription (RT) reactions were performed on 1 μg of total RNA using random hexaprimers (MBI, Fermentas) with Moloney murine leukemia virus (MMLV) reverse transcriptase (Invitrogen Technologies, USA) following standard protocols. 2 μl of the RT reaction product was used to perform PCR under standard conditions using the following primers.

```
dOrai
                                           (SEQ ID NO. 1)
Forward-5'  AGTTCTGCAGTGATCACCACTGG;
                                           (SEQ ID NO. 2)
Reverse-3'  CCGCTACCCGTGGGACTGTTG.

dSTIM
                                           (SEQ ID NO. 3)
Forward-5'  GAAGGCAATGGATGTGGTTCTG;
                                           (SEQ ID NO. 4)
Reverse-3'  CCGAGTTCGATGAACTGAGAG.

dNR1
                                           (SEQ ID NO. 5)
Forward-5'  AGGAGAAGGCCCTCAATCTC;
                                           (SEQ ID NO. 6)
Reverse-3'  TAGTAGCAACGGAGCATGTG.
```

```
rp49
                                           (SEQ ID NO. 7)
Forward-5'  CCAAGGACTTCATCCGCCACC;
                                           (SEQ ID NO. 8)
Reverse-3'  GCGGGTGCGCTTGTTCGATCC.

dmAChR
                                           (SEQ ID NO. 9)
Forward-5'  CAAGGACGAGTGCTACATCC;
                                           (SEQ ID NO. 10)
Reverse-3'  CCTAAATCAGAAGGCTCCTCC.
```

Example 15

Calcium Imaging Assay

Pseudo-color images of store Ca$^{2+}$ or [Ca$^{2+}$]$_{ER}$ and store-operated Ca$^{2+}$ entry (SOCE) in larval neurons of WT and itpr$^{ku}$. Store Ca$^{2+}$ was measured by depleting stores upon addition of 10 μM thapsigargin (Tpg). SOCE was monitored by inclusion of Ca$^{2+}$ (to a free concentration of 1 mM) at t=225 s, to the extracellular buffer. Scale bar represents 10 μm. Warmer colors represent higher Ca$^{2+}$. See FIG. 12(a). Single cell traces of store-depletion and resulting SOCE by Ca$^{2+}$ add-back experiments. See FIG. 12(b).

Example 16

One method of the present technology therefore is obtaining a human cell, such as a human fibroblast, or any human cell which expresses an InsP3R gene or ITPR (the homolog of the *Drosophila* itpr gene), which can be used to create an immortalized human cell line by providing a functional telomerase, after the human human cell genome has been modified to have a mutated InsP3R gene. See Alberts (supra) at Vol. III, Chapter 8 (Manipulating Proteins, DNA and RNA). Site-directed mutagenesis can be used to target mutations into the fibroblast InsP3R gene itpr/homolog gene, such as the point mutations described herein for itpr-ku mutations. See Sambrook et al., MOLECULAR CLONING: A LABORATORY MANUAL, (2d Ed), published by Cold Spring Harbor Laboratory (1989), which is incorporated herein by reference, particularly Chapter 15 on Site-Directed Mutagenesis. For an example of a *Homo sapiens* inositol 1,4,5-triphosphate receptor, type 1 nucleotide sequence see NCBI Reference Sequence: NM_001099952.1, which is incorporated herein by reference.

Once the human itpr/InsP3R gene has been so mutated, it may be cultured into a primary cell culture or an immortalized cell line according to the methods described herein. Then, the calcium ion flux and storage characteristic of the mutated cell can be imaged and evaluated in comparison to a non-mutated, wild-type normal human cell of the same origin. A number of different images can be obtained such as by according to the assay of the preceding Example in order to obtain a kind of "standard" resting calcium ion storage and flux traits of the mutated human cells.

Next a candidate compound can be added to an aliquot of the human cells and the cells then re-imaged after a period of time post-exposure to the compound. The calcium image of the cells that have been exposed to the compound can then be compared to the untreated human mutated cells and also to the wild-type, non-mutated human cells, and a conclusion derived as to whether the compound increases or decreases the intracellular calcium ion level of the mutated human cell. That compound can then be further evaluated for its ability to modulate calcium ion levels and thereby be a useful compound for, for example, a therapeutic for treating a disease or disorder characterized by abnormal calcium levels. That is, after performing the calcium itpr/InsP3R cell screening assay of the present technology, the candidate compound can be used to modulate the calcium level of a diseased cell type, or administered to an individual with an abnormal intracellular calcium ion storage properties, so as to modulate that abnormal property and thereby reach or approximate normal calcium levels in that cell type or individual.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

---

What is claimed is:

1. A method for identifying a compound that modulates store-operated calcium entry (SOCE) levels in a cell, comprising:
contacting a mutant mammalian cell with a test compound, wherein the mutant mammalian cell comprises a residual SOCE level and expresses a single 1,4,5-inositol triphosphate receptor (InsP$_3$R) gene (itpr) product, wherein the itpr gene is an itpr$^{ka1091/ug3}$ mutant, and wherein the itpr$^{ka1091/ug3}$ product contains G1891S and S224F point mutations; and measuring a SOCE level in the test compound contacted cell,
wherein a measured increase or decrease of the SOCE level versus the residual SOCE level identifies the compound as a compound that modulates SOCE levels.

2. The method of claim 1, further comprising:
measuring a SOCE level of a control cell and a SOCE level of the mutant mammalian cell; and
comparing the measured SOCE level of the mutant mammalian cell with the SOCE level of the control cell thereby determining the SOCE level difference between the control cell and mutant mammalian cell.

3. The method of claim 2, wherein the control cell is selected from the group consisting of: (i) a wild-type, normal cell, and (ii) a cell having wild-type calcium ion release.

4. The method of claim 1, wherein measuring a SOCE level comprises:
calcium imaging of the mutant mammalian cell and the test compound contacted mutant mammalian cell to obtain calcium imaging patterns and comparing the calcium imaging patterns before and after the contacting.

5. The method of claim 4, further comprising:
comparing the calcium imaging patterns of the mutant mammalian cell with calcium imaging patterns of a control cell.

6. The method of claim 5, wherein the control cell is selected from the group consisting of: (i) a wild-type, normal cell, and (ii) a cell having wild-type calcium ion release.

7. The method of claim 1, wherein the test compound is a compound effective for the treatment of cells having abnormal SOCE levels in a disease characterized thereby.

8. The method of claim 7, wherein the disease characterized by cells having abnormal SOCE levels is selected from the group consisting of spino-cerebellar ataxia (SCA), an immunodeficiency, severe combined immunodeficiency (SCID), Darier's disease (DAR), acute pancreatitis (AP), and Alzheimer's Disease (AD).

* * * * *

UNITED STATES PATENT AND TRADEMARK OFFICE
CERTIFICATE OF CORRECTION

PATENT NO. : 8,476,006 B2
APPLICATION NO. : 12/628064
DATED : July 2, 2013
INVENTOR(S) : Venkiteswaran et al.

It is certified that error appears in the above-identified patent and that said Letters Patent is hereby corrected as shown below:

In the Specification

In Column 1, Line 16, delete "Vig, M. et al," and insert -- Vig, M. et al., --, therefor.

In Column 6, Line 1, delete "W7)." and insert -- WT). --, therefor.

In Column 7, Line 21, delete "Kum1704" and insert -- Kum170/+ --, therefor.

In Column 8, Line 2, delete "UASdOraiRNAP$^{221/+}$," and insert -- UASdOraiRNAi$^{221/+}$, --, therefor.

In Column 8, Line 65, delete "W7)." and insert -- WT). --, therefor.

In Column 9, Line 7, delete "nucleotide&tool.FlyBase&val=CL 705 802" and insert -- nucleotide&tool=FlyBase&val=CL 705 802 --, therefor.

In Column 18, Line 60, delete "genotype" and insert -- genotype. --, therefor.

In Column 22, Line 15, delete "(UASdNR1RNA1333" and insert -- (UASdNR1RNAi333 --, therefor.

In Column 24, Line 6, delete "147." and insert -- WT. --, therefor.

In Column 24, Line 22, delete "elevated (-1" and insert -- elevated (~1 --, therefor.

In Column 30, Line 35, delete "human human" and insert -- human --, therefor.

Signed and Sealed this
Eighteenth Day of November, 2014

Michelle K. Lee
*Deputy Director of the United States Patent and Trademark Office*

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agttctgcag tgatcaccac tgg                                              23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttgtcaggg tgcccatcgc c                                                21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

-continued

```
gaaggcaatg gatgtggttc tg                                              22
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gagagtcaag tagcttgagc c                                               21
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
aggagaaggc cctcaatctc                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gtgtacgagg caacgatgat                                                 20
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ccaaggactt catccgccac c                                               21
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
cctagcttgt tcgcgtgggc g                                               21
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
caaggacgag tgctacatcc                                                 20
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cctcctcgga agactaaatc c                                              21

<210> SEQ ID NO 11
<211> LENGTH: 45
<212> TYPE: DNA
<213> ORGANISM: Drosophila melanogaster

<400> SEQUENCE: 11
tttcatacat gcacacaagt aaagcgtcga aatgctgttg aatta                    45

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
caagtaaagc gtcgaaatca tgatgaaat                                      29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tttcatacat gcacataagc atgatgaaat                                     30